US012718919B2

(12) United States Patent
Khandwalla et al.

(10) Patent No.: US 12,718,919 B2
(45) Date of Patent: Aug. 25, 2026

(54) COMPOSITIONS AND METHODS FOR THERAPEUTIC MANAGEMENT OF HEART FAILURE PATIENTS

(71) Applicant: Cedars-Sinai Medical Center, Los Angeles, CA (US)

(72) Inventors: Raj Khandwalla, Santa Monica, CA (US); Alex Shvartser, Tarzana, CA (US)

(73) Assignee: Cedars-Sinai Medical Center, Los Angeles, CA (US)

( * ) Notice: Subject to any disclaimer, the term of this patent is extended or adjusted under 35 U.S.C. 154(b) by 569 days.

(21) Appl. No.: 18/172,944

(22) Filed: Feb. 22, 2023

(65) Prior Publication Data

US 2023/0197232 A1 Jun. 22, 2023

Related U.S. Application Data

(63) Continuation-in-part of application No. PCT/US2021/049160, filed on Sep. 3, 2021.

(60) Provisional application No. 63/314,207, filed on Feb. 25, 2022, provisional application No. 63/074,805, filed on Sep. 4, 2020.

(51) Int. Cl.
*G16H 20/10* (2018.01)
*A61B 5/00* (2006.01)

(52) U.S. Cl.
CPC ........... *G16H 20/10* (2018.01); *A61B 5/4848* (2013.01)

(58) Field of Classification Search
None
See application file for complete search history.

(56) References Cited

U.S. PATENT DOCUMENTS 9,689,866 B2 6/2017 Sheard et al.
2006/0259330 A1* 11/2006 Schranz ................. G16H 20/10 235/487
2007/0265230 A1* 11/2007 Rousso .................. A61K 31/66 514/137

(Continued)

FOREIGN PATENT DOCUMENTS

WO 2022/051678 A1 10/2022

OTHER PUBLICATIONS

Webster R, Murphy A, Bygrave H, Ansbro É, Grobbee DE, Perel P. Implementing Fixed Dose Combination Medications for the Prevention and Control of Cardiovascular Diseases. Glob Heart. Aug. 19, 2020;15(1):57. doi: 10.5334/gh.860. PMID: 32923350; PMCID: PMC7442173.*

(Continued)

*Primary Examiner* — Katherine Kolosowski-Gager
(74) *Attorney, Agent, or Firm* — Black Swan Intellectual Property

(57) ABSTRACT

Disclosed herein are systems and methods for management and administration of therapeutic treatment regimens for heart failure patients. In some examples, this includes monitoring a patient's heart rate and electrocardiogram using a wearable heart rate sensor to provide input into a decision tree model to provide an effective treatment regimen. Furthermore, regular blood pressure measurements may be input into the model. The system may additionally iterate through various heart failure therapeutics based on a patient's response to prior administered therapeutics.

8 Claims, 42 Drawing Sheets

(56) References Cited

U.S. PATENT DOCUMENTS

| | | | | |
|---|---|---|---|---|
| 2011/0077971 | A1* | 3/2011 | Surwit | G16H 40/63 705/2 |
| 2017/0231560 | A1 | 8/2017 | Hyde | |
| 2017/0231568 | A1* | 8/2017 | An | A61B 5/0205 600/301 |
| 2017/0238867 | A1 | 8/2017 | Javed | |
| 2019/0083030 | A1* | 3/2019 | Thakur | A61B 5/7275 |
| 2019/0125273 | A1 | 5/2019 | Sharma | |

OTHER PUBLICATIONS

Extended European Search Report in European Patent Application No. 21865231.1, mailed Sep. 9, 2024 (12 pages).
Ansari, et al., “Improving guideline adherence: a randomized trial evaluating strategies to increase β-blocker use in heart failure,” Circulation 107.22 (2003): 2799-2804.
Balakumaran, et al., “Evaluation of a guideline directed medical therapy titration program in patients with heart failure with reduced ejection fraction,” IJC Heart & Vasculature Volum 22, Mar. 2019, pp. 1-5.
Basu, et al., “Medicare Chronic Care Management Payments and Financial Returns to Primary Care Practices: a modeling study,” Annals of Internal Medicine 163.8 (2015): 580M 588.
Bloom, et al., The global economic burden of noncommunicable diseases.Technical report, Program on the Global Demography of Aging, Geneva, Switzerland, 2012.
Buttorff, et al., Multiple chronic conditions in the United States, Santa Monica, CA: Rand, 2017.
Driscoll, et al., “Nurse-Let Titration of Angiotensin-Converting Enzyme Inhibitosl, β-Adrenergic Blocking Agents, and Angiotensin Receptor Blockers in Patients with Heart Failure with Reduced Ejection Fraction,” JAMA Cardiology 1.7(2016): 842-843.
Fonarow, et al., “Improving evidence-based care for heart failure in outpatient cardiology practices: primary results of the Registry to Improve the Use of Evidence-Based Heart Failure Therapies in the Outpatient Setting (Improve HF),” Circulation 122.6 (2010): 585-596.
Fonarow, et al., “Potential Impact of optimal implementation of evidence-based heart failure therapies on mortality,” American Heart Journal 161.6 (2011): 1024-1030.
Fryar, et al. “Hypertension prevalence and control among adults: United States 2015-2016,” (2017): 1-8.
Gislason, et al., “Persistent Use of Evidence-Based Pharmacotherapy in Heart Failure is Associated with Improved Outcomes,” Circulation, 2007; 116:737-744.
Glynn, et al. “Disparities in Cardiovascular Mortality Related to Heart Failure in the United States” Journal of the American College of Cardiology 73.18 (2019): 2354.
Greene, et al., “Medical Therapy for Heart Failure With Reduced Ejection Fraction,” Journal of the American College of Cardiology, Jul. 2018, 72 (4) 351-366.
https://www.cms.gov/Research-Statistics-Data-and-Systems/Statistics-Trends-and-Reports/Chronic-Conditions/Downloads/2012Chartbook.pdf.
International Search Report and Written Opinion mailed Dec. 16, 2021 in International Patent Application No. PCT/US21/49160 (8 pages).
International Search Report and Written Opinion mailed Jun. 2, 2023 in International Patent Application No. PCT/US23/63054 (11 pages).
Jain, et al., “Success of a multidisciplinary heart failure clinic for initiation and up-titration of key therapeutic agents,” Eur J Heart Fail, 7 (2005), pp. 405-410.
Lozano, et al., “Progress towards Millennium Development goals 4 and 5 on maternal and child mortality: an updated systematic analysis,” The Lancet, 378(9797):1139-1165, 2011.
McMurray, et al., “Angiotensin-neprilysin inhibition versus enalaprin in heart failure,” New England Journal of Medicine 371.11 (2014):993-1004.
Swedberg, et al., “Ivabradine and outcomes n chronic heart failure (Shift): a randomized placebo-controlled study,” The Lance 376. 9744 (2010): 875-885.
Thomas, et al., “Association of changes in heart failure treatment with patients' health status: real-world evidence from Champ-HF,” JACC: Heart Failure 7.7 (2019): 615-625.
Williams, Jackson, “Improvement In Chronic Disease Outcomes For Medicare Benficiaries Has Stalled—Where Do We Go From Here?” Health Affirs Blog, Jan. 28, 2020, DOI: 10.1377/hblog20200127.583888.
The Heart failure and Optimal Outcomes from Pharmacy Study (HOOPS) European Journal of Heart Failure (2011) 13, 917-924 di:10.1093/eurjhf/hfr083.

* cited by examiner

| Drug | Class | Level 1 | Level 2 | Level 3 | Level 4 | Level 5 |
|---|---|---|---|---|---|---|
| **Bisoprolol** | Beta blocker | 1.25 mg QD | 2.5 mg QD | **5 mg QD** | 10 mg QD# | 10 mg QD# |
| **Carvedilol** | Beta blocker | 3.125 mg BID | 6.25 mg BID | **12.5 mg BID** | 25 mg BID* | 50 mg BID* |
| **Metoprolol succinate** | Beta blocker | 12.5 mg QD | 25 mg QD | 50 mg QD | **100 mg QD** | 200 mg QD# |
| **Captopril** | ACEI | 6.25 mg TID | 12.5 mg TID | **25 mg TID** | 50 mg TID# | 50 mg TID# |
| **Enalapril** | ACEI | 2.5 mg qd | 2.5 mg BID | **5 mg BID** | 10 mg BID# | 20 mg BID |
| **Fosinopril** | ACEI | 2.5 mg QD | 5 mg QD | 10 mg QD | **20 mg QD** | 40 mg QD# |
| **Lisinopril** | ACEI | 2.5 mg QD | 5 mg QD | 10 mg QD | **20 mg QD** | 40 mg QD# |
| **Perindopril** | ACEI | 2 mg QD | 4 mg QD | **8 mg QD** | 16 mg QD# | 16 mg QD# |
| **Quinapril** | ACEI | 2.5 mg QD | 2.5 mg BID | 5 mg BID | **10 mg BID** | 20 mg BID# |
| **Ramipril** | ACEI | 1.25 mg QD | 2.5 mg QD | **5 mg QD** | 10 mg QD# | 10 mg QD# |
| **Trandalopril** | ACEI | 1 mg QD | **2 mg QD** | 4 mg QD# | 4 mg QD# | 4 mg QD# |
| **Candesartan** | ARB | 4 mg QD | 8 mg QD | **16 mg QD** | 32 mg QD# | 32 mg QD# |
| **Losartan** | ARB | 12.5 mg QD | 25 mg QD | **50 mg QD** | 100 mg QD# | 100 mg QD# |

FIG. 9A

| Drug | Class | Level 1 | Level 2 | Level 3 | Level 4 | Level 5 |
|---|---|---|---|---|---|---|
| **Valsartan** | ARB | 40 mg QD | 40 mg BID | **80 mg BID** | 160 mg BID# | 160 mg BID# |
| **Olmesartan** | ARB | 10 mg QD | **20 mg QD** | 40 mg QD# | 40 mg QD# | 40 mg QD# |
| **Sacubitril / Valsartan** | ARNI | 12/13 mg BID | **24/26 mg BID** | 49/51 mg BID | 97/103 mg BID# | 97/103 mg BID |
| **Spironolactone** | MRA | **12.5 mg QD** | 25 mg QD# | 25 mg BID | 25 mg BID | 25 mg BID |
| **Eplerenone** | MRA | **25 mg QD** | 50 mg QD# | 50 mg QD | 50 mg QD | 50 mg QD |
| **Dapagliflozin** | SGLT2i | **5 mg** | 10 mg QD | 10 mg QD | 10 mg QD | 10 mg QD |
| **Empagliflozin** | SGLT2i | 10 mg QD# | 25 mg QD | 25 mg QD | 25 mg QD | 25 mg QD |
| **Canagliflozin** | SGLT2i | 100 mg QD | 200 mg QD | 300 mg QD | 300 mg QD | 300 mg QD |
| **Ertugliflozin** | SGLT2i | 5 mg QD | 10 mg QD | 15 mg QD | 15 mg QD | 15 mg QD |
| **50% of target dose**<br><br># Target Dose | | | | | | |

FIG. 9B

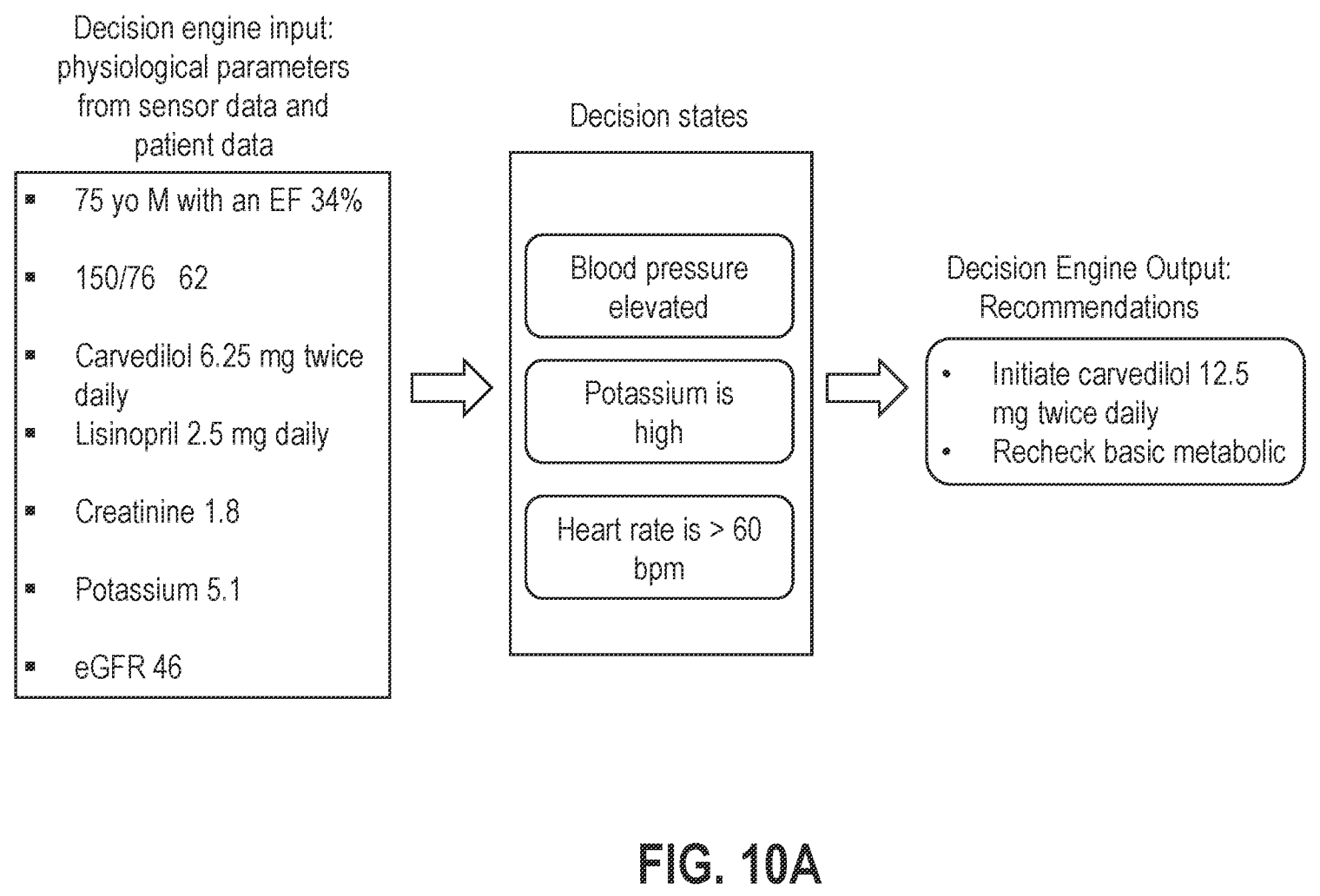

Decision engine input: physiological parameters from sensor data and patient data

- 75 yo M with an EF 34%
- 150/76 62
- Carvedilol 6.25 mg twice daily
- Lisinopril 2.5 mg daily
- Creatinine 1.8
- Potassium 5.1
- eGFR 46

Decision states

- Blood pressure elevated
- Potassium is high
- Heart rate is > 60 bpm

Decision Engine Output: Recommendations

- Initiate carvedilol 12.5 mg twice daily
- Recheck basic metabolic

FIG. 10A

COMPOSITIONS AND METHODS FOR THERAPEUTIC MANAGEMENT OF HEART FAILURE PATIENTS

CROSS REFERENCE TO RELATED APPLICATIONS

This application claims priority to and the benefit of U.S. Provisional Application No. 63/314,207, filed Feb. 25, 2022, and is a continuation-in-part of International Application No. PCT/US2021/049160, filed Sep. 3, 2021, which claims priority to and the benefit of U.S. Provisional Application No. 63/074,805, filed Sep. 4, 2020, each of which is hereby incorporated by reference herein in its entirety.

TECHNICAL FIELD

The present description relates to compositions, systems, and methods for management of heart failure therapeutics for heart failure patients.

BACKGROUND

The following description includes information that may be useful in understanding the present invention. It is not an admission that any of the information provided herein is prior art or relevant to the presently claimed invention, or that any publication specifically or implicitly referenced is prior art.

Despite continuous efforts and development of new therapeutic agents to treat heart failure (HF), prevalence of HF has increased and continues to increase globally. Further, the overall mortality rate associated with heart failure has increased since 2011.

Further, with increasing number of newer pharmacological therapeutic agents and with more investigational therapeutic agents in various stages of development, clinical decision making, including prescription and management of HF therapeutic agents, has become increasingly challenging and time consuming.

Furthermore, clinical inertia, which occurs when clinicians fail to initiate or intensify evidence-based therapy or achieve prescribed targets in their patients (such as, with blood pressure or blood sugar), reduces potential improvement in clinical outcomes for HF.

Due to at least some of the above-mentioned factors, although new HF therapies for decreasing HF-related mortality are being developed and approved for use, the overall HF-related mortality and/or hospitalization does not appear to be declining and may be increasing. Thus, new systems and methods for implementing HF therapies are needed.

SUMMARY

Systems and methods to at least partially address some of the above-mentioned issues, including systems and methods for determining and managing therapeutic regimen for HF therapeutic agents, are disclosed herein. In one example, a method comprises: acquiring physiological sensor data of a patient from one or more physiological sensors; receiving a patient profile referenced to the patient, the patient profile comprising a therapeutic dosage regimen comprising at least one therapeutic agent and an associated dosage; processing the physiological sensor data using a model to modify the therapeutic dosage regimen and output an updated therapeutic dosage regime; and administering to the patient the updated therapeutic dosage regime.

In this way, by continuously evaluating and updating the therapeutic regimen for HF patients using remote monitoring data and patient data, target dosage for a given HF therapeutic agent is achieved with improved efficiency, which improves clinical outcomes for HF patients and reduces hospitalization and mortality risk.

As one example, a clinician may prescribe the use of a digital therapeutic decision engine for evaluation and/or management of a therapeutic regimen for a heart failure patient. During a monitoring period, the decision engine may receive patient data input from an electronic health record (EHR) of the patient and from one or more remote monitoring devices (e.g., wearable devices and/or non-wearable devices). Using the patient data and the remote monitoring data, the decision engine may determine whether a patient is stable enough for a change in his or her medications. If the patient is clinically stable, the decision engine may determine if clinician input is required, and if not, the decision engine may automatically provide an update to initiate at least one medication at an associated dosage or change (e.g., increase or decrease) dosage of or discontinue at least one other medication and/or check labs.

In some examples, if the decision engine either initiates a medication or changes the dosage of a medication in the therapeutic regimen or discontinues a medication, the patient may receive one or more of an information that educates the patient on the rationale for the decision and a notification requesting for the patient's acknowledgement. Once approved and the medication change has been made, data from the wearable devices and/or patient response input via a patient questionnaires embedded in a patient-side app may be used to monitor the patient for any medication side effects and/or intolerances over a patient response monitoring period.

In this way, continuous remote monitoring during dose titration ensures that medications are initiated, changed and/or dosages updated when the patient is stable and monitors patients for medication side effects so that they can be quickly detected. If one or more side effects and intolerances are detected, a safety decision component of the decision engine may be executed, where the safety decision component provides evaluates the therapeutic regimen based on thresholds for kidney function, hyperkalemia, hypotension, and/or bradycardia, and provides updates to the therapeutic regimen to discontinue or decrease the dosage of a medication (e.g., a medication that was initiated). In some examples, recommendations may be provided which are then updated upon approval by a clinician.

In this way, the methods and systems described herein incorporate data derived from remote patient monitoring devices to determine an effective therapeutic treatment regimen or modify an existing regimen or maintain the existing regimen, or initiate one or more laboratory test procedures. In some examples, a follow-up schedule for the patient may be automatically generated. Further, by monitoring the patient before as well as after updating a therapeutic regime, and adjusting medications according to patient response, customized and personalized heart failure therapy is efficiently executed. As a result, patient outcome for HF patients is improved, which reduces mortality risk and hospitalization.

As another example, the decision engine may process heart rate data collected by wearable heart rate monitors to output a new or modified therapeutic treatment regimen. This may include monitoring of an average heart rate over periods of time (e.g. 1, 2, 3, 4, 5, or 6 hours, days, weeks) that would not be possible at a clinical visit. Accordingly, utilization of longitudinal heart rate, electrocardiogram, and blood pressure data will allow delivery of therapeutic treatment regimens that may reduce mortality rates among patient populations. Therefore, disclosed are systems and methods for determining and implementing therapeutic dosage regimens based on feedback from wearable heart rate monitoring devices and blood pressure cuff measurements, among other input data.

According to some implementations of the present disclosure, a method for managing a therapeutic regiment of a patient diagnosed with heart failure is disclosed. The method includes receiving a first set of physiological sensor data acquired from the patient during a first time period. The first set of physiological sensor data is output via one or more remote monitoring devices. The method further includes receiving a set of patient data from a patient profile referenced to the patient. The set of patient data includes the therapeutic regimen comprising at least one therapeutic agent and an associated dosage. The method further includes processing the first set of physiological sensor data and the set of patient data based on a patient stability to output an updated therapeutic regimen. The method further includes administering the updated therapeutic regimen to the patient.

According to some implementations of the present disclosure a method comprises generating an updated therapeutic regimen for a patient diagnosed with heart failure based on (i) a first set of physiological parameters of the patient acquired via one or more remote monitoring devices and (ii) a set of patient data acquired via the patient's health record. The method further includes administering the updated therapeutic regimen to the patient. The updated therapeutic regimen includes a change in dosage of at least one previously administered therapeutic agent, an initiation of at least one new therapeutic agent, or both. The new therapeutic agent is different from the previously administered therapeutic agent.

According to some implementations of the present disclosure, a system for managing an initial therapeutic regimen for a patient with heart failure is disclosed. The system includes one or more physiological sensors and a processing system. The one or more physiological sensors are configured to acquire a set of physiological sensor data from the patient. The processing system includes at least one processor communicably coupled to at least one non-transitory memory storing a decision engine. The at least one non-transitory memory stores executable instructions that when executed causes the processor to implement a method. The method includes acquiring the set of physiological sensor data from the one or more physiological sensors. The method further includes acquiring a set of patient data from an electronic health record system communicatively coupled to the processor. The electronic health record system stores patient data referenced to the patient. The patient data includes one or more therapeutic agents and associated dosages. The method further includes, during a first condition when a stability of the patient is above a first threshold, processing the set of physiological sensor data and the set of patient data according to a first mode of operation of the decision engine and outputting a first updated therapeutic regimen based on the initial therapeutic regimen. The therapeutic regimen including the one or more therapeutic agents and associated dosages. The method further includes, during a second condition when the stability of the patient is below the first threshold, processing the set of physiological sensor data and the set of patient data according to a second mode of operation of the decision engine and output a second updated therapeutic regimen based on the initial therapeutic regimen.

According to some implementations of the present disclosure, a method of treating, preventing, ameliorating, or reducing the likelihood of developing a cardiac health condition in a patient is disclosed. The method includes remotely managing a therapeutic regimen of the patient. Remotely managing the therapeutic regimen of the patient includes remotely generating, via a decision engine, the therapeutic regimen for the patient based on patient stability. Remotely managing the therapeutic regimen of the patient further includes receiving patient data from the patient. The patient data includes one or more of sensor data from one or more physiological sensors, medication adherence data, medication side effects data, medical history data, and laboratory data. Remotely managing the therapeutic regimen of the patient further includes updating the therapeutic regimen based on the patient data. Updating the therapeutic regimen based on the patient data includes generating a follow-up schedule based on the updates to the therapeutic regimen and the patient data. Updating the therapeutic regimen based on the patient data further includes increasing one or more medications, maintaining one or more medications, decreasing one or more medications, discontinuing one or more medications, determining one or more of a timing for laboratory testing and a type of laboratory testing, or any combination thereof.

It should be understood that the summary above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The accompanying drawings, which are incorporated in and constitute a part of this specification, exemplify the embodiments of the present invention and, together with the description, serve to explain and illustrate principles of the invention. The drawings are intended to illustrate major features of the exemplary embodiments in a diagrammatic manner. The drawings are not intended to depict every feature of actual embodiments nor relative dimensions of the depicted elements, and are not drawn to scale.

FIGS. 9A and 9B are tables of example therapeutics and different levels given for heart failure patients, according to some implementations of the present disclosure.

FIGS. 10A and 10B show example inputs, example indication of decision states, and example outputs generated for a patient during respective updates of the therapeutic regimen of the patient, according to some implementations of the present disclosure.

Figure 1A:
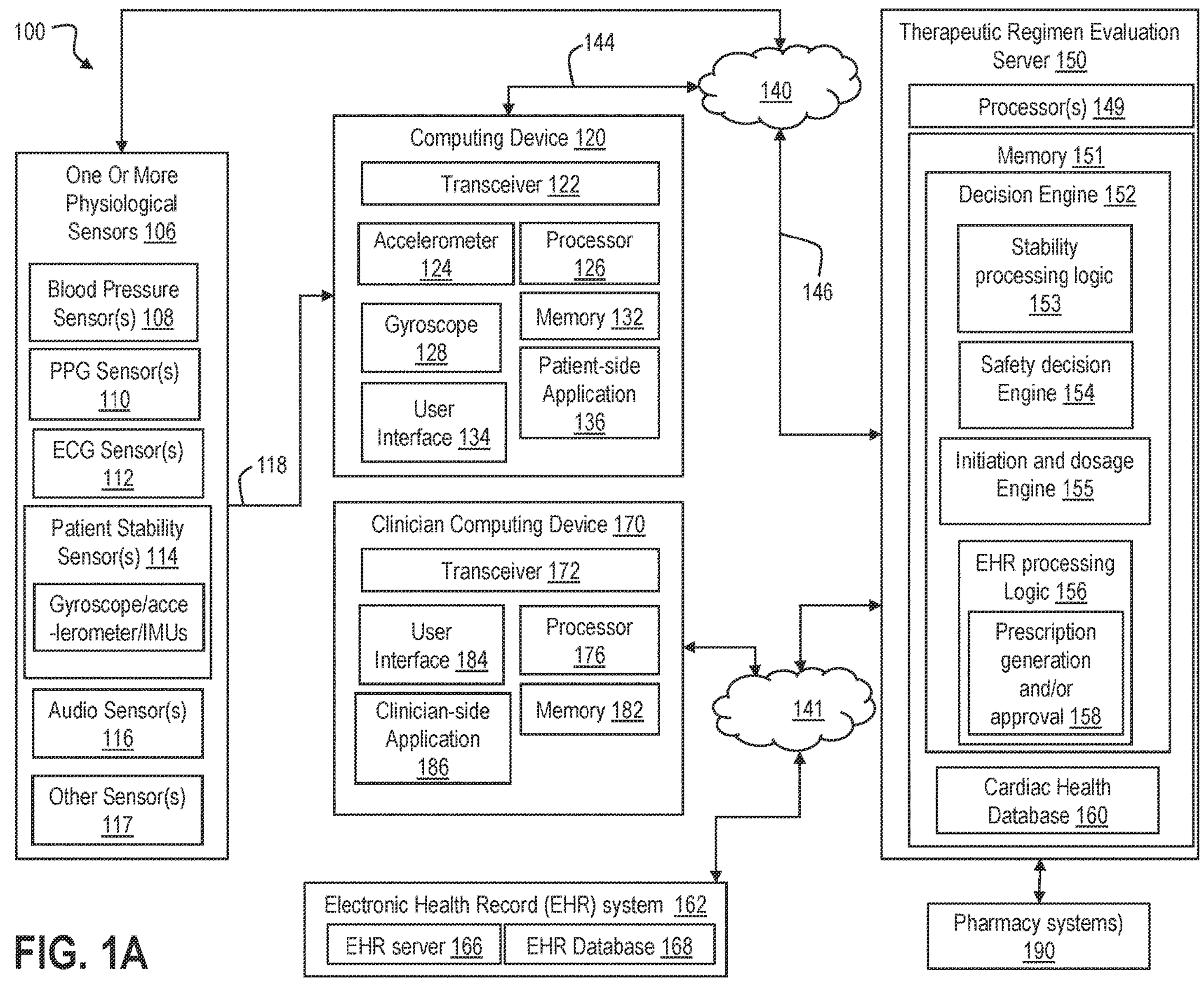
FIG. 1A shows a schematic diagram of an example of a system for managing a therapeutic regimen of a patient diagnosed with heart failure, according to some implementations of the present disclosure.

In the drawings, the same reference numbers and any acronyms identify elements or acts with the same or similar structure or functionality for ease of understanding and convenience. To easily identify the discussion of any particular element or act, the most significant digit or digits in a reference number refer to the Figure number in which that element is first introduced.

DETAILED DESCRIPTION

Unless defined otherwise, technical and scientific terms used herein have the same meaning as commonly understood by one of ordinary skill in the art to which this invention belongs. Szycher's Dictionary of Medical Devices CRC Press, 1995, may provide useful guidance to many of the terms and phrases used herein. One skilled in the art will recognize many methods and materials similar or equivalent to those described herein, which could be used in the practice of the present invention. Indeed, the present invention is in no way limited to the methods and materials specifically described.

In some embodiments, properties such as dimensions, shapes, relative positions, and so forth, used to describe and claim certain embodiments of the invention are to be understood as being modified by the term "about."

Various examples of the invention will now be described. The following description provides specific details for a thorough understanding and enabling description of these examples. One skilled in the relevant art will understand, however, that the invention may be practiced without many of these details. Likewise, one skilled in the relevant art will also understand that the invention can include many other obvious features not described in detail herein. Additionally, some well-known structures or functions may not be shown or described in detail below, so as to avoid unnecessarily obscuring the relevant description.

The terminology used below is to be interpreted in its broadest reasonable manner, even though it is being used in conjunction with a detailed description of certain specific examples of the invention. Indeed, certain terms may even be emphasized below; however, any terminology intended to be interpreted in any restricted manner will be overtly and specifically defined as such in this Detailed Description section.

While this specification contains many specific implementation details, these should not be construed as limitations on the scope of any inventions or of what may be claimed, but rather as descriptions of features specific to particular implementations of particular inventions. Certain features that are described in this specification in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations may be depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the implementations described above should not be understood as requiring such separation in all implementations, and it should be understood that the described program components and systems can generally be integrated together in a single software product or packaged into multiple software products.

Overview

Figure 1B:
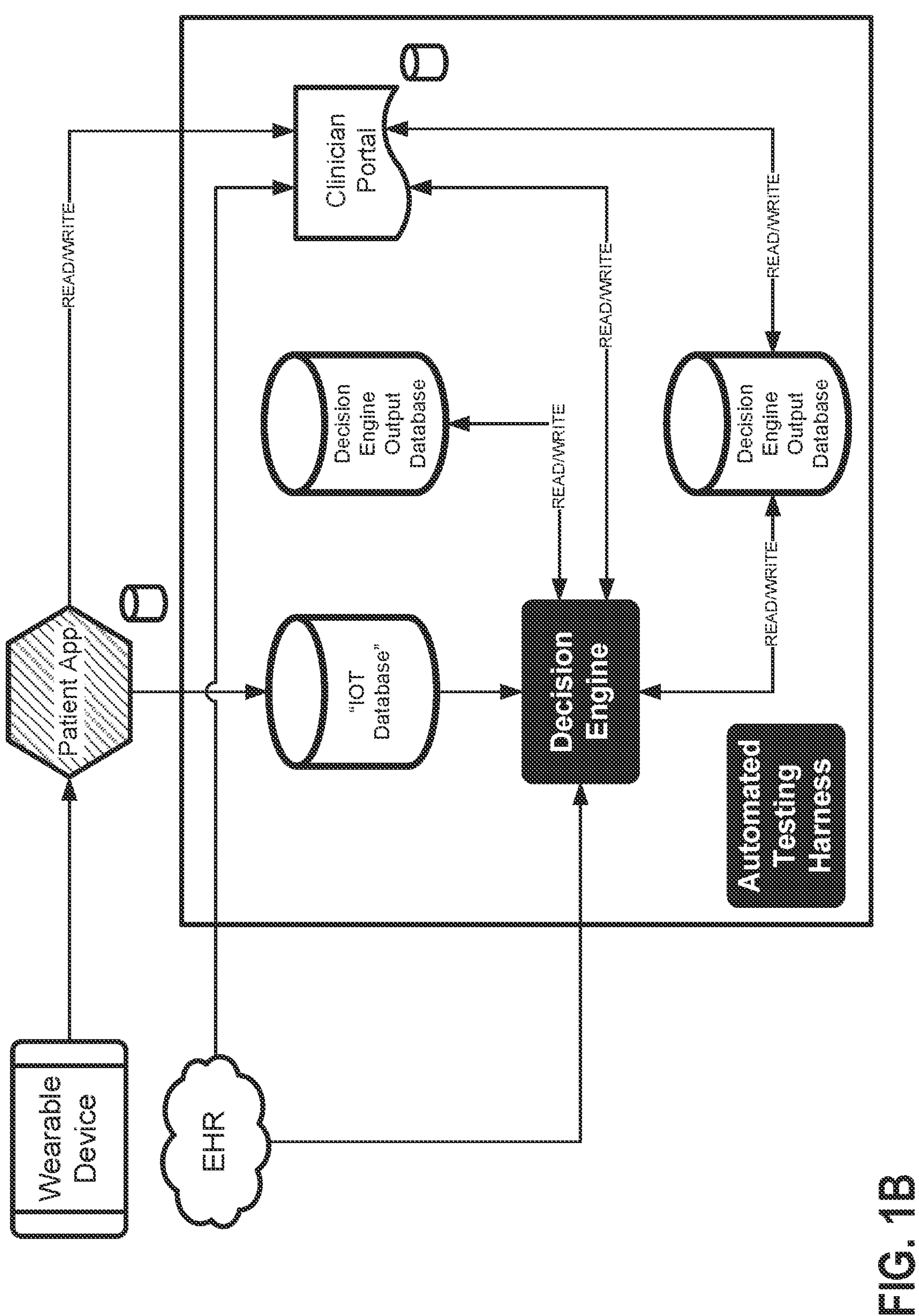
FIG. 1B shows schematic diagram of another example of a system for managing a therapeutic regimen of a patient diagnosed with heart failure, according to some implementations of the present disclosure.
Figure 1C:
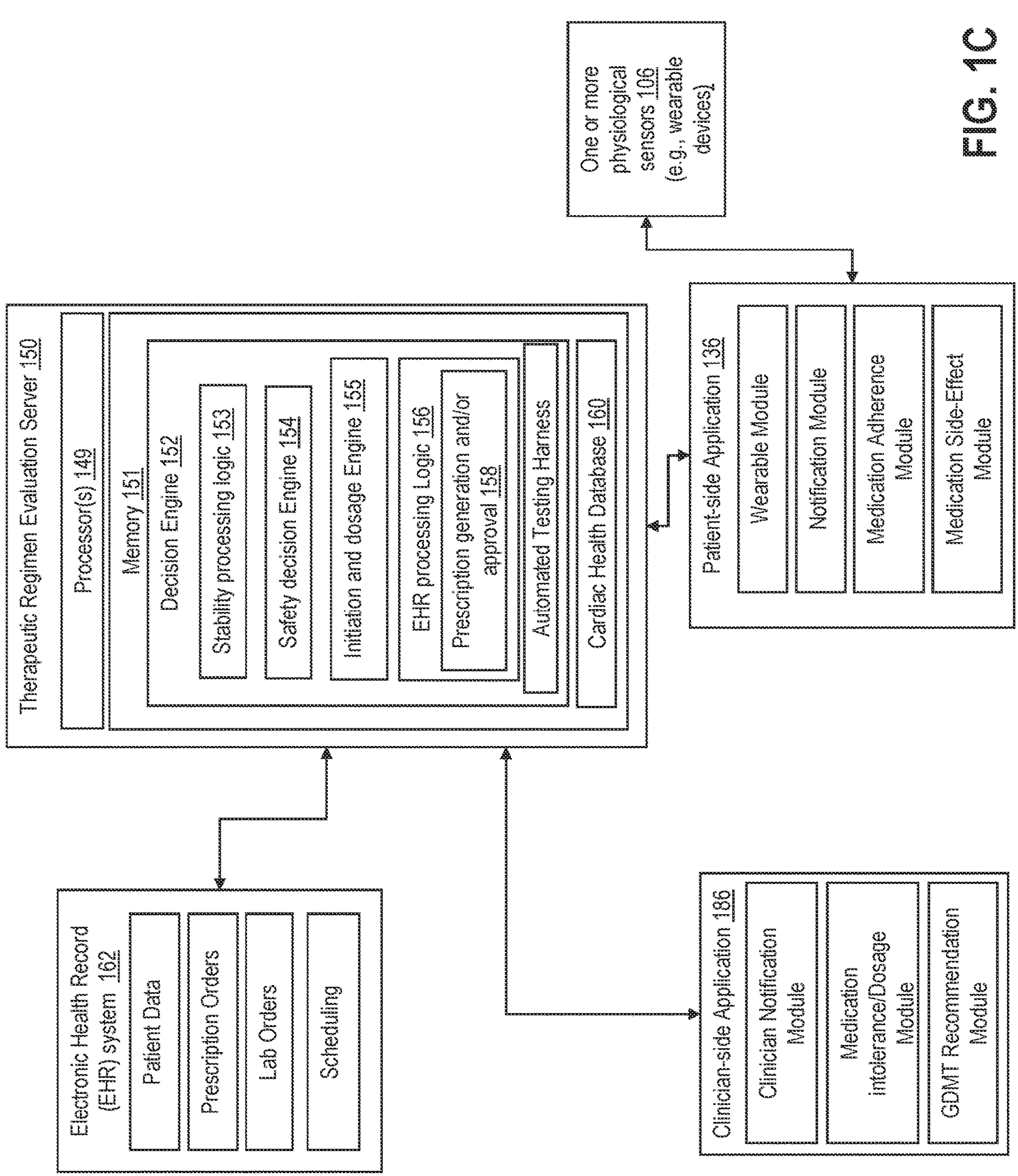
FIG. 1C shows a schematic diagram of another example of a system for managing a therapeutic regimen of a patient diagnosed with heart failure, according to some implementations of the present disclosure.

The present description relates to systems and methods for evaluating and/or managing a therapeutic regimen for a patient diagnosed with heart failure and undergoing treatment with one or more therapeutic agents for heart failure (HF). In one example, systems and methods are provided for periodically evaluating and updating a therapeutic regimen of the patient diagnosed with heart failure using remote patient monitoring data from one or more remote patient monitoring devices and using patient health data from an electronic health record of the patient. For example, the therapeutic regimen is periodically evaluated and updated according to guideline-directed medical therapy using a decision-tree model and an evidence-based approach as discussed herein. An example system for evaluating and/or managing a therapeutic regimen for a HF patient is shown at FIGS. 1A-1C.

Figure 2:
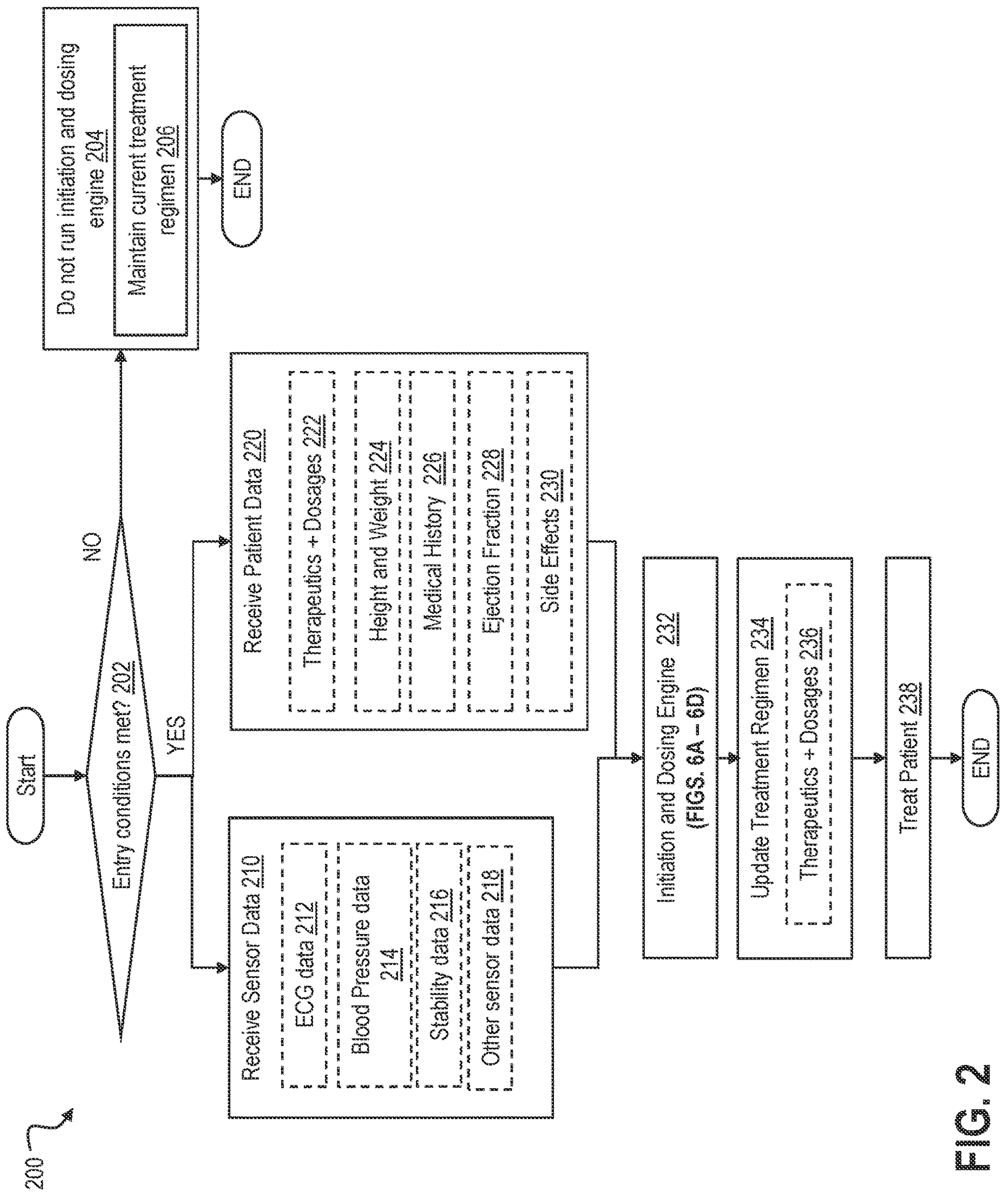
FIG. 2 shows a high-level flow chart of an example method for managing a therapeutic regimen of a patient based on input from one or more physiological sensors and patient data from a patient health record, according to some implementations of the present disclosure.
Figure 7:
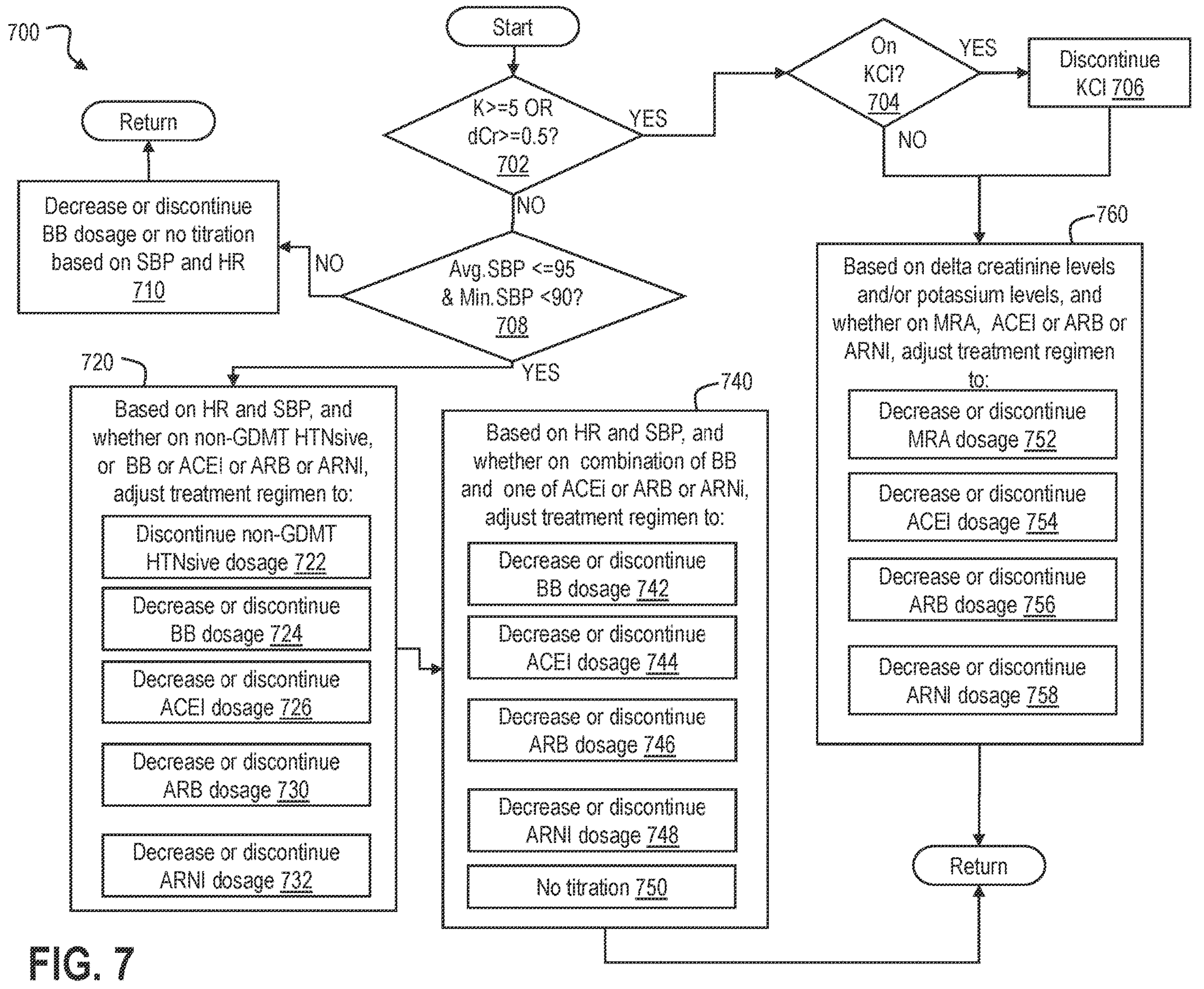
FIG. 7 shows a high-level flow chart of an example safety decision engine for managing a therapeutic regimen of a patient when the patient's stability is less than a stability threshold, and/or when monitoring a patient response to an updated therapeutic regimen, according to some implementations of the present disclosure.
Figure 8A:
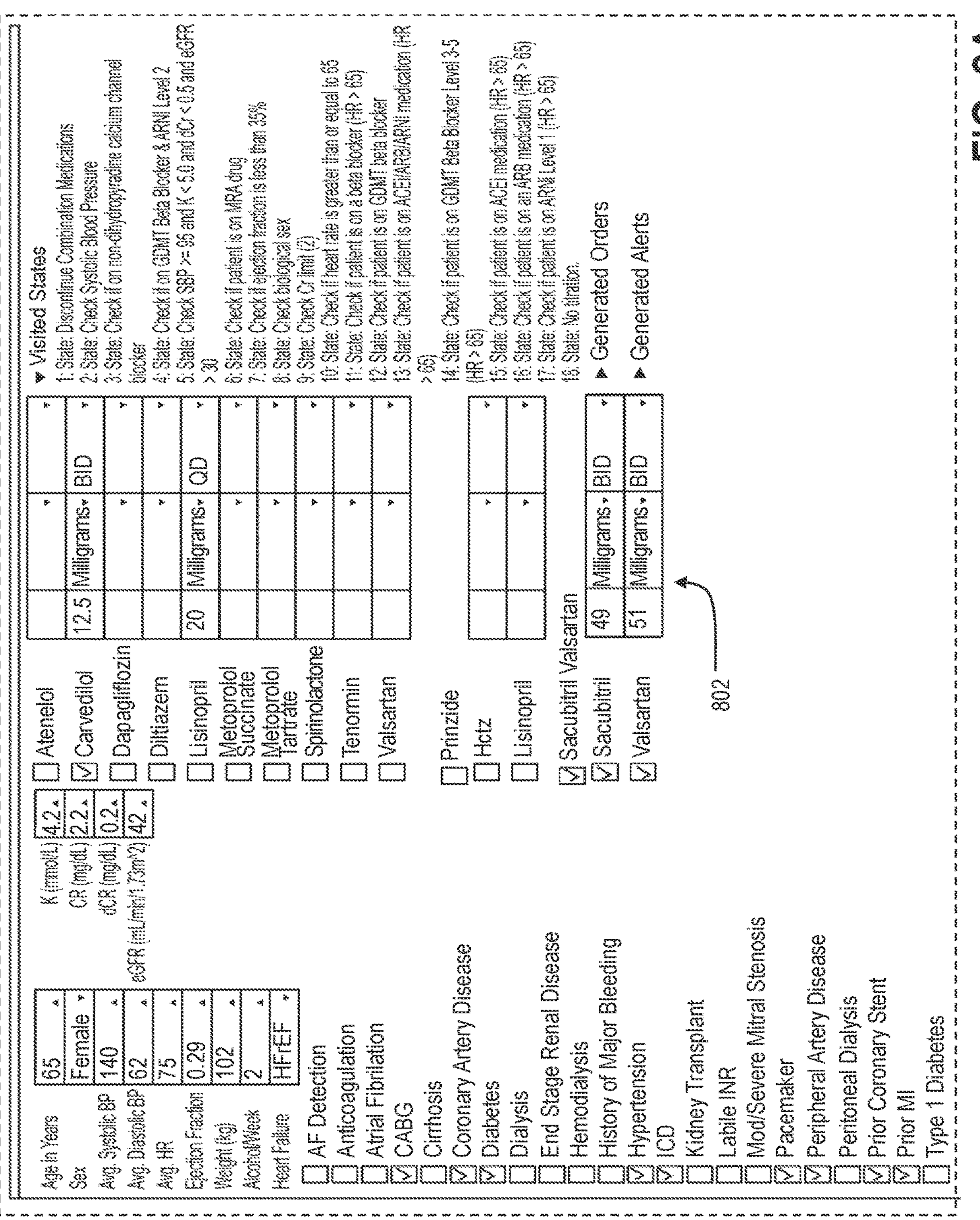
FIGS. 8A and 8B show example clinician interfaces including example patient data acquired from a health record of the patient, example recommendations/updates, and example alerts, according to some implementations of the present disclosure.
Figure 8B:
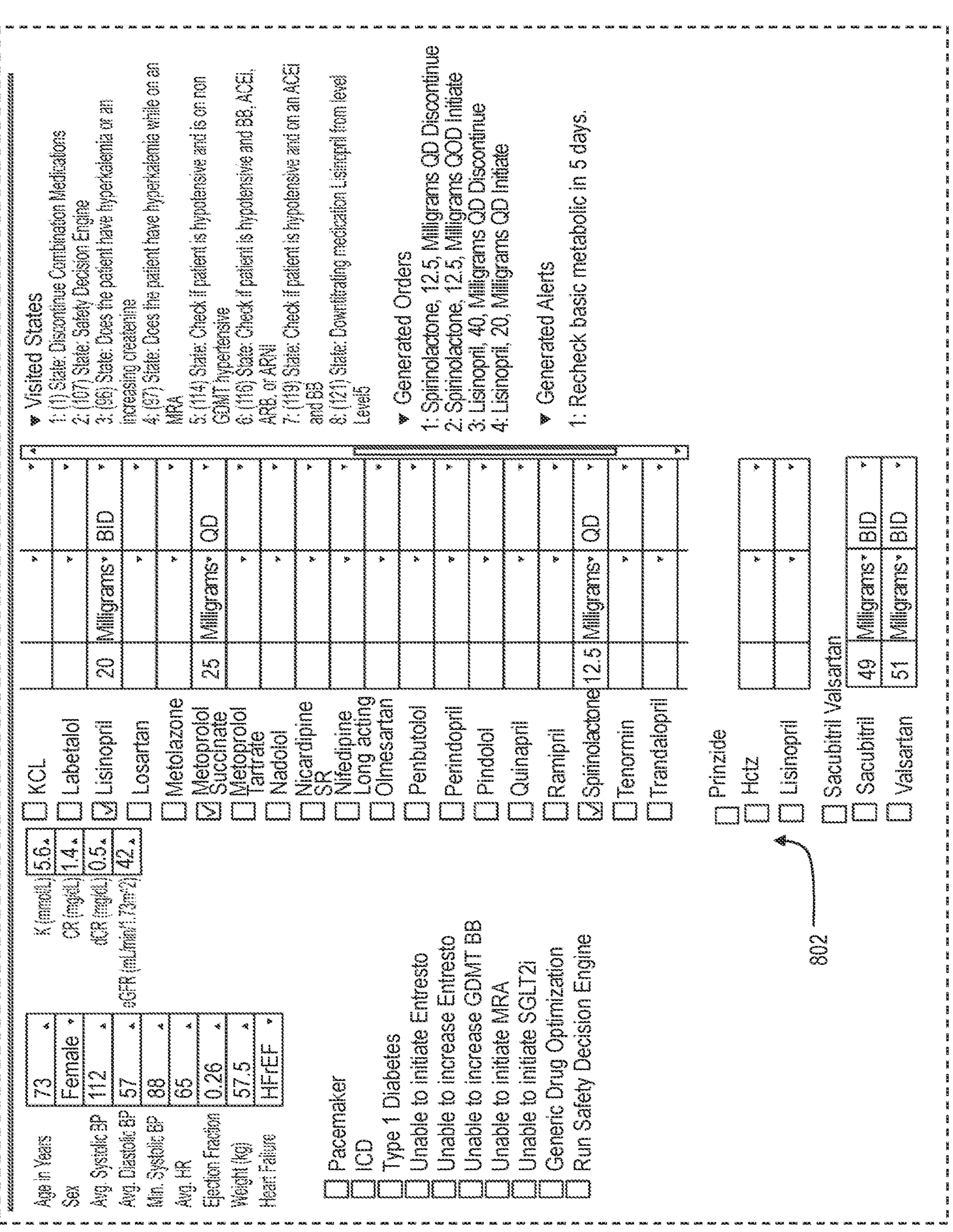

Nationally, guideline-directed medical therapy (GDMT) in patients with heart failure is underutilized. Fewer than one in four patients are treated on all three of the recommended classes of GDMT (angiotensin-converting enzyme inhibitor (ACEi)/angiotensin II receptor blocker (ARB), angiotensin receptor neprilysin inhibitor (ARNI), beta-blocker (BB), and mineralocorticoid receptor antagonist (MRA). Further, previous studies have shown that only 1% receive target doses of all 3 classes of medications. More recently, inhibitors of sodium-glucose cotransporter 2 (SGLT2i) have been found to also improve outcomes in HF patients. A major reason why GDMT is underutilized is due to clinical inertia, which occurs when clinicians fail to initiate or intensify evidence-based therapy or achieve prescribed targets in their patients (such as with blood pressure or blood sugar). Clinical inertia poses one of the greatest obstacles in improving clinical outcomes in HF patients. The methods and systems provided herein improve utilization of GDMT to achieve target doses of HF medications in a seamless and efficient manner while enabling monitoring of the patients to any medication update or change. Further, the methods and systems provide an evidenced-based approach utilizing physiological data output from one or more remote monitoring devices as well as patient health data from electronic health records to manage HF therapy. A decision-tree based model, referred to herein as decision engine, is implemented by a therapeutic regimen evaluation processing system for evaluation and management of therapeutic regimen for patients diagnosed with heart failure and undergoing treatment with one or more therapeutic agents for HF. An example method for managing a therapeutic regimen is shown at FIG. 2. Further, in some examples, remote patient monitoring data from the one or more remote monitoring devices are used to evaluate a patient's stability, and therapeutic regimen updates may be based on the patient's stability. In one example, a mode of operation of the decision engine may be based on the patient's clinical stability. An example method for determining the mode of operation of the decision engine is discussed at FIG. 3. Further, depending on whether the therapeutic regimen is being updated or whether a patient response to the updated therapeutic engine is evaluated, the desired mode of operation of the decision engine may be selected. An example method for updating a therapeutic regimen based on clinical stability and evaluating patient response to the updated regiment is shown and described at FIGS. 4A, 4B, and 5. Further, FIGS. 6A-6D describe an example decision-tree based approach that may be implemented in an initiation and dosing engine for up-titration, initiation, decreasing dosage or discontinuing a therapeutic agent. Further, one or more alerts to re-check laboratory tests may be provided. Further, FIG. 7 shows an example method that may be implemented in a safety decision engine to determine if one or more therapeutic agents that are currently prescribed to the patient is to be decreased in dosage or discontinues. In particular, the safety decision engine may check for thresholds related to symptoms of drug side effects, acute kidney injury, hyperkalemia, hypotension, and bradycardia using remote patient monitoring (RPM) data. If the RPM detects that the patient has met any critical safety thresholds, then the safety decision engine may update the therapeutic regimen to decrease or discontinue the dosage of one or more medications. In some examples, the safety decision engine may recommend that the patient either discontinue or decrease the dosage of a medication, and the therapeutic regimen may be updated accordingly. FIGS. 8A and 8B show example clinician-side interface of the decision engine. FIGS. 9A and 9B are tables showing example HF medications and associated dosage. FIGS. 10A, 10B, 11A, 11B, and 11C show example input, decision states, and output recommendations for various therapeutic regimen updates. FIGS. 12A, 12B, 13A, 13B, and 15A-15O show example methods for managing the therapeutic regimen of a heart failure patient, including initiating a heart failure digital therapeutics decision engine and providing follow-up care scheduling. FIG. 14 shows an example patient side processing for acquiring patient data (e.g., wearable data, home blood pressure data, medication adherence data, medication side effects data, medication tolerance data, etc.) and communicating patient data with the heart failure decision engine, for example to receive prescription initiation and/or updates, and to provide the acquired patient data to the decision engine.

The technical advantage of the methods and systems described herein includes improved patient therapeutic regimen monitoring and patient response monitoring outside clinical setting. Another technical advantage of the methods and systems described herein is safe and efficient initiation and up-titration of GDMT-based therapeutic agents, which allows the therapeutic regimen to achieve target doses efficiently and quickly. As a result, GDMT utilization is increased, which improves patient outcomes and reduces mortality risk. Further, patient response monitoring after an update to the therapeutic regimen allows effective monitoring of side-effects and enables quick response to adjust medication. The methods and systems described herein reduce clinician inertia. Yet another technical advantage is effective customization of HF therapy with quick and efficient pathway to achieve and manage target levels of HF medications based on current physiological conditions of the patient, including past medical history, and previous GDMT intolerances or allergies.

In this way, by leveraging data from remote monitoring devices, the electronic health record (EHR), and an application (e.g., to receive input from patient, instruct and/or educate patient regarding prescribed updates to medication, providing notification, etc.), the methods and systems described herein enables clinicians to personalize and optimize guideline directed medical therapy (GDMT) in patients with chronic heart failure (HF) and reduced ejection fraction (HFrEF). As a result, patient outcome is improved, and mortality risk and hospitalization in HF patients is reduced. Thus, the methods and systems described herein provides improvements in heart failure therapy.

Example System

FIG. 1 shows a block diagram of an example digital therapeutics system 100 that may be implemented for determining and/or updating a treatment regimen for patients diagnosed with a cardiovascular disease condition, such as heart failure. The treatment regimen may include one or more therapeutic agents and corresponding dosage for the one or more therapeutic agents for cardiovascular disease condition. The examples herein will be described with respect to heart failure (HF); however, it will be appreciated that similar systems and methods may be implemented for any cardiovascular disease condition or any health condition for which a therapeutic regimen including one or more therapeutic agents (e.g., medications) may be prescribed by a health care provider.

The digital therapeutics system 100 includes one or more physiological sensors 106 for acquiring physiological sensor data from a patient. Indications of physiological parameters from the one or more physiological sensors are input into decision engine 152 to provide more accurate and reliable patient health evaluation which is used to evaluate and/or manage a therapeutic regimen for a heart failure patient, as further discussed below.

In one example, the one or more physiological sensors 106 may be configured as remote monitoring sensors for monitoring one or more physiological parameters of the patient. The remote monitoring sensors may include one or more wearable sensors and/or devices, one or more non-wearable sensors and/or devices, or any combination thereof. Further, the one or more wearable sensors may be positioned directly or indirectly on human body. The one or more wearable sensors may be configured as body-worn devices such as wrist-worn devices (e.g., smart watch, wrist band, etc.), neck-worn devices (e.g., necklace, etc.), ear buds, rings, straps, etc., body adhering devices (e.g., wearable patch, device with multiple adhering modules), embedded devices in clothing (e.g., body suit, vest, pant), glasses, keychains, shoes, etc. Non-wearable sensors and/or devices may include but not limited to smart phones (including apps), hand-held devices, table-top blood pressure monitors, glucose meters, bed-side sleep monitors, etc.

The one or more physiological sensors 106 may include one or more of one or more blood pressure sensors 108 for acquiring blood pressure data, one or more photoplethysmogram (PPG) sensors 110 for acquiring PPG data, one or more electrocardiogram (ECG) sensors 112 for acquiring ECG data, one or more stability sensors 114 for acquiring patient mobility and/or stability data, and one or more audio sensors 116 for acquiring auscultation data. In some examples, the one or more physiological sensors 106 may additionally include other sensors 117, such as electromyogram (EMG) sensors, EEG sensors, temperature sensors, biochemical sensors, biomechanical sensors, and implantable sensors.

Blood Pressure Sensors

Hypertension or high blood pressure is a medical condition that increases the risks of cardiovascular diseases, and other diseases. Patients with hypertension may require periodic or continuous monitoring of blood pressure to prevent progression to heart failure. Further, blood pressure monitoring is also important in patients with established heart failure. Accordingly, in order to evaluate a therapeutic regimen for a HF patient, update the therapeutic regimen, and/or provide one or more alerts that facilitate continuous evaluation and/or update of the therapeutic regimen, blood pressure measurements are used. Accordingly, the one or more blood pressure sensors 108 may acquire blood pressure data from the patient, which is used to obtain blood pressure measurements, including ambulatory blood pressure measurement and/or standard blood pressure measurements. The one or more blood pressure measurements may include one or more of systolic blood pressure (SBP) and diastolic blood pressure (DBP). The one or more blood pressure sensors 108 may be configured as wearables or home-based monitoring devices. In one example, a patient may be trained and/or guided to perform home-based blood pressure measurement using a home-based blood pressure monitoring device. For example, the patient may be guided with regard to positioning of a blood pressure cuff of the home-monitoring device, and blood pressure data may be acquired via the home-monitoring device, which may automatically output one or more blood pressure measurements. In another example, when a blood pressure sensor is configured as a wearable device (e.g., a wrist watch), the blood pressure data may be automatically acquired and the blood pressure may be automatically calculated. In yet another example, data from a combination of sensors (e.g., ECG and PPG data) or data from another type of sensor (ECG data or PPG data alone) may be used for measuring SBP and/or DBP.

ECG Sensors

ECG monitoring may be used to estimate and/or measure various cardiac parameters, including but not limited to heart rate (HR), hear rate variability (HRV), heart rhythm abnormalities (QT interval changes, QRS irregularities, ST segment changes, etc.) atrial arrhythmias, and ventricular arrhythmias. The one or more ECG sensors 112 may acquire ECG data, which is used to determine one or more of heart rate and heart rhythm measurements of the patient. Further, the one or more ECG sensors may be configured to acquire single-lead, or multi-lead data (e.g., two-lead, three-lead, six-lead, ten-lead, 12-lead etc.) Furthermore, the one or more ECG sensors 112 may be configured as a wearable or non-wearable ECG monitoring device. In one example, a wearable ECG monitoring device including one or more ECG sensors may be worn by the patient or attached to a patient, and ECG data of the patient may be acquired via the wearable device in a continuous manner or at pre-determined intervals or in response to user initiation. In another example, a hand-held ECG monitoring device may be used to acquire ECG data. For example, depending on the device configuration, the ECG monitoring device may be placed at specific anatomical positions on the body in order to acquire multi-lead data.

PPG Sensors

A PPG sensor may include at least one light source, (e.g., an LED) and at least one photodetector (e.g., a photodiode). Using the photodetector, PPG signals indicative of blood flow through the vessels may be generated, which may be used for measuring and/or estimating one or more physiological parameters of the patient (e.g., heart rate, respiration rate, heart rate variability, pulsatile blood oxygenation estimate (SpO2), blood pressure, etc.). PPG sensors may be used in addition to or alternative to ECG sensors. PPG sensors may be configured as wearables or non-wearable devices, and may be placed at anatomical positions such as the earlobe and fingertip where the desired PPG signals are collected with higher quality.

Stability and/or Motion Sensors

Evaluation of patient stability (e.g., patient balance when in an upright stance, postural sway, etc) and patient mobility (e.g., changes in gait) may be performed using the one or more stability and/or motion sensors 112. In some embodiments, the patient mobility and/or stability evaluation may be used to determine a mode of operation of a decision engine for HF therapeutic regimen management as discussed in detail further below. Briefly, the patient mobility and/or stability evaluation may be performed via data acquired from one or more stability and/or motion sensors 112. In some examples, a mode of operation of the decision engine that may result in an initiation of a therapeutic agent or up-titration of a therapeutic agent may be based on whether or not stability evaluation indicates that the patient meets the desired stability thresholds. In some other examples if the stability of the patient is below a low threshold, the decision engine may be operated in a mode that may evaluate if one or more therapeutic agents may be discontinued or decreased or if one or more lab tests are required. Details of the different modes of the decision engine are discussed further below.

The one or more stability and/or motion sensors 112 may include one or more accelerometers and/or one or more gyroscopes. In one example, the inertial sensors embedded in smart devices can be used to measure patient stability and/or patient mobility. As a non-limiting example, data acquired from an accelerometer and/or a gyroscope included within a smartphone (e.g., iPhone), a smart watch (e.g., Apple watch) or a smart table (e.g. iPAD) may be used to evaluate stability of a patient. For example, data from the accelerometer and/or the gyroscope may be used to calculate an equilibrium score, which may indicate a degree sway of a patient. In some examples, a wearable device may include one or more accelerometers (e.g., a biaxial accelerometer, a triaxial accelerometer, etc) and/or one or more gyroscopes (e.g., a biaxial gyroscope, a triaxial gyroscope, etc.), which may be used to acquire stability data and evaluate a stability of a patient. Further, in some examples, the one or more stability and/or motion sensors 112 may be configured as an inertial measurement units (IMUs) comprising accelerometers, gyroscopes, and magnetometers. The IMUs may be placed on specified positions on the leg (e.g. shank, foot, etc), and data from the IMUs may be used to evaluate gait irregularities and/or stability.

Audio Sensors

In some examples, one or more audio sensors 116 may be used to evaluate heart sounds of the patient. The one or more audio sensors 116 may be used to perform auscultation, and audio data from the one or more audio sensors 116 may be used in the determination of whether to maintain or update a therapeutic regimen or generate one or more alerts (e.g., alerts to perform a specific lab test, perform basic metabolic panel, etc.).

Other Sensors

In some examples, data from other sensors, such as biochemical sensors and biomechanical sensor may be used in the evaluation and/or management of a therapeutic regimen for HF. Biochemical sensors include electrochemical transducers configured to measure body fluid electrolyte parameters, such as analyte concentrations. For example, sensors configured to analyze sweat, saliva, and/or hydration may be used. Biomechanical sensors, such as ballistocardiogram-based sensor, seismocardiogram-based sensors, and dielectric sensors, may be used to continuously measure variables such as cardiac output, lung fluid volume and weight. For example, an accelerometer placed on a patient's chest may be used to generate a seismocardiogram (SCG), which is a measure of thorax accelerations produced by the beating heart. Through the SCG, different mechanical events of the cardiac cycle including opening and closing of the aortic and mitral valves, atrial systole, and/or isovolumic contraction and relaxation, may be evaluated. Accordingly, in some examples, SCG data may be additionally used in evaluating and/or management of a therapeutic regimen for HF. Further, in some examples, data from one or more additional sensors such as EMG, EEG, temperature sensors, and/or implantable cardiac monitor (e.g., for AF detection, monitoring pulmonary artery pressure, etc.) may be used in the evaluation and/or management of the therapeutic regimen for HF.

In some examples, a multi-sensor module that includes a plurality of the physiological sensors may be used to acquire multi-sensor data from the various sensors simultaneously, and process the multi-sensor data to estimate and/or measure a plurality of physiological parameters (heart rate, systolic blood pressure, diastolic blood pressure, weight, temperature, stability, oxygen saturation, respiration rate, stability, etc.), which may be used as input parameters for a decision engine configured to evaluate and/or manage a therapeutic regimen for HF.

In some examples, one or more monitoring devices may be used to acquire physiological sensor data from a patient, where each of the one or more monitoring devices includes one or more physiological sensors 106. As a non-limiting example, a patient's physiological parameters may be estimated and/or measured using a first monitoring device that may be a blood pressure monitoring device, a second monitoring device that may be an ECG and/or a heart sound monitoring device; and a third monitoring device that may be a stability monitoring device. Physiological sensor data from each of the devices may be acquired sequentially or simultaneously within a desired time-window for evaluation and/or management of a therapeutic regimen for HF.

In some examples, data from some of the sensors may be acquired simultaneously. For example, data from sensors that generate waveform data may be acquired simultaneously and in a time-synchronized manner (e.g., ECG and audio sensors; ECG and PPG; ECG, audio, and PPG; ECG, PPG, and ECG; etc). Further, data from other physiological sensors, such as blood pressure sensor, may be acquired independently but within the desired time-window when sensor data for evaluation and management of a therapeutic regimen is acquired.

Further, in some examples, each of the one or more physiological sensors or each of the one or more monitoring devices (each of the one or more monitoring devices including one or more physiological sensors) may include an integrated processor that is integrated with a respective sensor (or device). The respective integrated processors may process the corresponding data acquired via the respective sensors and generate a corresponding output, which is then transmitted to the decision engine for determining whether any modification to a current treatment regimen may be performed.

In some examples, a computing device 120 may be communicatively coupled to the one or more physiological sensors (and/or monitoring devices) 106 and a therapeutic regimen evaluation server 150. Further, the computing device 120 may receive data from and send data to the one or more physiological sensors 106 a connection 118, which may be wired, wireless (e.g., WiFi, ZigBee, Bluetooth, 5G, etc.), or a combination thereof. Further, the computing device 120 may send data to and receive data to the server 150 via communication network 140, which may be wired, wireless, or a combination thereof. The computing device 120 may be any suitable computing device, including a computer, laptop, mobile phone, tablet, etc. The computing device 120 includes one or more processors 126, one or more memories 132, and a user interface 134 for receiving user input and/or displaying information to a user.

In one implementation, the computing device 120 may be configured as a mobile device and may include a patient-side application 136, which represents machine executable instructions in the form of software, firmware, or a combination thereof. The components identified in the application 136 may be part of an operating system of the mobile device or may be an application developed to run using the operating system. In one example, application 136 may be a mobile application. The application 136 may also include web applications, which may mirror the mobile application, e.g., providing the same or similar content as the mobile application.

In one example, the application 136 may include a patient interface and may assist a patient in acquiring physiological sensor data for evaluation and/or management of therapeutic regimen for HF, input estimates and/or measurements of one or more physiological parameters based on remote monitoring by the patient, and receive notifications and/or alerts from the decision engine. For example, through the application 136, a patient may receive notifications to initiate physiological sensor data acquisition for therapeutic regimen evaluation, input estimated and/or measured physiological parameter values for further processing via the decision engine 152, receive notification based on output from the decision engine regarding any updates to the therapeutic regimen, provide confirmation and/or acknowledgement of updates, input reactions to an updated regimen, and receive notification regarding pending and/or additional laboratory tests that may be required for evaluation and/or management of the therapeutic regimen, among other features.

In some examples, the patient may receive therapeutic regimen updates, recommendation, notifications, alerts, and other HF therapeutic regimen related information from the server through the application 136. Through the patient interface, the application 136 may (1) display vital signs, (2) display activity, (3) display a medication list, (4) display medication reminders, (5) therapeutic and dosage recommendations, (6) patient content including instructional videos, (7) enable input of side effects from patient, (8) enable therapeutic regimen notification/update/change confirmation, and (9) other HF therapeutic regimen related information.

In some implementations, the application 136 may be used to initiate physiological sensor data acquisition from the one or more physiological sensors 106 (and/or one or more monitoring devices) for evaluation and/or management of therapeutic regimen for HF. Further, in one example, the application 136 may be configured to receive physiological sensor data from the one or more physiological sensors 106 (and/or one or more monitoring devices), pre-process the physiological sensor data (e.g., apply filtering, normalizing to improve signal quality and reduce noise), and transmit the pre-processed sensor data to a therapeutic regimen server 150 (indicated by 144) for estimating and/or measuring one or more physiological parameters from the physiological sensor data. The estimated and/or measured physiological parameters (heart rate, stability, systolic BP, diastolic BP, etc) may then be used as input into the decision engine 152 for evaluation and/or management of the therapeutic regimen for HF.

In another example, respective physiological sensor data from the one or more physiological sensors 106 (and/or one or more monitoring devices) may be processed via respective mobile or web applications in the computing device 102 (and via respective application programming interfaces (APIs)), and the estimated and/or measured physiological parameter from the respective physiological sensor may be used as input to the decision engine 152. In one example, the respective physiological parameter(s) estimated and/or measured via each physiological sensor may be automatically transmitted to the decision engine 152. In another example, a user may input one or more estimated and/or measured physiological parameters via the application 136. In yet another example, the user may input some of the physiological parameters, while the remaining estimated and/or measured physiological parameters may be automatically input into the decision engine. In some examples, the computing device 102 may include one or more sensors (e.g., gyroscope 128, accelerometer 124, etc.) and raw or pre-processed data from the one or more sensors may be accessed via respective framework or APIs. For example, gyroscope and/or accelerometer data from the computing device 120 may be used to determine one or more stability parameters (e.g., degree of sway) of the patient, which may be input automatically (e.g., via application 136 to server 150 or from server 150 depending on how the raw or pre-processed data is processed to obtain the physiological parameter) to the decision engine.

In some examples, one or more physiological sensor datasets from the one or more physiological sensors 106 may be transmitted to the therapeutic regimen evaluation server 150 via the computing device 120 and/or a communication network 140, and a pre-processing step (e.g., to remove noise) may be performed at server 150 or at the computing device 102. Said another way, the server 150 may be configured to receive one or more physiological sensor datasets (raw or pre-processed) from the one or more physiological sensors 106 via the computing device 120 and/or the network 140. The network 140 may be wired, wireless, or various combinations of wired and wireless. Further, the one or more physiological sensors 106 may be pre-associated with the therapeutic regimen evaluation server 150. Further, in some examples, the one or more physiological sensors 106 may be a network of inter-connected devices pre-associated with the therapeutic regimen evaluation server 150.

In some examples, an intermediate gateway may be used to link the physiological sensors 106 with the server 150, and the server 150 may receive estimated and/or measured physiological parameter values via the intermediate gateway. In some other examples, the server 150 may interact with one or more respective platforms of the respective physiological sensors, and selected information, such as one or more physiological parameters estimated and/or measured using data acquired via the respective physiological sensor, may be received by the server 150 from the sensor platform. As a non-limiting example, a blood pressure monitoring platform may estimate and/or measure one or more of SBP and DBP of a patient based on data acquired via the blood pressure sensor 108, and the SBP and/or DBP value may be received by the server 150 from the blood pressure monitoring platform.

The therapeutic regimen server 150 includes one or more processors 149 and one or more non-transitory memories 151. The one or more processors 149 may include machine readable instructions stored in non-transitory memories 151. The one or more memories 151 may store a decision engine 152 for performing evaluation and/or management of a therapeutic regimen for a HF patient. In one example, the decision engine 152 includes a stability processing logic 153 for evaluating a stability of a patient. In some examples, stability of the patient may be evaluated periodically at desired intervals in order to determine whether to initiate an evaluation of a therapeutic regimen. In some other examples, stability of the patient may be evaluated to determine a mode of operation of the decision engine, as discussed further below.

The decision engine 152 further includes a safety decision engine 154 for determining whether one or more therapeutic agents (that is, medications) in a therapeutic regimen may be decreased or discontinued or whether another laboratory test may be needed for the patient. The decision engine further includes an initiation and dosage engine (IDE) 155 for determining updates to the therapeutic regimen, including initiation of new medications and an up-titration of one or more therapeutic agents. Accordingly, the updates to the therapeutic regimen based on IDE may also include maintaining current regimen, down-titration, or discontinuation of one or more therapeutic agents, and one or more alerts to perform one or more laboratory tests. Further, the updates to the therapeutic regimen may also include a follow-up care recommendation based on the updates, and/or follow-up care scheduling. In some examples, based on one or more patient conditions, the decision engine 152 may be operated in a first mode, wherein the IDE 155 is executed, or in a second mode, wherein only the safety decision engine 154 is executed. Details of the decision engine, including the different modes of operation of the decision engine will be discussed below.

In some implementations, the decision engine 152 may include an automated testing harness module (FIGS. 1B and 1C) for evaluating any updates to one or more thresholds, including one or more of medication dosage thresholds and patient parameter thresholds (e.g., potassium levels, delta creatinine levels, blood pressure levels). For example, during testing of the decision engine, one or more changes to the decision engine (e.g., changes in thresholds, changes in decisions to uptitrate, maintain, decrease, or discontinue a medication, etc.) may be evaluated using the automated testing harness. As one example, the automated testing harness may run the decision engine for a plurality of patient datasets (which may include information about labs, medications, medication tolerances, etc.) previously stored to evaluate the changes to the decision engine. In this regard, a plurality of simulations may be run using the plurality of patient datasets in order to determine initiation and dosing engine output changes and/or safety engine output changes caused by the changes made to the decision engine in order to determine whether or not the changes can be implemented in the decision engine when prescribed to a patient.

The automated testing harness can include an IOT database that stores the patient datasets, a decision engine referential database that stores various different versions of the decision engine and/or modules or portions of the decision engine, a decision engine output database where the validated version of the decision engine can be stored, and the clinician portal, where the validated version of the decision engine can be accessed. Thus, the automated testing harness is generally responsible for validating changes to the decision engine.

In some implementations, a physician may adjust thresholds during an initial set up of the decision engine for a current patient, and in response, the automated testing harness may run the plurality of simulations using previously stored patient profiles that are similar to the current patient to evaluate a clinician or physician set threshold prior to initiating the decision engine.

In some implementations, the automated testing harness may include a machine learning model configured to test one or more changes to the decision engine. The machine learning model may be trained using the plurality of patient datasets.

The decision engine 152 further includes an electronic health record (EHR) processing logic 156 for receiving patient information from an EHR system 162. The EHR system 162 includes an EHR server 166 and an EHR database storing patient health information. In some examples, the EHR system 162 may further include an EHR interface server (not shown) for interfacing with the therapeutic regimen evaluation server 150. In some examples, the decision engine 152 may be integrated within the EHR system 162. The decision engine 152 receives patient data from the EHR, via network 141, for example. Further, a clinician computing device 170 may be communicatively coupled to the therapeutic regimen evaluation server 150 via network 141. The network 141 may be a wireless network, a wired network, or any combination of wireless and wired networks.

The therapeutic regimen evaluation server 150 may include a cardiac health database 160 for storing therapeutic regimen information for each patient. The therapeutic regimen information may include a current therapeutic regimen, updates made to the current therapeutic regimen by the decision engine and/or the clinician, history of all therapeutic regimens prescribed to the patient, history of updates to each therapeutic regimen, information regarding accepted changes, information regarding prescription transmitted to pharmacy systems 190 etc.

The clinician computing device 170 includes at least one processor 176, at least one non-transitory memory 182, and a user interface 184, which may be a user input device. The user interface 184 may be a user input device, and may comprise one or more of a touchscreen, a keyboard, a mouse, a trackpad, a motion sensing camera, and other device configured to enable a user to interact with and manipulate data within the processing system 102. The user interface may include a display portion (not shown). The display may be combined with processor 176, non-transitory memory 182, and/or user interface 184 in a shared enclosure, or may be peripheral display devices and may comprise a monitor, touchscreen, projector, or other display device known in the art, which may enable a user to view patient sensor data, patient EHR data, and/or interact with various data stored in non-transitory memory 182, and/or database 160.

Further, the clinician computing device 170 may be a workstation communicatively coupled to the EHR system 162, via network 141, for example. The clinician computing device 170 further includes a clinician application 186. Similar to application 136 at the patient-side computing device 120, the clinician application 186 represents machine executable instructions in the form of software, firmware, or a combination thereof. Further, the components identified in the application 186 may be part of an operating system of the computing device 170 or may be an application developed to run using the operating system. Further, the application 186 may include a clinician interface that allows an authenticated clinician to prescribe, review, confirm, and/or make any changes to a therapeutic regimen. Further, the application 186 may allow an authenticated clinician to review a patient's EHR, input data from the EHR into the decision engine, and/or input patient monitoring data (e.g., from a clinical visit) into the decision engine. Further still, the application 186 may enable the clinician to selectively initiate therapeutic regimen evaluation by the decision engine 152 at any time. In one example, the clinician interface may (1) display vital signs of the patient, including physiological parameters estimated and/or measured using one or more physiological sensors (2) display relevant medical history, (3) display a medication list including dosage, (4) display generated orders, (5) therapeutic and dosage recommendations, (6) display alerts, (7) allow input of side effects from the clinician, and (8) display logic that caused the generated orders and/or alerts. Non-limiting examples of a clinician interface are shown at FIGS. 8A and 8B.

In one embodiment, an example system for implementing the disclosed technology may include a computing device with a display, a communications network, a patient, one or more remote monitoring sensors, and a server and associated database, where the server and the associated database are communicatively coupled to the computing device via the communications network. The computing device may be any suitable computing device, including a computer, laptop, mobile phone, etc. The network may be wired, wireless, or various combinations of wired and wireless. The server and the associated database may be local, remote, and may be combinations of servers and databases, or could be local processors and memory. The one or more remote monitoring sensors may be a smart phone, smart watch, smart ankle bracelet, smart glasses, smart ring, patch, band, or other device that suitably could be retained on the patient and output physiological parameter data from the patient. The physiological parameter data may include, but not limited to, heart rate data, blood pressure data, body temperature data, oxygen saturation data, respiratory rate data, patient balance stability data, and patient mobility data. In other examples, the remote monitoring device may be a clinical grade ECG system when a patient is in a hospital. In some examples, the remote monitoring device may be a camera on a mobile device and may record the heart rate data by fluctuation in colors of the capillaries detected by the camera.

In some examples, the decision engine may be executed during a remote clinical visit and/or prior to a remote visit with a clinician. In some other examples, the decision engine may be executed prior to a clinical visit.

FIG. 2 is a high-level flow chart illustrating an example method 200 for evaluation and/or management of a therapeutic regimen for a HF patient, according to an embodiment of the present disclosure. In particular, method 200 and all methods described herein may be implemented based on instructions stored in non-transitory memory of a processing system, such as a therapeutic regimen evaluation server 150, an edge device connected to the processing system, a cloud in communication with the processing system, or any combination thereof. The method 200 will be described with respect to FIG. 1; however, it will be appreciated that the method 200 may be implemented using similar systems without departing from the scope of the disclosure.

The method 200 begins at 202. At 202, the method 200 includes determining if entry conditions for performing a therapeutic regimen evaluation and/or management for a HF patient is met. The entry conditions may be based on one or more of a desired schedule for the patient. For example, one or more physiological parameters (e.g., systolic blood pressure, average systolic blood pressure, heart rate, average heart rate, etc.) and/or patient data (from EHR) may be monitored according to the desired schedule for the patient to determine if entry conditions are met. In one example, the patient may be monitored using remote monitoring data on a daily basis, and as such, the desired schedule may include a number of times a day, where the number of times may be 1, 2, 3, 4, 5, 6 or more times a day. In some examples, continuous monitoring of one or more physiological parameters may be performed. In some examples, the desired schedule may be every week, every 2 weeks, every 3 weeks, or every 4 weeks. In some examples, the entry conditions may be met when a new lab result is indicated in the patient's EHR. As such, method 200 may be iterative and may take into account periodic changes to the heart failure therapeutics, dosages, and/or times of administration (or other factors). In one example, the desired schedule may be specified by a clinician. In another example, the desired schedule may be automatically generated based on a cardiac health condition of the patient. Thus, in some examples, the desired schedule may be customized (either automatically or based on clinician recommendation) for each patient. Further, the entry conditions may be met if a new laboratory test result and/or a cardiac imaging result has been generated in the EHR. The laboratory may include a basic metabolic test or a comprehensive metabolic panel, and/or a complete blood count. Further, the cardiac imaging result may include a new echocardiogram indicating an updated left ventricular ejection fraction (LVEF), or any cardiac imaging result (e.g., nuclear profusion studies, Cardiac Single Photon Emission Computed Tomography, Cardiac Magnetic Resonance Imaging, etc.). In some examples, entry conditions may be met if an ejection fraction is less than 40% and/or a systolic blood pressure is greater than 140. If the entry conditions are not met, the answer at 202 is NO, and the method 200 proceeds to 204. At 204, the method 200 includes not initiating an initiation and dosing engine, such as the initiation and dosing engine 152 discussed at FIG. 1. Further details of the initiation and dosing engine will be described below at FIGS. 6A-6D.

If the entry conditions are met at 202, the method 200 proceeds to 210 and 220. At 210, the method includes receiving sensor data from the HF patient. In one example, the sensor data may include one or more physiological parameter values estimated and/or measured from data acquired via one or more physiological sensors, such as the one or more physiological sensors 106, pre-associated with the initiation and decision engine. In another example, the sensor data may include one or more datasets from the one or more physiological sensors. The one or more datasets may include raw or pre-processed data acquired via the one or more physiological sensors, and accordingly, in one example, the initiation and dosing engine may estimate and/or determine one or more physiological parameters based on the one or more datasets.

In some examples, the sensor data may include ECG data 212 (acquired via an ECG sensor), blood pressure data 214 (acquired via a BP sensor), stability data 216 (acquired via a gyroscope), and other sensor data 218, such as PPG, SCG, audio sensor data, etc. Alternatively, in some example, the sensor data may include a heart rate and/or an average heart rate over a threshold duration (estimated and/or measured based on one or more sensor data, such as ECG data and PPG data). The sensor data may further include an average SBP over the threshold duration, an average DBP over the threshold duration, and a minimum systolic BP estimated and/or measured over the threshold duration. The sensor data may further include a degree of stability calculated based on gyroscope data. In some other examples, the sensor data may include a combination of datasets. For example, raw or pre-processed to remove noise, etc may be received from some of the physiological sensors, while estimated and/or measured values may be received from the remaining physiological sensors. As a non-limiting example, the average SBP value, the average DBP value, and the minimum DBP value, determined at a remote blood pressure sensor may be received while ECG dataset and gyroscope dataset may be received from the ECG sensor and the gyroscope. Accordingly, the processing system (e.g., server 150) may determine the average heart rate and a degree of stability of the patient using the ECG and gyroscope datasets received from the respective sensing devices.

In one example, responsive to the entry conditions being met, an indication may be transmitted to a patient computing device (e.g., computing device 120) or automatically generated via an application (e.g., app 136) running at the patient computing device. The indication may include a notification and/or associated instructions for acquiring one or more sensor data from the one or more physiological sensors. In some examples, the patient may automatically initiate acquisition of data from the one or more physiological sensors via the application (that is, the patient interface of the decision engine). Additionally, when data acquisition is desired from a non-wearable device, such as a table top blood pressure monitor, a time window may be provided within which the patient may acquire all the necessary physiological sensor data. In some examples, when the one or more physiological sensors are configured as wearables and are engaged with the patient, and when the one or more physiological sensors are configured as network of interconnected medical devices, the acquisition of sensor data may be automatically initiated (either via patient initiating automatic acquisition from all interconnected sensors through the application (e.g., via a single click) or automatically initiated without patient initiation) responsive to the entry conditions being met.

In some instances, the method 200 may include receiving periodic sensor data readings, including a heart rate every 5 seconds, every 30 seconds, every minute, every five minutes, every hour, every day or other suitable times, including in-between the recited timing. Therefore, averages of sensor readings may be determined over longer time periods, without a patient consciously measuring the heart rate at their chosen times.

Simultaneously, at 220, the method 200 includes receiving patient data referenced to a specific patient profile in a memory, database, or other suitable storage system (e.g., EHR). The patient data may include therapeutics and dosages 222, height and weight 224, medical history 226, ejection fraction 228, side effects 230, and other data. In some examples, the therapeutics and dosages 222 may include a history of heart failure therapeutics administered to the patient, the dosages, and the accompanying sensor data 210 and side effects for particular therapeutics and dosages. Furthermore, the medical history may contain various information about conditions of the patient and other relevant information to heart failure conditions.

Various side effects 230 may be entered by the patient through an interface (e.g., application 136 at FIG. 1) and/or may be monitored by the sensors and detected from the sensor data 210. For instance, the initiation and dosage engine may detect cardiac events from the electrocardiogram data 212, heart rate changes that are outside acceptable thresholds, or blood pressure changes that are outside acceptable thresholds. Other qualitative side effects may be entered by the patient including nausea, dizziness, tiredness and others. In some examples, the patient will be prompted at regular time intervals to check or enter any side effects they are experiencing (including from a standard list).

In this way, data from one or more remote monitoring devices, such as remote blood pressure monitoring device, a wearable smart watch, etc., which may include electrocardiogram and/or pulse and activity data, may be input into the initiation and dosage engine. Furthermore, data may be input into the initiation and dosage engine from an electronic health records system. For instance, the sensor and the EHR data may be input into the initiation and decision engine to evaluate and/or output an updated therapeutic regimen. The information from the electronic health records system may include the various patient data including (1) basic metabolic information such as potassium, creatinine, delta creatinine, estimated Glomerular Filtration Rate (eGFR), etc., (2) height and weight, (3) therapeutic history (past and present), (4) active and past conditions, (5) surgical history, (6) ejection fraction data, (7) drug allergies, and (8) other information.

Next, at 232, the sensor data (from 210) and the patient data (from 220) may be input into the initiation and dosage engine and processed to output an updated treatment regimen 234 that may include at least one therapeutic or more and accompanying dosages 236. The initiation and dosage engine (IDE) may include decision trees that utilize threshold values for various physiological parameters. In one example, IDE may utilize, physiological sensor data, including average heart rate, average systolic blood pressure, minimum systolic blood pressure, respiratory rate, oxygen saturation, and temperature. and stability information from gyroscope, received as input from the one or more physiological sensors (or one or more remote monitoring devices including one or more physiological sensors), and may utilize patient data (e.g., such as metabolic panel data resulting from lab tests, cardiac imaging etc.) including potassium level, creatinine level, delta creatinine level, eGFR level, ejection fraction level etc., from the EHR. Respective threshold values or ranges for one or more of the above-mentioned physiological sensor data and patient data may be initialized at the time of prescription of the IDE or updated at any time during the course of the therapeutic regimen. For instance, the system may determine whether to titrate or change medication if average heart rate for an extended period of time (e.g. four hours) is over a certain level. Details of the initiation and dosage engine is discussed below at FIGS. 6A-6D.

After the updated treatment regimen is determined, at 238, the method 200 includes treating the patient by administering the therapeutics and dosages to the patient required by the updated treatment regimen. In some examples, this may include prescribing the therapeutic to the patient and requiring the patient to take the drug at certain intervals with certain dosages (e.g. 12 mg every 12 hours).

Next, in some examples, the sensors may monitor the patient after administration of the new treatment regimen, and the new data may be processed again by the initiation and dosage engine at a later time (e.g. for n number of times daily (where, n=1, 2, 3, 4), 1 week, 2 weeks, 3 weeks, 4 weeks, etc.) or may be continuous for a desired patient response monitoring period after the therapeutic regimen has be updated and the patient has begun to implement the updates.

Figure 3:
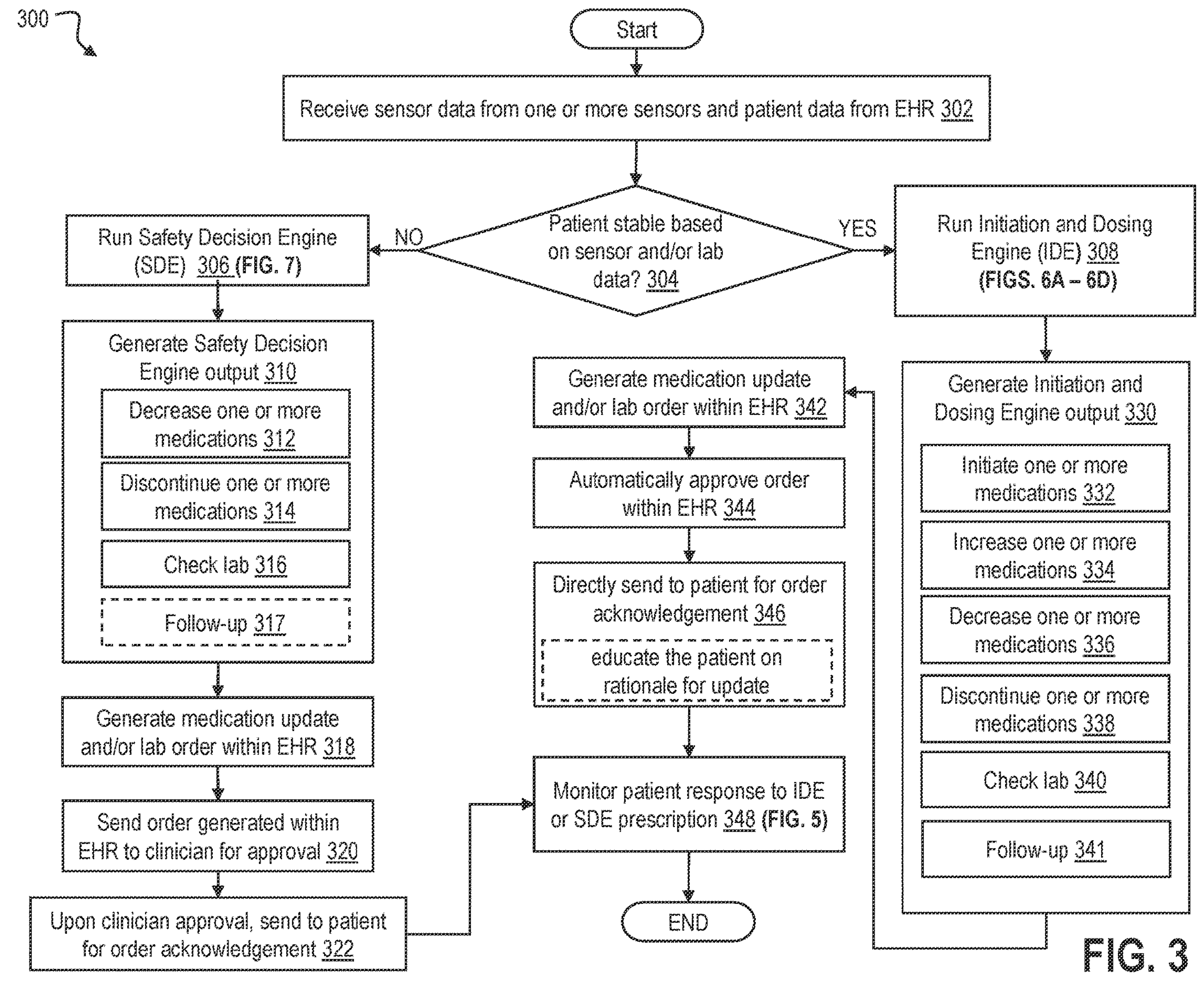
FIG. 3 shows a high-level flow chart of an example method for managing a therapeutic regimen of a patient based patient stability, according to some implementations of the present disclosure.

Turning to FIG. 3, it shows a high-level flowchart illustrating an example method 300 for operating a decision engine for evaluation and/or monitoring of a therapeutic regimen of a HF patient, according to an embodiment of the present disclosure. In particular, the method 300 may determine a mode of operation of a decision engine, such as decision engine 152, based on input from one or more physiological sensors, such as one or more physiological sensors 106, and from the patient's EHR, such as EHR system 162.

The method 300 begins at 302. At 302, the method 300 includes receiving input from one or more physiological sensors and the patient's EHR. Input from the one or more physiological sensors may include one or more physiological parameters estimated and/or measured using data acquired via the one or more physiological sensors. Details of the input from the one or more physiological sensors and the EHR are discussed above with respect to step 210 and step 220 at FIG. 2, and will not be repeated for the sake of brevity. Briefly, the one or more physiological parameters may include, but not limited to, average heart rate, heart rate variability, average SBP, average DBP, minimum SBP, current weight, a degree of stability, clinical stability, respiratory rate, oxygen saturation, and temperature. Further, the patient data from the EHR may include, but not limited to, presence of implanted devices (e.g., ICD, pacemaker), current and past health conditions (e.g., diabetes, hypertension), medication intolerance, sex, weight, creatinine level (Cr), change from previous creatinine (dCr), potassium levels (K), eGFR value (eGFR), current therapeutic agents (that is, medications) and their corresponding dosage.

Further, in some examples, some of the physiological parameters, such as systolic blood pressures and heart rate readings remotely monitored via respective physiological sensor and/or remote monitoring devices may be averaged through a specified monitoring period. The monitoring period may be 5 seconds, 30 seconds, one minute, five minutes, 30 minutes, 1-24 hours, 1-6 days, 1-2 weeks, or other suitable times, including in-between the above-mentioned timings.

Next, at 304, the method 300 includes determining if the patient is stable for up-titration or initiation of one or more medications. In one example, stability may be determined based on remote monitoring data over a stability monitoring duration. In particular, the clinical stability may be based on average heart rate (e.g., determined based on one or more of ECG data and PPG data), average systolic blood pressure (e.g., determined based on blood pressure data), average respiratory rate (e.g., determined based on PPG data), average oxygen saturation (e.g., determined based on PPG data), and average temperature (e.g., determined based on body temperature data). Further, in some examples, a degree of stability may be determined with respect to one or more of a standing posture, walking steadiness, step length, walking speed, walking asymmetry, and indications of syncope.

In some examples, the clinical stability may be determined based on a clinical stability score greater than a threshold score, the clinical stability score determined based on the average heart rate, average systolic blood pressure, average respiratory rate, average oxygen saturation, average temperature, and degree of stability, each compared to respective thresholds or respective threshold ranges.

In some examples, the stability may be confirmed based on each of the clinical stability parameters (that is, the average heart rate, average systolic blood pressure, average respiratory rate, average oxygen saturation, average temperature, and degree of stability) remaining within respective thresholds or threshold ranges during the stability monitoring period. In some other examples, two or more stability parameters may be used for stability monitoring. That is, two or more of the average heart rate, average systolic blood pressure, average respiratory rate, average oxygen saturation, average temperature, and degree of stability may be used for stability evaluation. As a non-limiting example, the average heart rate and average systolic blood pressure may be used for stability monitoring. For example, clinical stability may be confirmed based on the average heart rate and the average systolic blood pressure remaining within respective threshold ranges. As another non-limiting example, additionally or alternatively to the average heart rate and average systolic blood pressure, the degree of stability based on gyroscope and/or accelerometer data may be taken into account for stability monitoring. In some examples, stability indication may be obtained from a wearable, such as a smart watch, configured to calculate one or more a standing posture, walking steadiness, step length, walking speed, walking asymmetry, and indications of syncope. In some examples, indications from patient may also be taken in to account in determining stability. For example, a patient may indicate, via a patient-side application (e.g., app 136), regarding one or more stability-related conditions, such as dizziness, light-headedness, fainting etc. Accordingly, the processor may assess patient stability taking into account patient provided stability input.

If stability is confirmed, the answer at 304 is YES, and the method 300 proceeds to 308. At 308, the method includes running the initiation and dosing engine, which also includes the safety decision engine. The initiation and dosing engine may automatically initiate, discontinue, and/or update (increase or decrease) a dosage of one or more therapeutic agents based on guideline directed medical therapy (GDMT) using a patient's remote monitoring device data (that is, data from one or more physiological sensors) and the EHR data. Details of the initiation and dosage engine is described with respect to FIGS. 6A-6D below.

Upon running the initiation and dosing engine, the method 300 proceeds to 330. At 330, the method 300 includes generating an initiation and dosing engine output. The output includes recommendations to maintain a current therapeutic regimen or update the current therapeutic regimen. In one example, updating the current therapeutic regimen may include performing one or more of initiation of one or more new therapeutic agents (332), discontinuation of (338) or change in dosage of one or more previously administered therapeutic agents (that is, change in dosage of one or more therapeutic agents that are currently prescribed and taken by the patient) and re-check laboratory and/or imaging test (340) (e.g., basic metabolic profile, recheck LVEF, eGFR, etc.). The change in dosage of the one or more previously prescribed therapeutic agents may include increasing (334) or decreasing (336) dosages associated with the therapeutic agents. Each of the one or more new therapeutic agents and each of the one or more previously administered therapeutic agents may be selected from the group consisting of beta blockers, Angiotensin-converting enzyme (ACE) inhibitors, angiotensin receptor blockers (ARBs), Angiotensin receptor-neprilysin inhibitors (ARNis), Aldosterone receptor antagonists (MRAs), Sodium-glucose transport protein (SGLT2) inhibitors, and other therapeutic agents for treating heart failure. In some examples, each therapeutic agent may be selected from the group consisting of Bisoprolol, Carvedilol, Metoprolol Succinate, Captopril, Enalapril, Fosinopril, Lisinopril, Perindopril, Quinapril, Ramipril, Trandalopril, Candesartan, Losartan, Valsartan, Olmesartan, Sacubitril/Valsartan, Spironolactone, Eplerenone, Dapagliflozin, Empagliflosin, Canagliflozin, Ertugliflosin, and other therapeutic agents for heart failure therapy.

In one example, the check lab output may be generated responsive to one or more of a potassium level greater than a potassium level threshold, a delta creatinine level greater than a delta creatinine level threshold, initiation of an MRA class of therapeutic agent, initiation of an Angiotensin-converting enzyme (ACE) inhibitor, initiation of an angiotensin receptor blocker (ARBs), and initiation of an Angiotensin receptor-neprilysin inhibitors (ARNis).

Next at 342, the method 300 includes generating a medication update and/or a lab order within the EHR based on the initiation and dosing engine (IDE) output. In particular, generating a medication and/or lab order within the EHR may include automatically approving the order. In this way, if the patient had been determined to be clinically suitable for up-titration or initiation of one or more therapeutic agent, additional clinician review is not required (unless indicated by the clinician at the time of prescribing the therapeutic regimen evaluation and/or management).

Next, at 344, the method 300 includes transmitting the generated medication update and/or lab order to the patient's EHR. Upon transmitting, the method 300 proceeds to 346, at which a notification is sent to the patient (e.g., via patient interface of app 136) for acknowledgement. In particular, notification regarding the medication update and/or a lab order generated by the IDE may be directly sent to the patient without waiting for clinician review. In one example, once prescribed by the clinician, the initiation and dosing algorithm may initiate and change medical dosages without the input of a clinician within certain pre-specified blood pressure, heart rate, and laboratory parameters, as further discussed below at FIG. 4. Further, the notification to the patient may include links to one or more videos or slide-shows to educate patients on the importance of taking the recommended therapeutic regimen at the recommended doses, enabling patients to not only understand the rationale for recommendations, but also advocate for improved treatment for themselves. At any time, the patient may have access to the relevant videos and/or slide shows providing education regarding the specific therapeutic agent.

Additionally, the clinician may be notified (e.g., via clinician interface of app 186) regarding the medication update and/or lab order generated by the IDE. The clinician interface may include a decision engine worksheet that indicates the IDE output and the logic behind the DE output. For example, for each recommendation provided by the IDE, the decision conditions visited (also referred to herein as states) and the logic behind the decision condition is displayed to the clinician. An example clinician interface showing the states visited by a decision engine is shown at FIGS. 8A and 8B. The clinician interface may also display, for each run of IDE, one or more therapeutic agent orders generated, and one or more alerts generated (e.g., recheck metabolic lab in 5 days).

If no update and no lab order are generated, the patient and the clinician may be notified that the IDE was executed and no changes are required at this time and the patient may continue the current medication without any changes. Upon confirmation or acknowledgement by the patient regarding the medication update and/or lab order, the method 300 includes monitoring the patient response to IDE prescription, such as side-effects arising from the medication update. Details of monitoring the patient for side-effects will be described below at FIG. 5.

Figure 5:
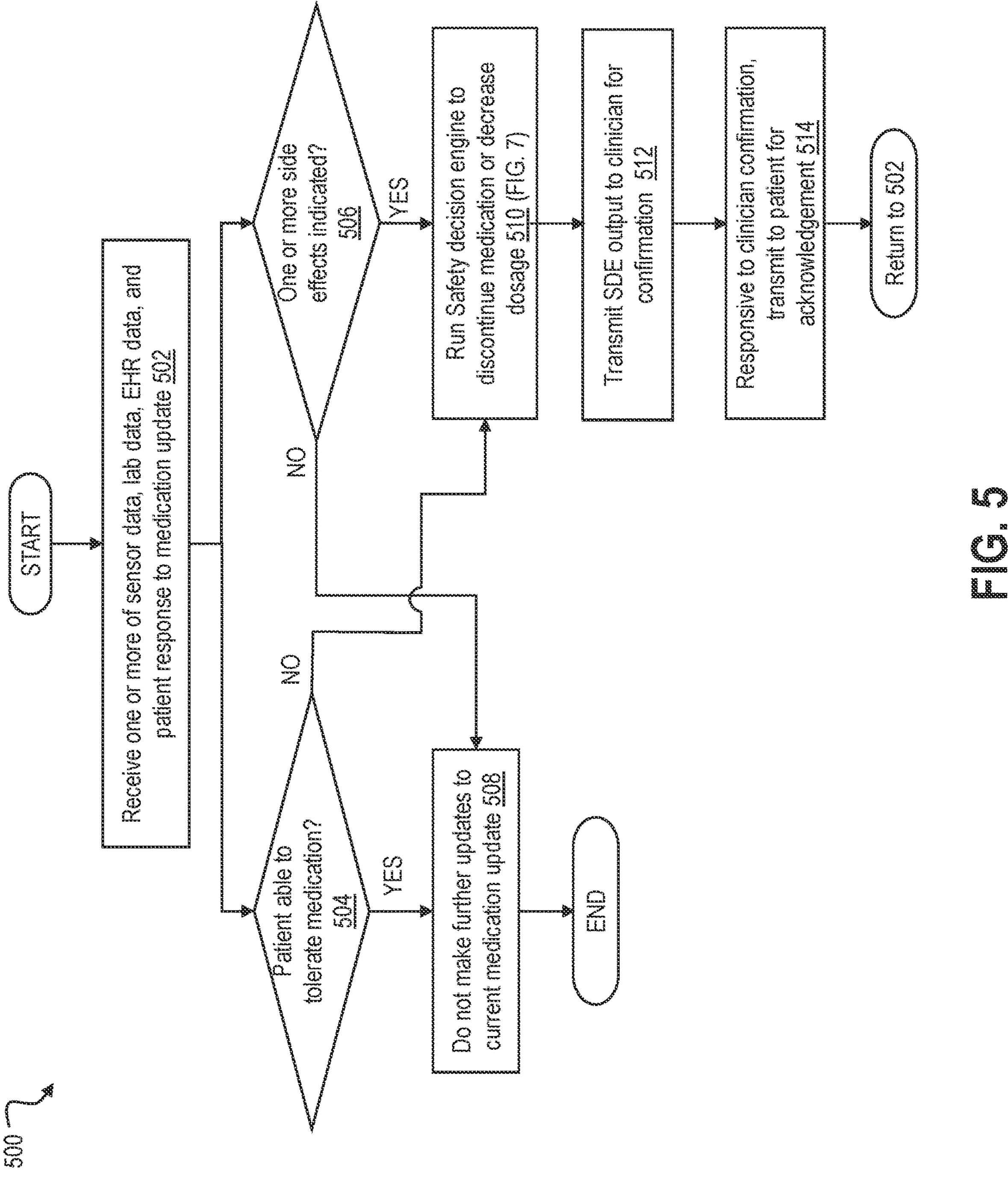
FIG. 5 shows a high-level flow chart of an example method for updating a therapeutic regimen based on patient response, according to some implementations of the present disclosure.

Referring to FIG. 5, it shows a flow chart illustrating a high-level method 500 for monitoring patient response after a therapeutic regimen is updated. In particular, when the decision engine, such as the initiation and dosing engine or the safety decision engine, for evaluation and/or management of a therapeutic regimen generates a prescription within the EHR, and is acknowledged by the patient, the patient response is monitored using one or more remote monitoring devices, such as one or more physiological sensor 106, and/or one or more indication from the patient, for a threshold post-prescription monitoring period (also referred to as patient response monitoring period). In one example, the threshold post-prescription monitoring period may be based on the type of medication updated and/or medical history of known side-effects and/or medication intolerances of the patient.

Method 500 begins at 502. At 502, the method 500 includes receiving a response from the patient. In one example, remote monitoring data from one or more remote monitoring devices may be used to automatically evaluate a patient's response to the therapeutic regimen update. For example, after the patient has started the updated therapeutic regimen, remote monitoring data acquired over the post-prescription monitoring period may be used for patient response analysis. In another example, a questionnaire may be generated based on the medication update by the IDE or SDE, and transmitted to the patient (e.g., via app 136). Upon starting the updated therapeutic regimen, the patient may perform a self-evaluation or with help from a care giver, provide responses to the question via the patient interface of the patient-side app. In view of the above, receiving the response from the patient may include one or more of receiving remote monitoring data from one or more remote monitoring devices and receiving response to the questionnaire.

Next, method 500 proceeds to 504 and 506. At 504, the method 500 includes determining if the patient is able to tolerate the medication update, and at 506, the method 500 includes determining if the patient is experiencing any side-effects. In one example, the method 500 may determine that the patient is able to tolerate the medication update and that there are no side-effects if one or more physiological parameters (e.g., heart rate, SBP, oxygen saturation, temperature, respiration rate, degree of stability, etc.) are within respective thresholds and/or threshold ranges over the post-prescription monitoring period and if no side-effects or intolerances are indicated the questionnaire by the patient. Further, in some examples, after initiation of one or more medications (e.g., MRA, ACEi, ARB, ARNi), the decision engine may generate a check lab output. Accordingly, if a lab result is indicated in the patient's health record referenced to the patient, the method 500 may monitor patient data from the EHR as well to evaluate whether the patient is able to tolerate the therapeutic regimen update (e.g., initiation of a medication) based on the lab result.

If the patient is able to tolerate the medication update (that is, if the answer at 504 is YES) and if there are no side-effects to the medication update (that is, if the answer at 506 is NO), the method 500 ends without making any further changes to the latest therapeutic regimen update. However, if the answer at 504 is NO or if the answer at 506 is YES, the method 500 proceeds to 510.

At 510, the method 500 includes running the SDE to determine if one or more medications may be discontinued or if the dosage may be decreased to improve tolerance to the medication update and/or reduce side effects. The method 500 further includes generating an SDE output within the EHR. That is, a second update to the therapeutic regimen may be generated. Next, at 512, the SDE output generated within the EHR is confirmed by the clinician. Upon clinician confirmation, at 514, the SDE output is sent to the patient for acknowledgement. Further, after patient acknowledgement, the SDE output (that is, the second prescription update) made to the therapeutic regimen is automatically sent to the pharmacy. The method 500 returns to 502 for another post-prescription monitoring period.

In this way, a HF patient is monitored after a therapeutic regimen update, and if needed, additional updates to the therapeutic regimen are provided until the patient is able to tolerate the therapeutic regimen with reduced side-effects.

Returning to 308, if the stability is not confirmed, the method 300 proceeds to 306. In one example, if stability is not confirmed, the method 300 may include evaluating if the clinical stability is above a second lower threshold. If the answer is YES, then the method 300 may proceed to 306; otherwise the method 300 may end and one or more indications regarding a failed attempt to update the therapeutic regimen may be provided to the patient and the clinician.

At 306, the method 300 includes running the safety decision engine, where a therapeutic agent may be discontinued or decreased. For example, the safety decision engine may monitor for symptoms of drug side effects, acute kidney injury, hyperkalemia, hypotension, and bradycardia. If the data from the remote patient monitoring devices indicates that the patient has met any critical safety thresholds, then the SDE will recommend that the patient either discontinue or decrease the dosage of one or more medication (GDMT or non-GDMT medications). Details of the safety decision engine will be described with respect to FIG. 7.

Next, at 308, the method 300 includes generating a safety decision engine (SDE) output. The SDE output includes maintaining a current therapeutic regimen or updating the current therapeutic regimen to decrease one or more previously administered therapeutic agent (310) (GDMT or non-GDMT based therapeutic agents) or discontinue one or more previously administered therapeutic agents (312) (GDMT or non-GDMT based therapeutic agents), and/or re-check laboratory test (314) (e.g., basic metabolic profile, eGFR testing, cardiac imaging, etc.).

In one example, the re-check laboratory test output may be generated responsive to one or more of a potassium level greater than a potassium level threshold, a delta creatinine level greater than a delta creatinine level threshold, initiation of an MRA class of therapeutic agent, initiation of an Angiotensin-converting enzyme (ACE) inhibitor, initiation of an angiotensin receptor blocker (ARBs), and initiation of an Angiotensin receptor-neprilysin inhibitors (ARNis).

Upon generating the SDE output, at 318, the method 300 includes generating the medication update and/or lab order within the EHR. In this case, since SDE was executed, the medication update and/or order within the EHR may be reviewed and approved by the clinician (that is, the medication updates and/or lab orders resulting from SDE alone are reviewed and approved by the clinician). Accordingly, at 320, the method 300 includes transmitting the generated medication update and/or lab order from the SDE to the clinician for approval. Upon receiving clinician approval, the method 300 proceeds to 322. In some examples, under certain conditions, such as systolic blood pressure within a threshold SBP range, and/or heart rate within a threshold heart rate range, the output of the safety decision engine (that is, the updated therapeutic regimen) may be automatically approved and the method may proceed from 318 to 322. In some examples, other physiological parameters, such as respiration rate, oxygen saturation, and/or temperature may be taken into account in determining whether the updated regimen is automatically approved or not. At 322, the method 300 includes transmitting a notification to the patient (e.g., via patient interface of app 136) for acknowledgement. The notification may include an indication that only an SDE was executed and that the medication update and/or the lab check order was reviewed and approved by the clinician (or automatically generated responsive to one or more conditions being met as discussed above). The method 300 then proceeds to 348 to monitor patient response to the SDE prescription, details of which are discussed above at FIG. 5.

In this way, integration of data from wearables enables automatic decision making when stable, and also enables clinicians to make GDMT decisions when stability levels are lower based on greater amounts of data than are available from a single in-office visit. Further, continuous remote monitoring during dose titration ensures that medications are initiated or changed when the patient is stable and monitors patients for medication side effects so that they can be quickly detected. Further, clinical scenarios where automatic initiation or up-titration is not possible are also identified. In these cases, the safety decision engine is executed to determine if any discontinuation or decrease is needed and where the clinician will need to make the final decision.

Further, remote monitoring of and remote therapeutic regimen modulation enables clinician outreach to distant areas where repeated visits to a clinic may not be more challenging. Further still, therapeutic management through integration of remote monitoring devices, EHR, and/or patient response reduced patient fatigue, which may further improve patient outcome. Further still, when implemented during or prior to a clinician visit (remote or in-person), the therapeutic management methods and systems described herein improves time available for clinician-patient interaction.

In one embodiment, a clinician prescribes the use of a digital therapeutic decision engine for evaluation and/or management of a therapeutic regimen for a heart failure patient. Prescribing the use of the digital therapeutic decision engine may include setting threshold ranges and/or threshold values for the various physiological parameters (e.g., average heart rate, average SBP, minimum SBP, stability, etc.) and/or various parameters that are obtained by lab and/or imaging tests (e.g., potassium level, delta creatinine level, eGFR level, LVEF percentage, etc.). In some examples, based on a cardiac health condition of a patient which may be based on the patient data (age, sex, BMI, etc) and medical history of the patient, the threshold range and/or threshold values at the time of the prescription may be automatically set.

Further, upon prescription of the digital therapeutic decision engine, based on input from EHR and remote monitoring devices (e.g., wearable devices and/or non-wearable devices), the decision engine may determine whether a patient is clinically stable enough for a change in his or her medications. If the patient is clinically stable, the decision engine determines if clinician input is required and if not, the decision engine automatically provides recommendation to initiate one medication at a specific dosage or increase dosage of one medication and/or automatically discontinue or decrease dosage of a medication and/or check labs. If the decision engine either initiates or increases the dosage of a medication in the therapeutic regimen, the patient app may (1) educate the patient on the rationale for the decision and (2) ask for the patient's acknowledgement. Once approved and the medication change has been made, data from the wearable devices and patient questionnaires is embedded in the patient app and will be used to monitor the patient for any adverse medication side effects over a patient response monitoring period. Continuous remote monitoring during dose titration ensures that medications are initiated or changed when the patient is stable and monitors patients for medication side effects so that they can be quickly detected. If any adverse side effects are detected, a safety decision component of the decision engine may be executed, where the safety decision component provides recommendations to discontinue or decrease the dosage of a specific medication pending patient's consent either automatically or with clinician input based on pre-specified parameters.

In another embodiment, a system comprises one or more physiological sensors configured to acquire a set of physiological sensor data from the patient; a processing system comprising at least one processor communicably coupled to at least one non-transitory memory storing a decision engine, the at least one non-transitory memory storing executable instructions that when executed causes the processor to: acquire the set of physiological sensor data from the one or more physiological sensors; acquire a set of patient data from an electronic health record system communicatively coupled to the processor, the electronic health record system storing patient data referenced to the patient, the patient data including one or more therapeutic agents and associated dosages; during a first condition, when a stability of the patient is above a first threshold, process the set of physiological sensor data and the set of patient data according to a first mode of operation of the decision engine and output a first updated therapeutic regimen based on an initial therapeutic regimen, the initial therapeutic regimen including the one or more therapeutic agents and associated dosages; and during a second condition, when the stability of the patient is below the first threshold, process the set of physiological sensor data and the set of patient data according to a second mode of operation of the decision engine and output a second updated therapeutic regimen based on the initial therapeutic regimen. In one example, processing according to the first mode of operation of the decision engine includes running the initiation and dosing engine, and processing according to the second mode of operation includes running the safety decision engine. In one example, the set of physiological sensor data includes one or more of electrocardiogram (ECG) data, blood pressure data, photoplethysmogram (PPG) data, gyroscope data, accelerometer data, and body temperature data. Further, in one example, the stability of the patient is determined based on the set of physiological sensor data. Further, in some examples, the first mode of operation of the decision engine includes updating the therapeutic regimen to provide a change in associated dosage of the one or more therapeutic agents and/or initiate one or more new therapeutic agents, or to provide a discontinuation of the one or more therapeutic agents and/or initiate the one or more new therapeutic agents; and the second mode of operation of the decision engine updates the therapeutic regimen to provide one or more of a decrease in the one or more therapeutic agents or discontinuation of the one or more therapeutic agents without initiating the one or more new therapeutic agents. In some examples, each of the one or more therapeutic agents and the one or more new therapeutic agents is selected from the group consisting of beta blockers, Angiotensin-converting enzyme (ACE) inhibitors, angiotensin receptor blockers (ARBs), Angiotensin receptor-neprilysin inhibitors (ARNis), Aldosterone receptor antagonists (MRAs), Sodium-glucose transport protein (SGLT2) inhibitors, and other therapeutic agents for treating heart failure.

Figure 4A:
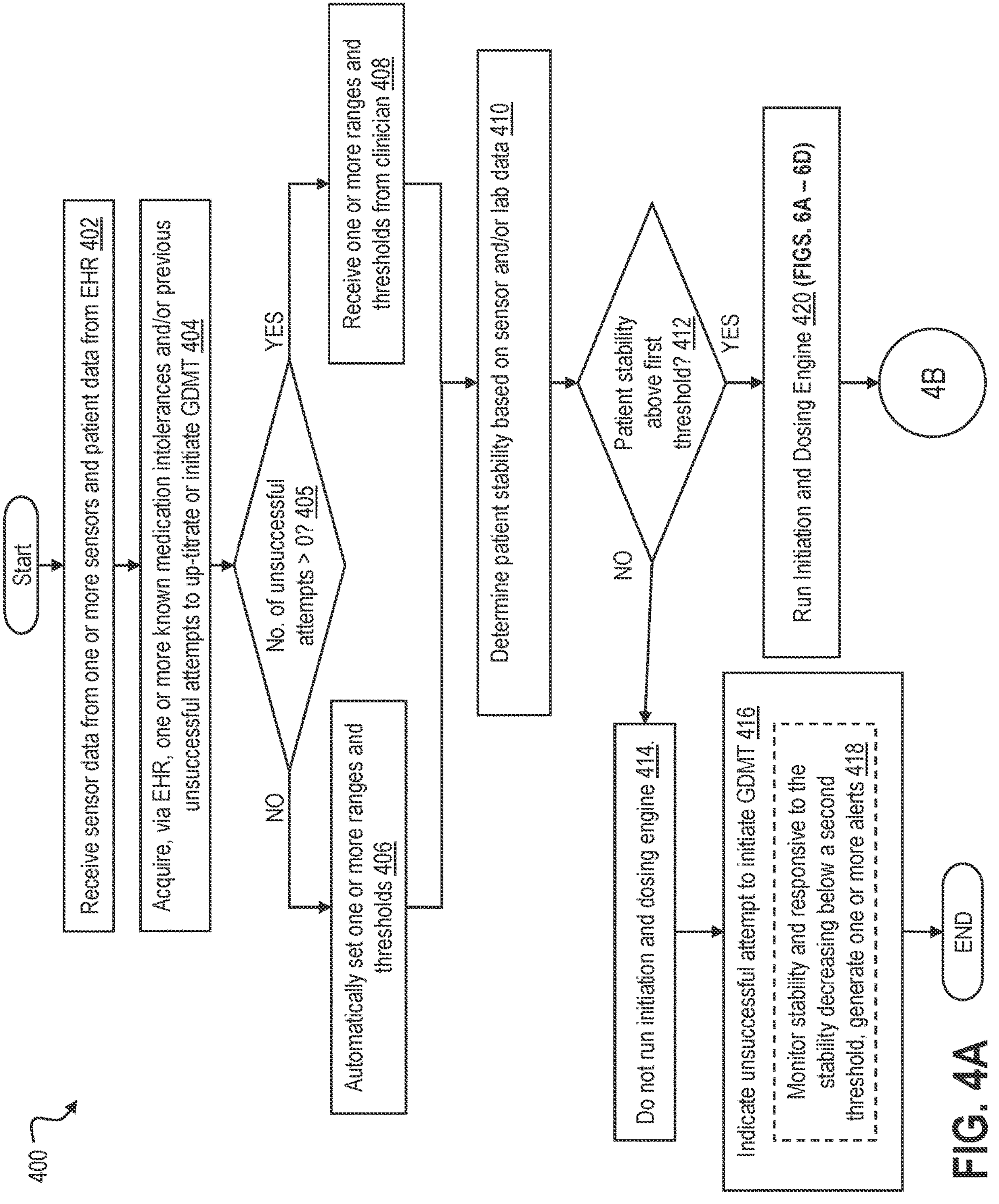
FIG. 4A shows a high-level flow chart of an example method for managing a therapeutic regimen of a patient based patient stability, according to some implementations of the present disclosure.

Turning to FIG. 4A, it shows a high-level flow chart illustrating an example method 400 for initiating an initiation and dosing engine in response to a clinician prescribing evaluation and/or maintenance of a therapeutic regimen for a HF patient, according to another embodiment of the disclosure.

The method 400 begins at 402. At 402, the method 400 includes receiving one or more physiological sensor data from the patient, and one or more patient data from the patient's EHR. Step 402 is similar to 302, and will not be repeated for brevity.

Next, at 404, the method 400 includes receiving, from the EHR, a number of unsuccessful attempts to initiate or up-titrate one or more GDMT medications. For example, if a patient was not clinically stable, an initiation and dosage engine may not be initiated, and accordingly, an unsuccessful attempt may be indicated (e.g., via a counter) and one or more physiological parameters that caused the unsuccessful attempt may be indicated for the patient, and stored in one or more of the cardiac health database and EHR for later retrieval. In some examples, if the initiation and dosing engine is initiated but due to one or more of intolerance to and side-effects resulting from an initiated or up-titrated therapeutic agent, the initiated or up-titrated therapeutic agent may be discontinued or decreased based on patient response. Accordingly, such an event, where the patient response to the initiated or up-titrated therapeutic agent resulted in a second update to discontinue or decrease dosage of the therapeutic agent, may be considered as an unsuccessful attempt to initiate or up-titrate one or more GDMT medications. Further, for each unsuccessful attempt to initiate or up-titrate, the corresponding cause and/or status of one or more physiological parameters at the time of unsuccessful event may be indicated.

Further, at 404, the method 400 includes acquiring, via EHR, one or more known intolerances to GDMT-based therapeutic agents.

Next, at 405, the method includes determining of the number of unsuccessful attempts is greater than zero. If the answer at 405 is NO, the method 400 proceeds to 406. At 406, the method includes prior to running the initiation and dosing engine, automatically setting one or more titration parameters including an average SBP range, an average DBP range, a minimum SBP range, an average heart rate range, and ranges and/or thresholds for lab parameters, including potassium, creatinine, delta creatinine, and eGFR. In one example, the automated titration parameters may be based on an initial indication by the clinician at the time of prescription of the automated initiation and dosing engine.

If the answer at 405 is YES, the method proceeds to 408. At 408, the method 400 includes responsive to detection of a previous unsuccessful attempt (that is, when the number of unsuccessful attempts is greater than zero), receiving clinician confirmation and/or specification of one or more titration parameters.

Upon setting one or more titration parameters, the method 400 proceeds to 410. At 410, the method includes determining patient stability based on remote monitoring sensor data. Determination of patient stability is discussed at step 304 at method 300, and therefore, will not be repeated. Upon determining patient stability, the method 400 proceed to 412 to evaluate if the patient's clinical stability is confirmed or if a stability score of the patient is greater than a threshold stability score. If the answer at 412 is YES, the method 400 proceeds to 420 to run the initiation and dosing engine. If the answer at 412 is NO, then the method 400 does not initiate IDE, and subsequently at 416, the method 400 includes indicating an unsuccessful attempt to initiate or up-titrate GDMT medication.

In one example, responsive to an unsuccessful attempt to initiate or up-titrate GDMT, as discussed at FIG. 3, the safety decision engine may be initiated. However, in some examples, the patient's stability may be continuously monitored for a threshold duration, and responsive to the patient's stability decreasing below a second lower threshold, one or more alerts indicating poor stability conditions may be provided to the clinician and/or patient, thereby prompting the clinician and/or patient (or caregiver) to take immediate actions to improve patient stability (e.g., via hospitalization).

Figure 4B:
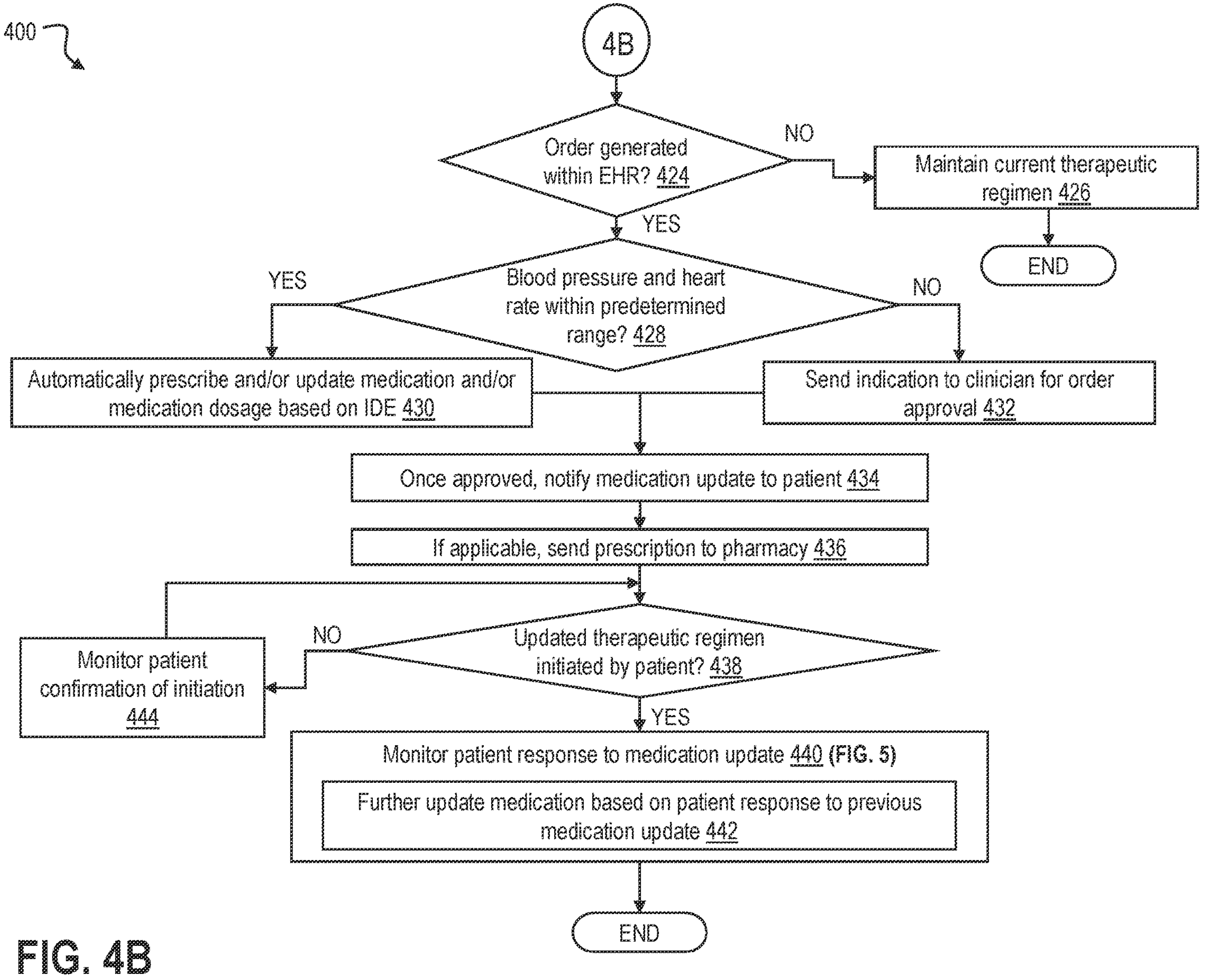
FIG. 4B is a continuation of FIG. 4A.

Returning to 420, upon running the initiation and dosing engine, the method 400 proceeds to 424 continued at FIG. 4B.

At 424, the method 400 includes determining if a prescription and/or lab order is generated by the initiation and dosing engine within the EHR. The prescription may be to initiate one or more medications, increase dosage of one or more medications, decrease dosage of one or more medication, and/or discontinue one or more medications. If the answer at 424 is NO, the method proceeds to 426 to maintain current therapeutic regimen. The method 400 then ends.

If the answer at 424 is YES, the method 400 proceeds to 428. At 428, the method 400 includes determining if one or more selected physiological parameters are within respective desired ranges. The one or more selected physiological parameters may include one or more of an average SBP, an average DBP, and an average heart rate. The thresholds for this step may be more stringent. For example, the threshold blood pressure range and threshold heart rate range may be more narrow in order to perform automatic approval of the updated therapeutic regimen. If the answer at 428 is YES, the method 400 proceeds to 430 to automatically generate (and approve) a corresponding prescription based on the updated therapeutic regimen (based on output of the IDE) within the EHR based on the output of the initiation and dosage engine. If the answer at 428 is NO, the method 400 proceeds to 432. At 432, the method 400 includes transmitting the corresponding prescription to the clinician and receiving clinician approval.

Upon approval (automatically or via clinician), the method 400 proceeds to 434 to notify the patient. Next, at 436, responsive to receiving acknowledgement from the patient, the method 400 includes transmitting the approved prescription to a pharmacy.

Next, at 438, the method 400 includes determining if the patient has initiated the updated therapeutic regimen. If YES, the method 400 proceeds to 440, to monitor response to the updated treatment regimen, as discussed at FIG. 5. Monitoring response to the updated therapeutic regimen may include (at 442) further updating the therapeutic regimen based on a patient response monitored via one or more remote monitoring devices and/or patient indication of response to a questionnaire, as discussed at FIG. 5. If the answer at 438 is NO, the method 400 may continue monitoring indication of initiation of the updated therapeutic agent from the patient.

In this way, guideline based medical therapy for heart failure patients may be efficiently provided. By monitoring patient's physiological parameters before and after updating a therapeutic regiment, and utilizing input from the EHR as well as input from the patient (or caregiver), patient tolerance to any medication adjustment can be efficiently monitored, which in turn allows effective medication updates to reach target doses for HF therapy. As a result, HF therapy is efficiently customized and/or personalized not only on a patient-to-patient basis, but is also updated in a longitudinal manner (over time) for each patient depending on patient progress. In some cases, by combining these various inputs (from sensors, patient EHR, patient input, etc.), if overall patient parameters shows no requirement for medication update or change, unnecessary medication change may be reduced, which also improves patient outcome. Further, the decision engine also enables clinicians to reduce clinical inertia. Further still, decision making efficiency is improved, which allows the clinician more time for other aspects of therapy.

As a non-limiting example, a patient undergoing heart failure therapy with chronic kidney disease, ischemic cardiomyopathy, reduced ejection fraction at 20% is currently prescribed a first therapeutic regimen comprising one or more therapeutic agents. Responsive to stable conditions (e.g., physiological parameters measured from one or more remote patient monitoring sensors and patient reported tolerance to current medications and associated dosage), a decision engine may generate a second therapeutic regimen to include a new therapeutic agent. After administration of the new therapeutic regiment and confirmed intake of the new therapeutic agent by the patient, the decision engine may monitor patient response to the new therapeutic agent via one or more remote patient monitoring sensors and patient reported data (input via an app). During a patient response monitoring period, responsive to remote monitoring data and/or patient reported data indicating one or more of intolerance and side effects (e.g., dizziness or syncope), the decision engine may run the decision engine in the second mode (e.g., safety decision engine) and generate a third therapeutic regimen to either decrease the dosage of the new therapeutic agent or discontinue the new therapeutic agent. The decision engine may continue monitoring the patient response to the third therapeutic regimen to determine if further updates are necessary or maintain the third therapeutic regimen. In some examples, after generating an updated therapeutic regimen and determining that the patient is able to tolerate the updated therapeutic regimen, there may be a period of time (before a next update) when the patient response is monitored but no updates are made.

As another example, the decision engine monitoring a patient undergoing HF therapy and currently under a first therapeutic regimen may identify a heart condition event (e.g., atrial fibrillation) using data from one or more physiological sensors. Responsive to which, decision engine may generate an updated therapeutic regimen with initiation of a blood thinner. The decision engine, upon receiving confirmation of uptake/administration of the updated therapeutic regimen may perform patient response monitoring as discussed above.

As yet another example, the decision engine may manage HF therapy for a 42 year old HF patient who had anterior myocardial infarction. The patient may be initiated on a therapeutic regimen comprising Carvedilol and Entresto and associated doses. Responsive to a lab result indicating intolerance to higher doses of Entresto, the decision engine may generate an updated regimen with lower dosage for Entresto.

Turning next to FIGS. 6A-6D, it shows an example method 600 for updating a therapeutic regimen for a HF patient. In particular, method 600 shows operation of an initiation and dosing engine (IDE). Prior to initiating IDE, a stability check may be performed and therapeutic dosage limits for one or more GDMT-based therapeutic agents may be provided to the IDE (either automatically or based on clinician indication) as discussed at FIGS. 3, 4A and 4B. Further, the IDE may be initiated only when the patient is confirmed to the clinically stable to initiate a therapeutic agent and/or up-titrate a currently prescribed therapeutic agent.

Further, the method 600 below will be described with respect to example thresholds and/or ranges for various physiological parameters (estimated and/or measured via one or more physiological sensors) and laboratory parameters (acquired from the patient's EHR); however, it will be appreciated that the ranges and thresholds may be customized based on a given health condition for the patient.

The method 600 begins at 602. At 602, the method 600 includes determining if a combination of GDMT-based therapeutic agents and non-GDMT based therapeutic agents are included in the therapeutic regimen for the HF patient. GDMT-based therapeutic agents are therapeutic agents prescribed to patients with HF according to guideline-directed medical therapy (GDMT). Non-GDMT based therapeutic agents are therapeutic agents that are not indicated in the GDMT.

If the answer at 602 is YES, the method 600 proceeds to 604 to stop combination medications and subsequently to 606 to start constituents except sacubitril/valsartan, and then proceeds to 608. If the answer at 602 is NO, the method 600 directly proceeds to 608.

At 608, the method 600 includes running the safety decision engine (SDE). The SDE may monitor for indications of one or more of acute kidney injury, hyperkalemia, hypotension, and bradycardia. Further, if the remote patient monitoring data indicates that the patient has met any critical safety thresholds, then the SDE may recommend that the patient either discontinue or decrease the dosage of a therapeutic agent or provide an indication to re-check one or more laboratory tests. Accordingly, prior to increasing a dosage of a therapeutic agent and/or initiating a new therapeutic agent, the SDE may be executed. Details of the SDE are described with respect to FIG. 7.

Upon running SDE, the method 600 proceeds to 610. At 610, the method 600 includes determining if SDE has indicated decrease or discontinuation of one or more medications. If YES, the method 600 proceeds to 614 to update the therapeutic regimen based on SDE output to decrease a therapeutic agent and/or discontinue a second therapeutic agent. If the SDE output indicated no titration (that is, if answer at 610 is NO), the method 600 proceeds to 612 to maintain current therapeutic regimen after SDE output. The method 600, after updating or maintaining the therapeutic regimen after SDE, proceeds to 616.

At 616, the method 600 includes determining whether a systolic blood pressure (SBP) is less than or equal to 140 mm Hg. If YES, the method 600 proceeds to 618. At 618, the method 600 includes determining if the patient is on non-GDMT hypertensive medication. If the patient is on non-GDMT hypertensive medication, the answer at 618 is YES, and the method proceeds to 620. At 620, the method 600 includes decreasing the non-GDMT hypertensive medication or discontinuing the non-GDMT hypertensive medication. For example, if the SBP is less than or equal to 120 mm Hg, the non-GDMT hypertensive medication is discontinued, or if the SBP is between 120 and 140 mm Hg, the non-GDMT hypertensive medication is decreased by one level.

Figure 6A:
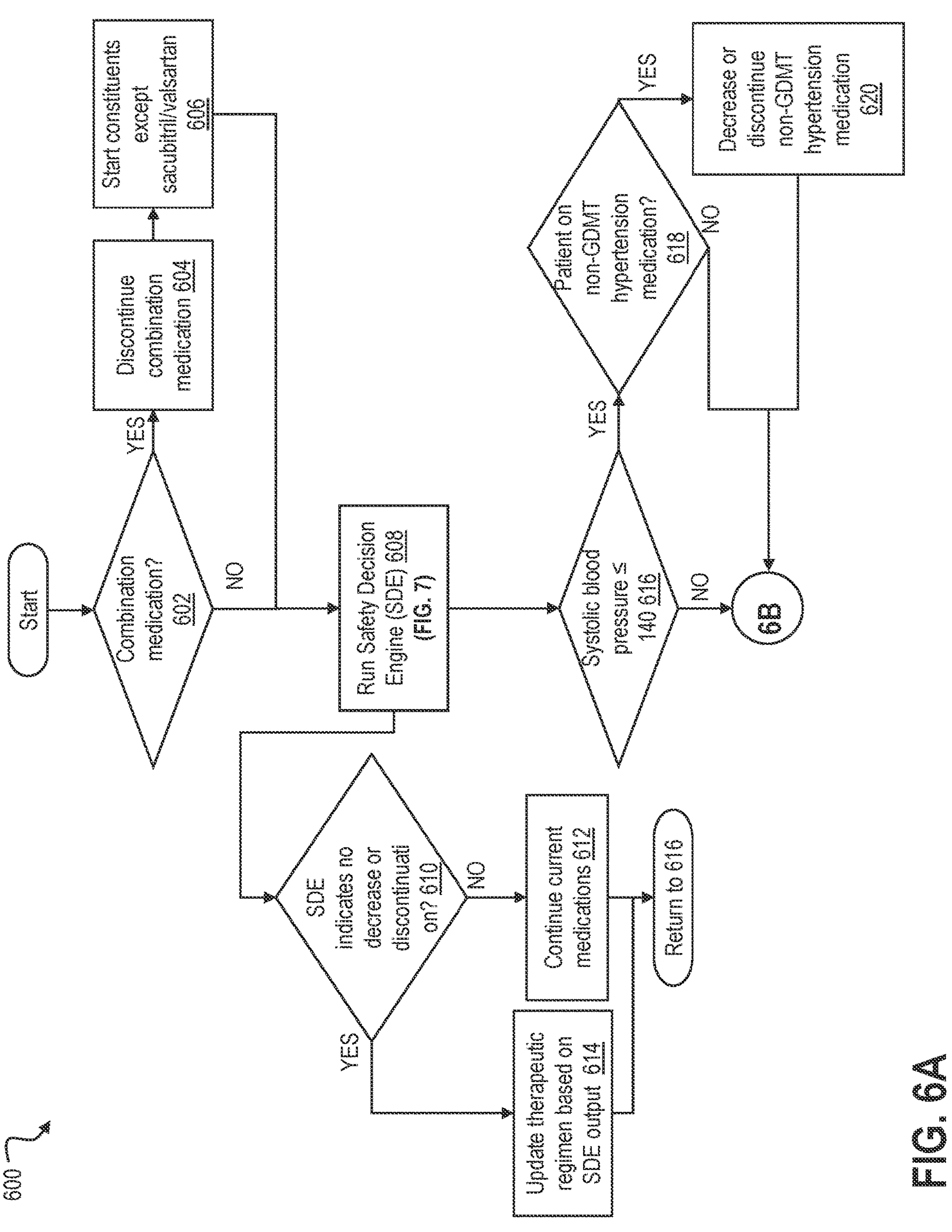
FIG. 6A shows a high-level flow chart of an example initiation and dosing engine for managing a therapeutic regimen of a patient when the patient is stable, according to some implementations of the present disclosure.
Figure 6B:
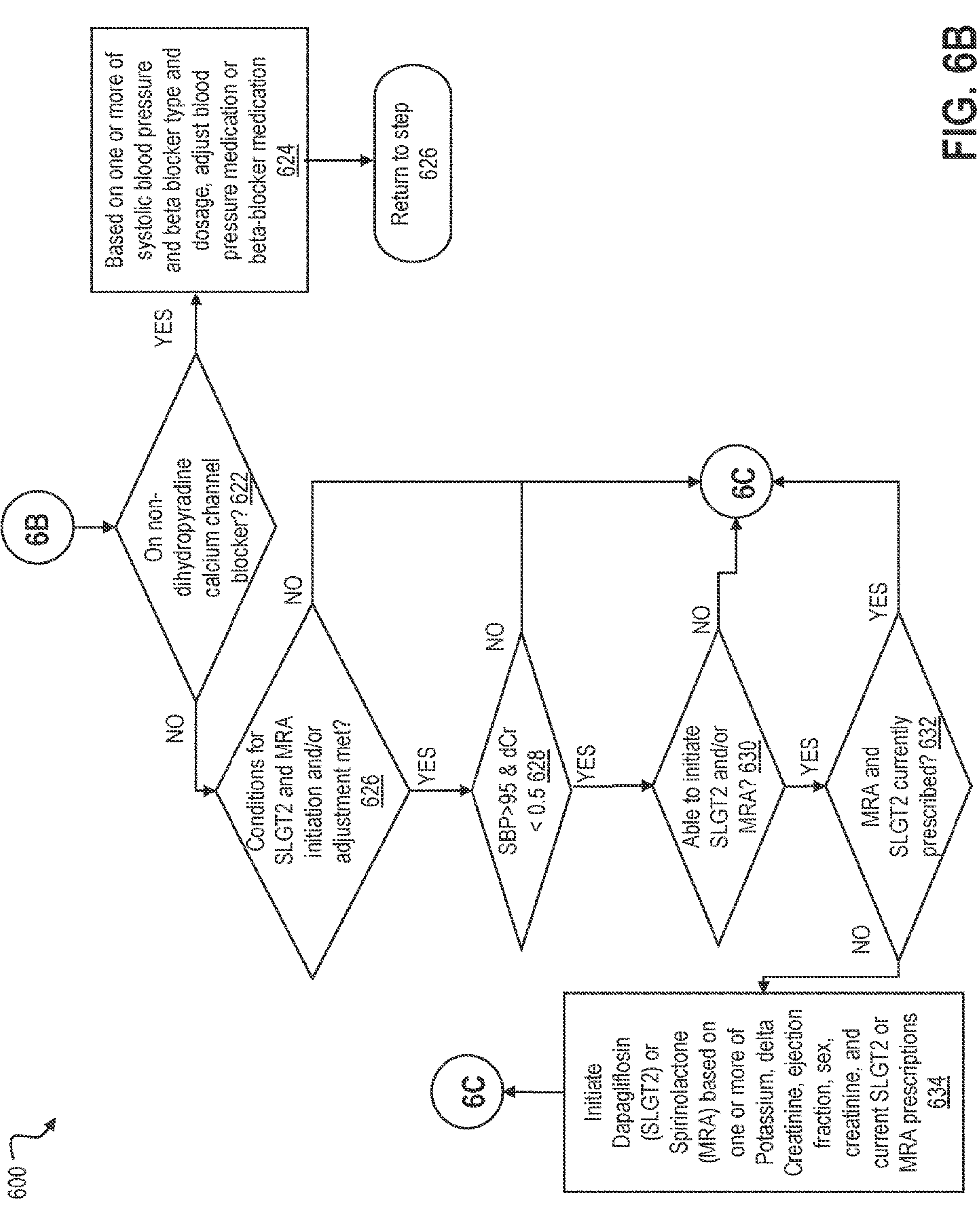
FIG. 6B is a continuation of FIG. 6A.

Returning to 616, if the answer at 616 is NO (that is, if SBP greater than 140 mm Hg), the method 600 proceeds to 622 continued at FIG. 6B. Referring now to FIG. 6B, at 622, the method 600 includes determining if the patient is on non-dihydropyradine calcium channel blocker. If the answer at 622 is YES, the method 600 proceeds to 624. At 624, the method 600 includes adjusting blood pressure medication or beta blocker (BB) medication based on SBP and current BB type and dosage. For example, if the SBP is greater than or equal to 110, a GDMT BB may be initiated or a dosage of a GDMT BB may be increased, or a non-GDMT BB may be converted to equal dosage GDMT BB. Further, if the SBP is greater than or equal to 100 but less than 110, then conversion or dosage increase to metroprolol may be performed up to level 3. If the SBP is less than 100, then non-dihydropridine may be discontinued. The method 600 then returns to 626.

Returning to 626, the method 600 includes determining if conditions for MRA initiation and/or SLGT2 adjustment are met. In one example, conditions for MRA and/or SLGT2 adjustment may include 1) the patient on GDMT BB and on Angiotensin Receptor-Neprilysin Inhibitor (ARNi) and SBP less than 140 and heart rate (HR) less than 80 OR 2) the patient is ARNi intolerant and on GDMT BB and on (Angiotensin-converting enzyme inhibitor (ACEi) level 3, 4, or 5, or on Angiotensin II receptor blocker (ARB) level 2, 3, 4, or 5) and SBP less than 140 and HR less than 80.

Figure 6C:
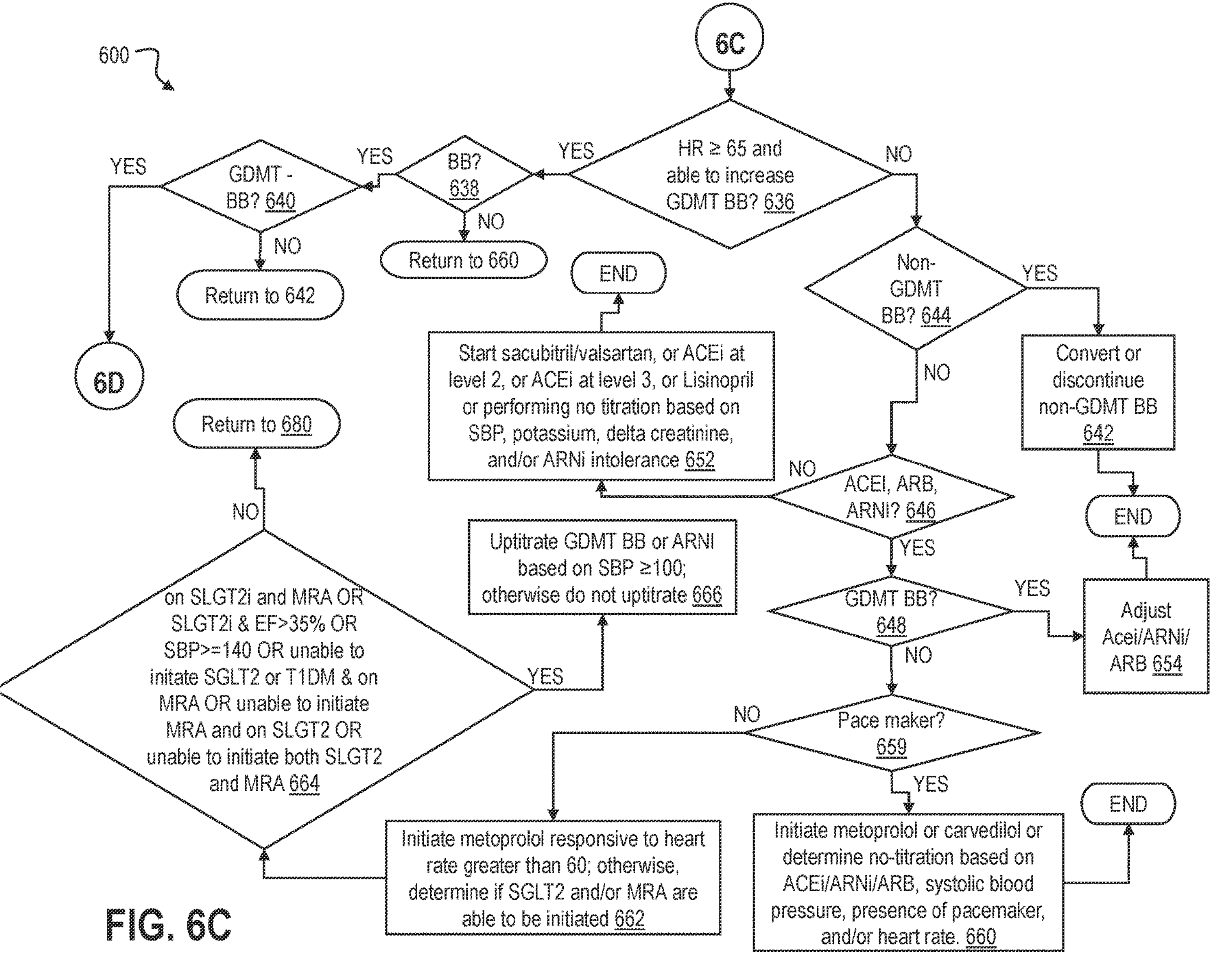
FIG. 6C is a continuation of FIG. 6B.

If the answer at 626 is YES, the method 600 proceeds to 628; otherwise, the method 600 proceeds to 636 continued at FIG. 6C. At 628, the method 600 includes determining is SBP is greater than 95 and delta creatinine level is less than 0.5. If the answer at 628 is NO, the method proceeds to 636 at FIG. 6C. If the answer at 628 is YES, the method 600 proceeds to 630 determine if Spirinolactone (MRA) and/or Dapagliflosin (SLGT2) is able to be initiated (that is, if no prior intolerances or side-effects to MRA and/or SLGT2 are indicated in the patient's EHR). If NO, the method 600 proceeds to 636 at FIG. 6C. If answer at 630 is YES, the method 600 proceeds to 632 to determine of MRA and SLGT2 are currently prescribed. If the answer at 632 is YES, the method 600 proceeds to 636 at FIG. 6C; otherwise if MRA or SLGT2 are not currently prescribed, the method 600 proceeds to 634. At 634, the method 600 includes initiating Dapagliflosin (SLGT2) or Spirinolactone (MRA) based on one or more of Potassium, delta Creatinine, ejection fraction, sex, creatinine, and current SLGT2 or MRA prescriptions.

Referring to FIG. 6C, it continues from FIG. 6B. At 636, the method 600 includes determining if HR is greater than or equal to 65 and if GDMT BB is able to be increased. If the answer at 636 is YES, the method 600 proceeds to 638 to determine if the patient is currently on a BB medication. If the answer at 638 is NO, the patient is not on a BB, and the method proceeds to 660 to initiate metoprolol or carvedilol or determine no-titration based on systolic blood pressure, presence of permanent pacemaker, whether on ACEi/ARB/ARNi, and/or heart rate. If the answer at 638 is YES, the method 600 proceeds to 640 to determine if the patient is on GDMT BB. If the patient is not on GDMT BB, the answer at 640 is NO, and the method 600 proceeds to 642. At 642, the method 600 includes converting to GDMT BB or discontinuing non-GDMT BB based on SBP and/or HR. Returning to 640, if the patient is on GDMT BB, the method 600 proceeds to 670 continued at FIG. 6D.

Returning to 636, if the HR less than or equal to 65 and not able to increase GDMT BB, the answer at 636 is NO, and the method proceeds to 644. At 644, the method 600 includes determining if the patient is on a non-GDMT BB. If the answer at 644 is YES, the method proceeds to 642 to convert to GDMT BB or discontinuing non-GDMT BB based on SBP and/or HR. If the answer at 644 is NO, the method 600 proceeds to 646 to determine is the patient is on ACEi/ARNi/ARB. If the answer at 646 is NO, the method 600 proceeds to 652. At 652, the method 600 includes starting sacubitril/valsartan, or starting ACEi at level 2, or starting ACEi at level 3, or starting Lisinopril or performing no titration based on SBP, potassium, delta creatinine, and/or ARNi intolerance. If the answer at 646 is YES, the method proceeds to 648 to first determine if the patient is on GDMT BB, and if so, the method 600 proceeds to 654 to optimize ACEi/ARNi/ARB. If the answer at 648 is NO, the method 600 proceeds to 659 to determine is the patient is on pacemaker. If yes, the method 600 proceeds to 660. If the answer at 659 is NO, the method 600 proceeds to 662. At 662, the method 600 includes initiating metoprolol responsive to heart rate greater than 60; otherwise, the method 600 includes determining if SGLT2 and/or MRA are able to be initiated. The method 600 then proceeds to 664. If conditions at 664 are met, the method 600 proceeds to 666 to uptitrate GDMT BB or ARNI based on SBP≥100; otherwise performing no titration. If conditions at 664 are not met, the method 600 proceeds to 680 at FIG. 6D.

Figure 6D:
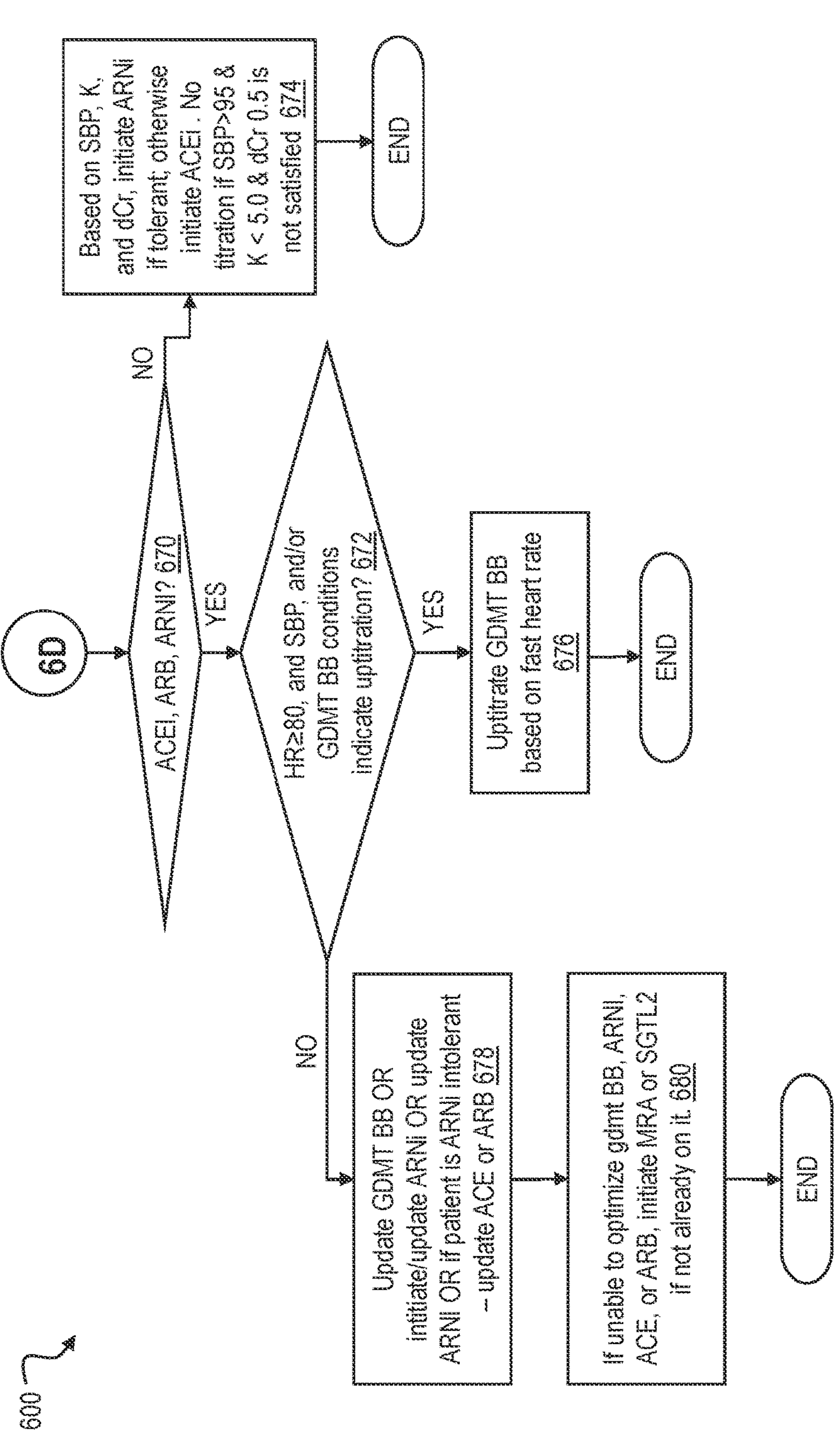
FIG. 6D is a continuation of FIG. 6C.

Referring now to FIG. 6D, it is a continuation of FIG. 6C. At 670, the method 600 includes determining if the patient is on one or more of ACEi, ARB, and ARNI. If the answer at 670 is NO, the method proceeds to 674. At 674, the method 600 includes initiating ARNi based on SBP, K, and dCr, if tolerant; otherwise initiating ACEi. No titration if SBP>95 & K<5.0 & dCr 0.5 is not satisfied. If the answer at 670 is YES, the method 600 proceeds to 672 to determine if HR is greater than or equal to 80 and if SBP and/or GDMT BB conditions indicate uptitration. If YES, the method 600 proceeds to 676 to uptitrate GDMT BB based on fast heart rate. If the answer at 672 is NO, the method 600 proceeds to 678 to update GDMT BB OR initiate or update ARNi OR update ARNi OR if patient is ARNi intolerant, update ACE or ARB.

Next, method 600 proceeds to 680. At 680, the method 600 includes if unable to optimize GDMT BB, ARNi, ACEi, or ARB, initiate MRA or SGTL2 if not already on it. The 600 method then ends.

Referring next to FIG. 7, it shows a high-level flow chart illustrating an example method 700 for decreasing or discontinuing one or more therapeutic agents in a therapeutic regimen for HF patients. In particular, method 700 may be implemented when the decision engine is operated in a safety decision engine (SDE) mode (also referred to as second mode of decision engine), such as when a patient stability is below a threshold, or for monitoring patient response to a change in the therapeutic regimen (e.g., after a therapeutic agent has been increased or initiated or decreased or discontinued from a previous therapeutic regimen update). Accordingly, the method 700 may be implemented for monitoring for symptoms of drug side effects, acute kidney injury, hyperkalemia, hypotension, and/or bradycardia. If indications from one or more physiological sensors (e.g., remote monitoring data) show that the patient has met any physiological parameter thresholds, then the method 700 may generate an updated therapeutic regimen, wherein the updated therapeutic regimen includes discontinuation or decrease in the dosage associated with one or more therapeutic agents. In some examples, the method 700 may recommend the updates, and the recommendations for updating the therapeutic regimen may then be approved by the clinician. In some other example, the method 700 may automatically generate updates to the therapeutic regimen.

Method 700 begins at 702. At 702, the method 700 includes determining if a potassium level is greater than or equal to 5 nmol/L or if delta creatinine value is greater than or equal to 0.5 mg/dL. If YES, the method 700 proceeds to 704 to determine if the patient is on KCl. If YES, the method 700 proceeds to 706 to update a therapeutic regimen to discontinue KCl, and then returns to 760. If the patient is not on KCl, the method 700 proceeds to 760 from 704.

At 760, the method 700 includes based on delta creatinine levels and/or potassium levels, and whether on MRA, ACEi or ARB or ARNi, updating to adjust treatment regimen to decrease or discontinue MRA dosage (752), or decrease or discontinue ACEi dosage (754), or decrease or discontinue ARB dosage (756), or decrease or discontinue ARNi dosage (758). In particular, if the patient's potassium level is between 5.5 and 6, and if the patient is on MRA, the MRA dosage is updated to reduce to a lower lever if currently at levels 5, 4, 3, or 2. If the MRA dosage is currently at level 1, then the update includes discontinuation of MRA. Further, if the patient is on MRA and the delta creatinine levels are greater than or equal to 0.5 or if the patient is on MRA and the potassium level is greater than 6, the method 700 updates the therapeutic regimen to discontinue MRA. Similarly, based on whether the patient is on ACEi, ARB, or ARNi, and based on potassium and delta creatinine levels of the patient, ACEi, ARB, or ARNi may be discontinued or the corresponding dosage is may be decreased.

In this way, based on patient's laboratory results of potassium (K) and/or delta creatinine levels (dCr), which may be obtained from the patient data from the patient's EHR, and based on current therapeutic regimen, also obtained from the patient data from the patient's EHR, the method 700 provides updates to reduce dosage to a lower level or discontinue a therapeutic agent. Thus, kidney function indicated by potassium and delta creatinine levels is taken into account in making updates to the therapeutic regimen for decreasing or discontinuing a therapeutic agent.

Returning to 702, if the answer is NO, the method 700 proceeds to 708. At 708, the method 700 includes determining if an average SBP is less than or equal to 95 and if a minimum SBP is less than 90. As discussed above, in one example, the blood pressure values (e.g., average SBP, minimum SBP, average DBP) may be received from a remote blood pressure monitoring device, and may indicate blood pressure values over a monitoring period. In some examples, the processing system (e.g., server 150) may receive raw or pre-processed data from the remote blood pressure monitoring device, and calculate the blood pressure values over the monitoring period. In any case, remotely monitored blood pressure data is used for providing adjustments to a treatment regimen.

If the answer at 708 is YES, the method 700 proceeds to 720. At 720, the method 700 includes providing an update based on heart rate (HR) less than threshold for bradycardia and/or minimum SBP less than 90 mm Hg, and whether on non-GDMT hypertensive medication or BB or ACEi or ARB or ARNi. In particular, update is provided to adjust treatment regimen to discontinue non-GDMT hypertensive medication (722), or decrease or discontinue BB (724), or decrease or discontinue ACEi (726), or decrease or discontinue ARB (730), or decrease or discontinue ARNi (732). That is, if the patient is only on BB or only on ACEi or only on ARB or only on ARNi, the respective medication is decreased to a lower level or discontinued based on minimum SBP being less than 90 and/or heart rate less than a threshold (e.g., 60).

Next, the method 700 proceeds to 740. At 740, the method 700 includes updating the therapeutic regimen based on whether the patient is on a combination of a beta blocker (BB) and ACEi, ARB, or ARNi, and minimum SBP less than 90 and HR less than a second threshold (e.g., 65), which may be greater than the threshold at 720, wherein the update includes a decrease or discontinuation of BB or one of ACEi, ARB, or ARNi. That is, an update is provided to decrease or discontinue BB (742), or decrease or discontinue ACEi (744), or decrease or discontinue ARB (746), or decrease or discontinue ARNi (748), or No titration (750). The method 700 then ends.

In this way, the method 700 checks serum electrolyte (potassium) and metabolite (delta creatinine) levels using patient data from the EHR for indications of hyperkalemia and abnormal kidney function, checks physiological parameters (e.g., minimum SBP, average SBP, an HR) using remote monitoring data for indications of hypotension and bradycardia, and provides updates a therapeutic regimen, for example, to decrease or discontinue one or more therapeutic agents.

While the above example describes updates performed by the safety decision engine, in some examples, one or more of the updates discussed above may be provided as recommendations to the therapeutic regimen. Further, upon review and approval by a clinician, the therapeutic regimen may be updated with recommendations provided by the safety decision engine.

Figure 12A:
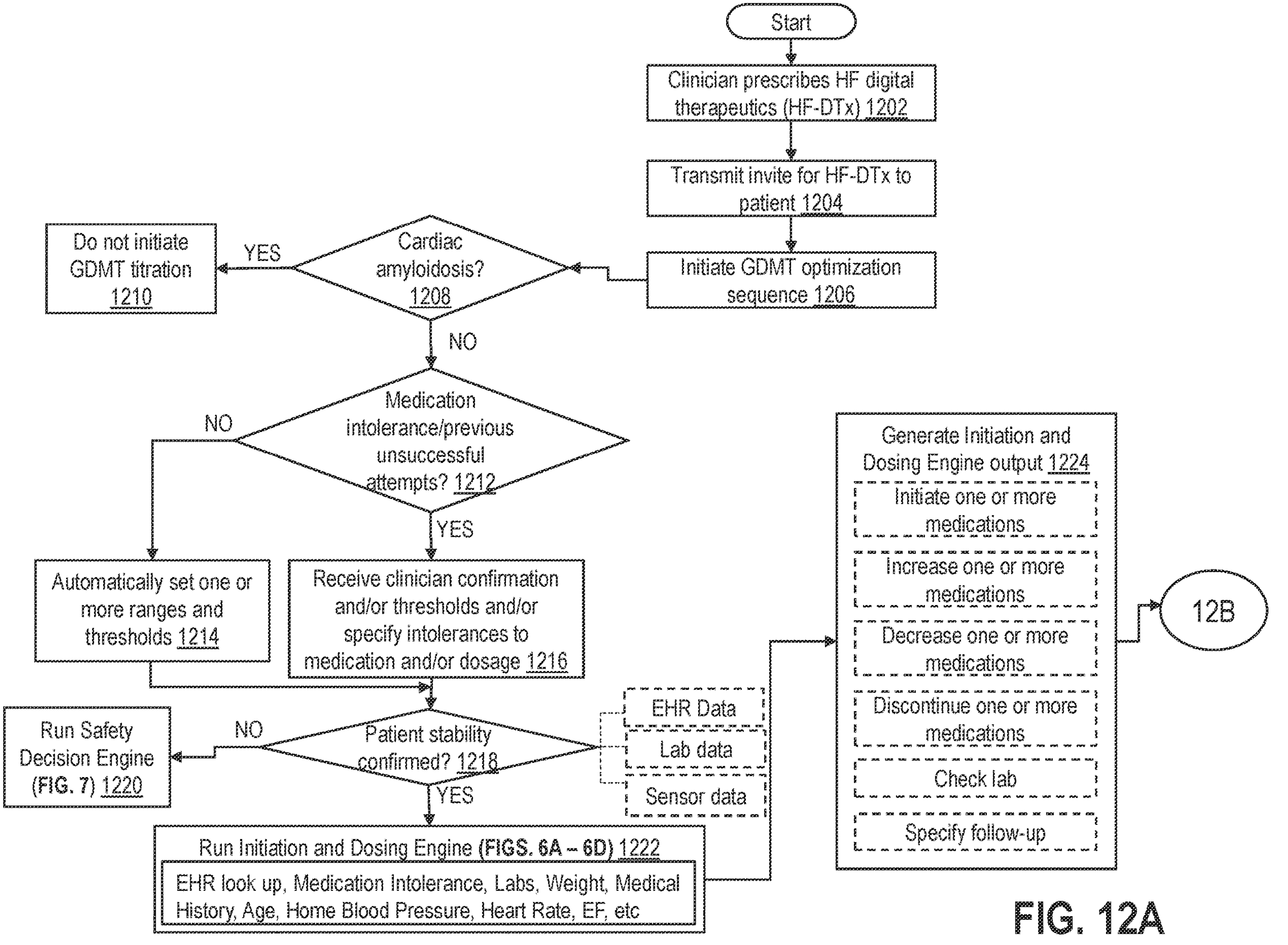
FIGS. 12A-12B shows a high level flowchart illustrating an example method for managing a therapeutic regimen for a heart failure patient, including initiating a heart failure digital therapeutics decision engine and generating a follow-up schedule, according to some implementations of the present disclosure.
Figure 12B:
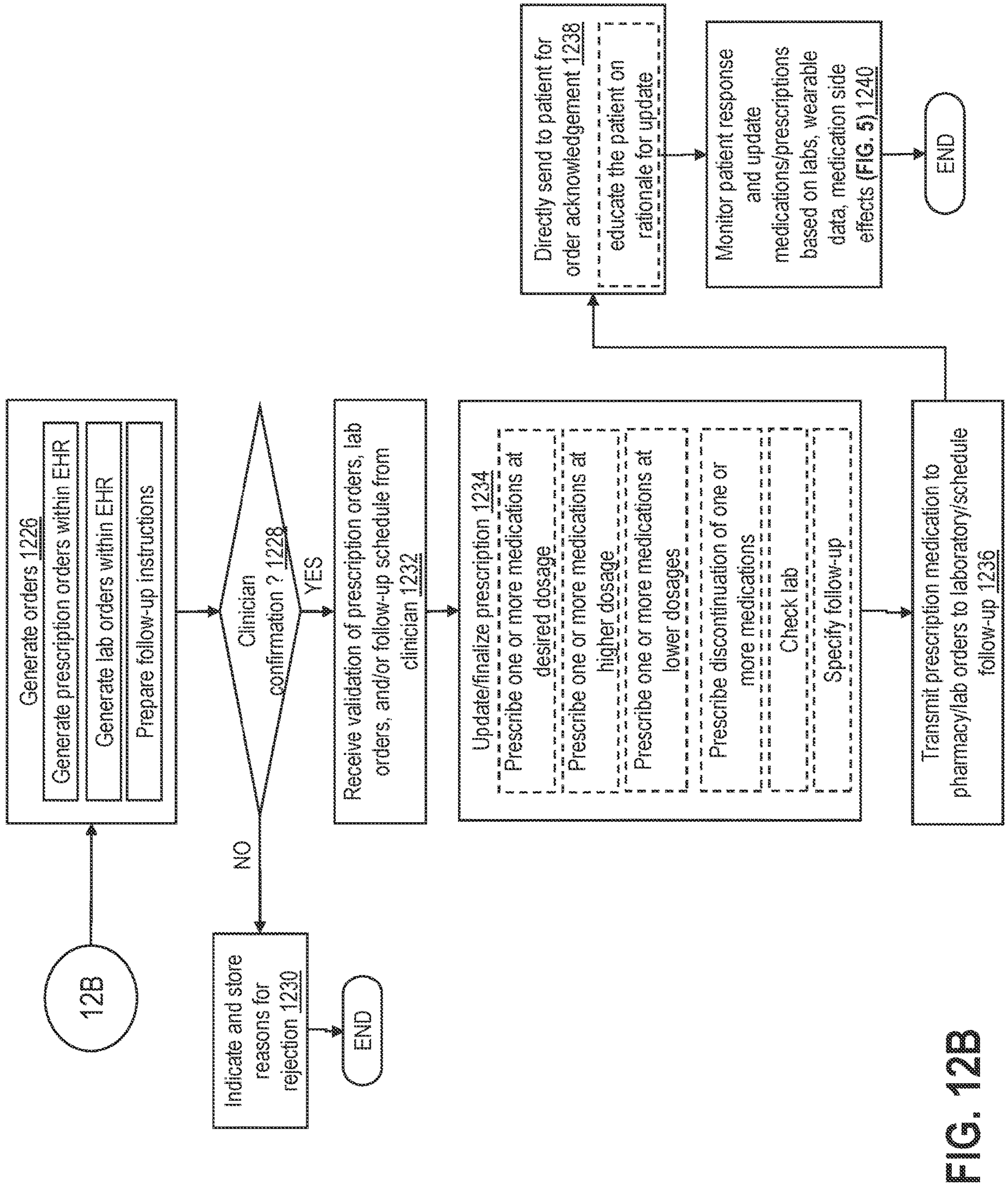

Referring to FIGS. 12A and 12B, it shows an example method for initiating a heart failure digital therapeutics and managing a therapeutic regimen for a patient diagnosed with or at a risk of developing a cardiac health condition.

In one embodiment, if cardiac amyloidosis is confirmed, GDMT optimization may not be initiated.

Further, the decision engine work flow includes implementation of follow-up care including a customized follow-up schedule based on one or more of medications in the prescribed therapeutic regimen, medication updates to the prescribed therapeutic regimen, lab work scheduled, lab results, patient sensor data, and patient medication adherence data.

Figure 13A:
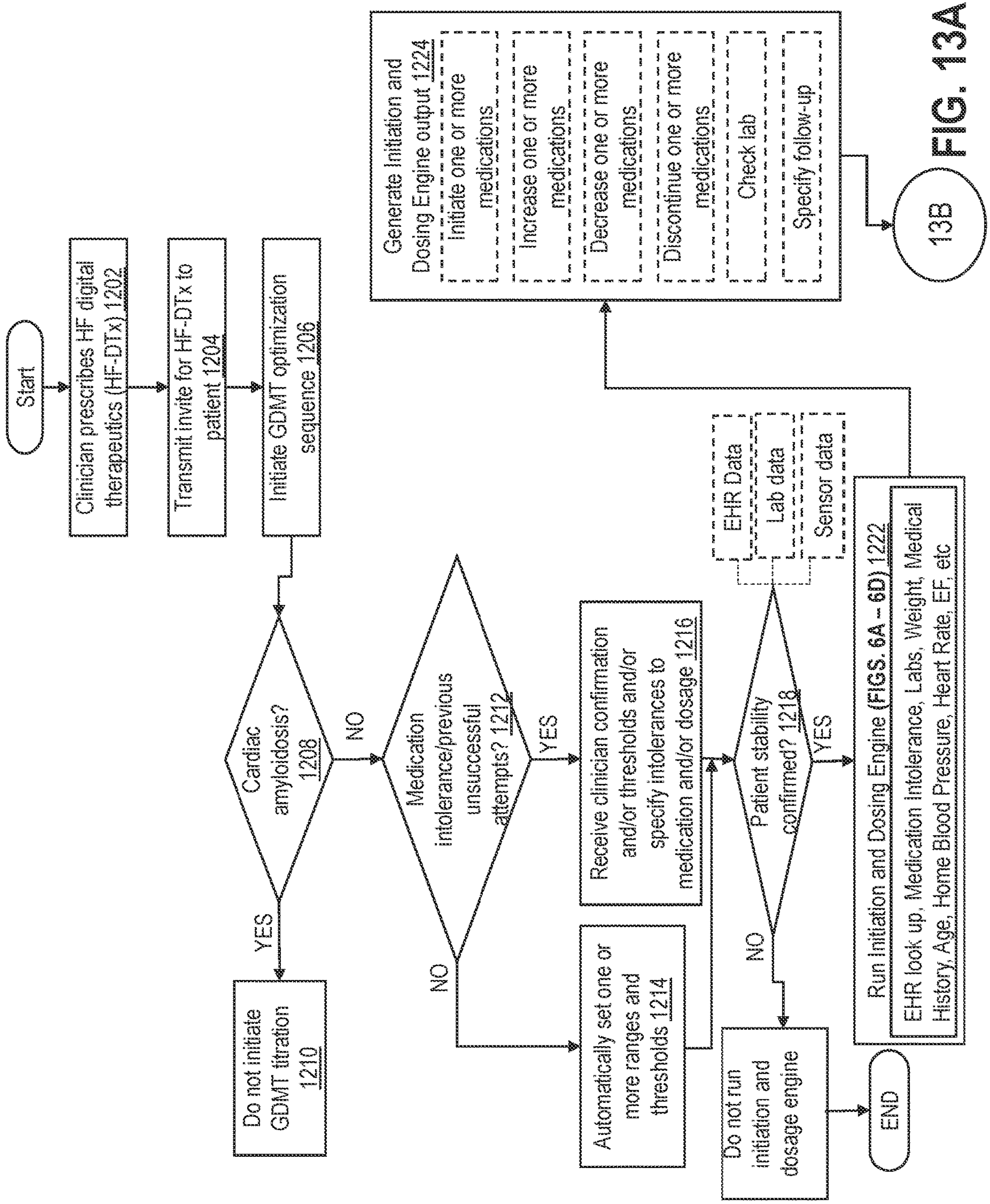
FIGS. 13A-13B shows a high level flowchart illustrating an example method for managing a therapeutic regimen for a heart failure patient, including initiating a heart failure digital therapeutics decision engine and generating a follow-up schedule, according to some implementations of the present disclosure.
Figure 13B:
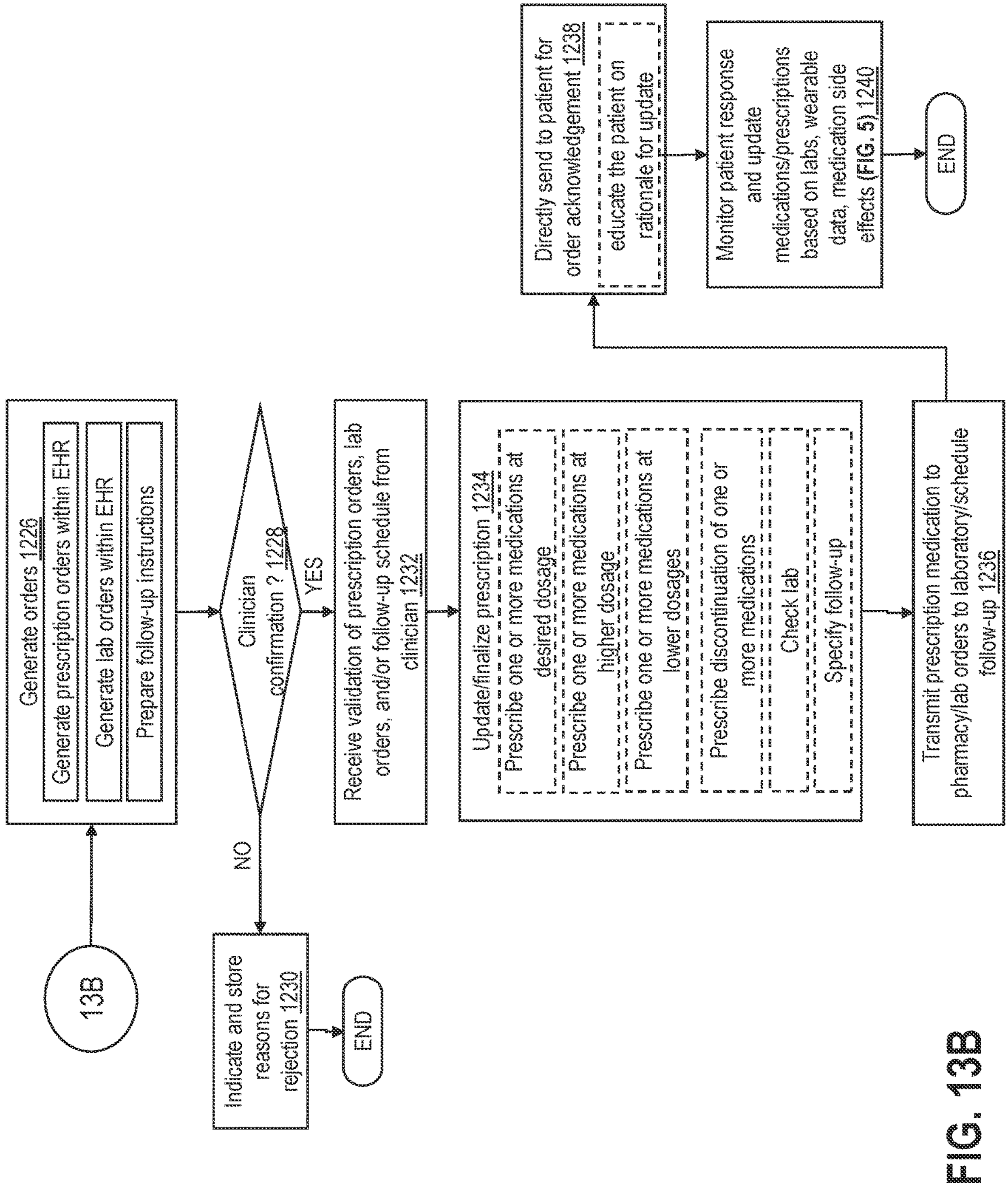
Figure 14:
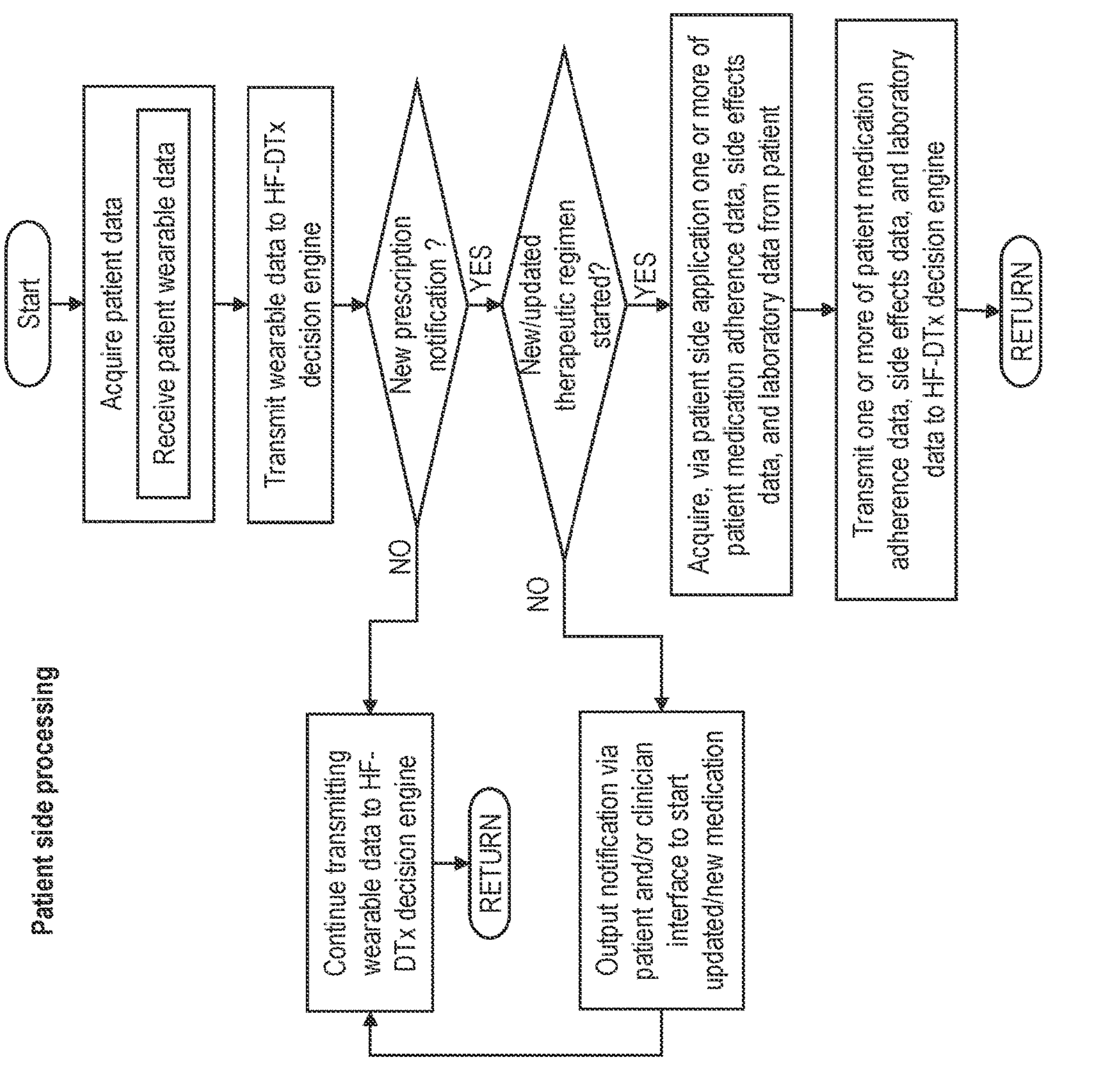
FIG. 14 shows a high level flowchart illustrating an example method of a patient side process for receiving an initial and/or updated heart failure therapeutic regimen from a prescribed heart failure digital therapeutics decision engine, monitoring patient response, and transmitting patient data (e.g., sensor data, lab data, medication side effects data, adherence data, etc.) to the decision engine, according to some implementations of the present disclosure.

FIGS. 13A and 13B, it shows another example method for initiating a heart failure digital therapeutics and managing a therapeutic regimen for a patient diagnosed with or at a risk of developing a cardiac health condition. This method may be implemented for a first time patient who is not taking or has been prescribed any GDMT medications. Accordingly, if patient clinical stability (step 1218) based on sensor data and/or lab data (e.g., potassium levels, blood pressure levels, etc.) is not within desired respective thresholds, the initiation and dosing engine may not be initiated.

FIG. 14 shows an example method for obtaining patient data from a patient and communicating with the decision engine. For example, the method may be implemented by a processor of a computing device, such as the computing device 120 including a patient side application.

Figure 15A:
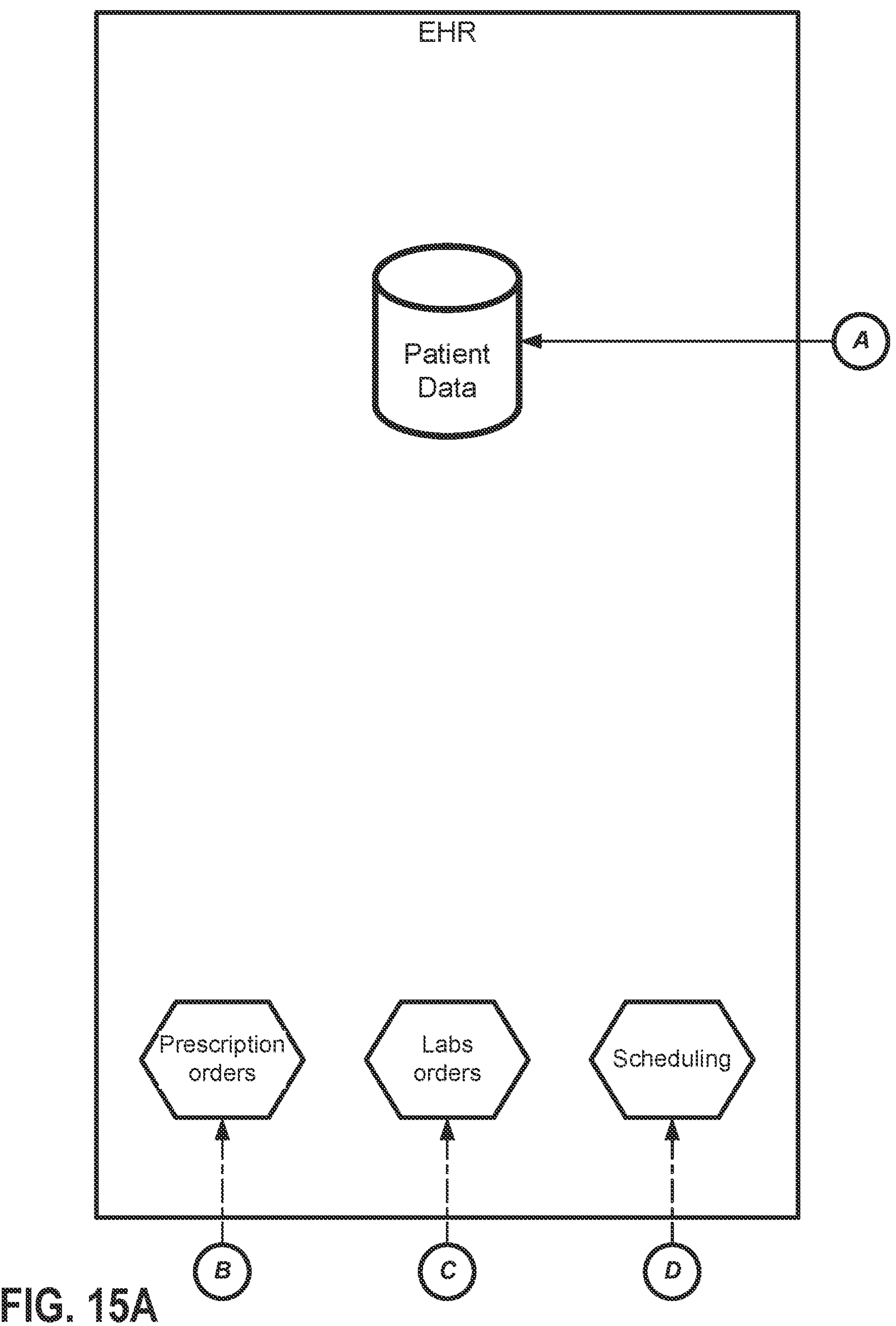
FIGS. 15A-15O show a high level flowchart illustrating an example method for managing a therapeutic regimen for a heart failure patient, including initiating a heart failure digital therapeutics decision engine and generating a follow-up schedule, according to some implementations of the present disclosure.
Figure 15B:
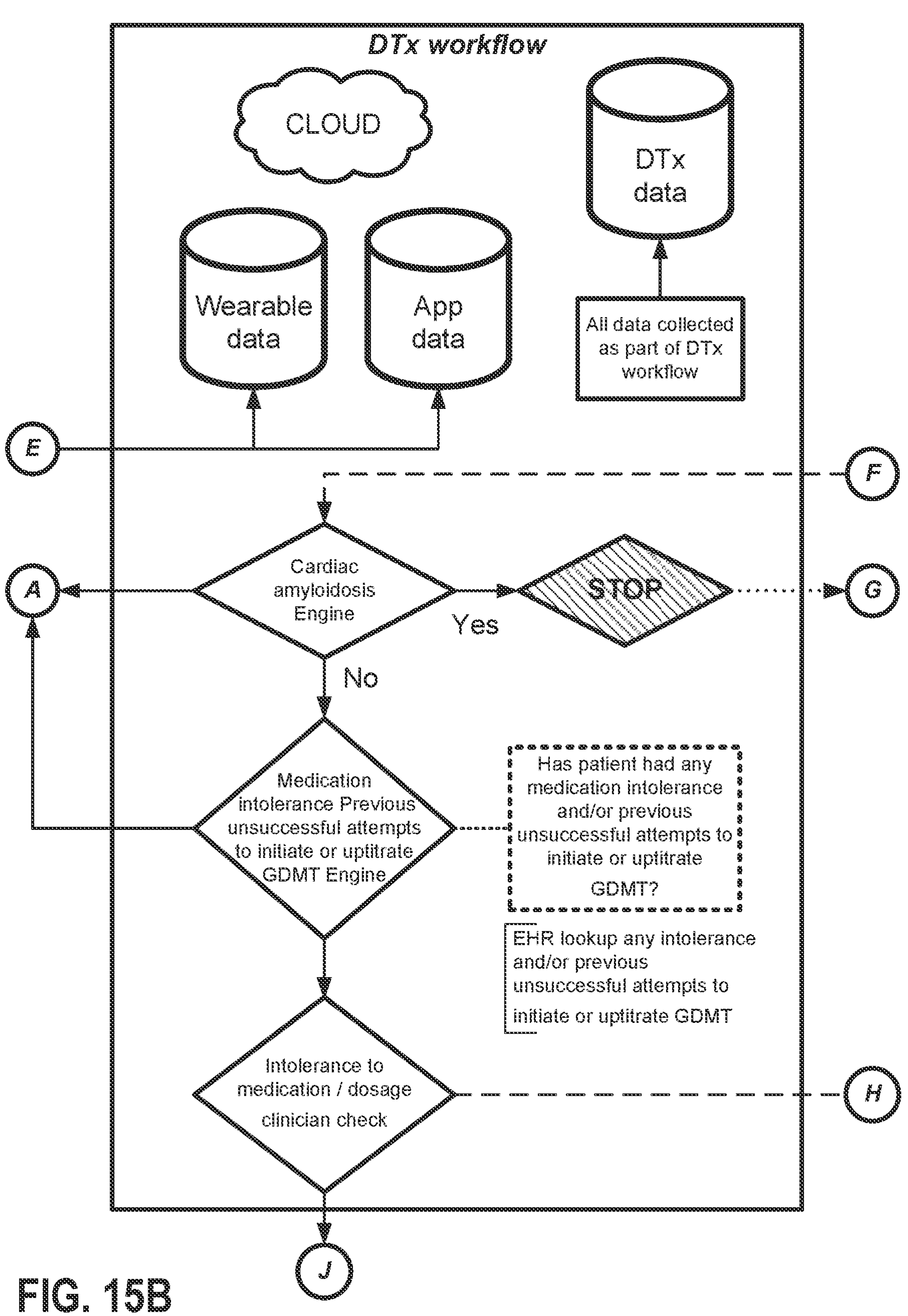
Figure 15C:
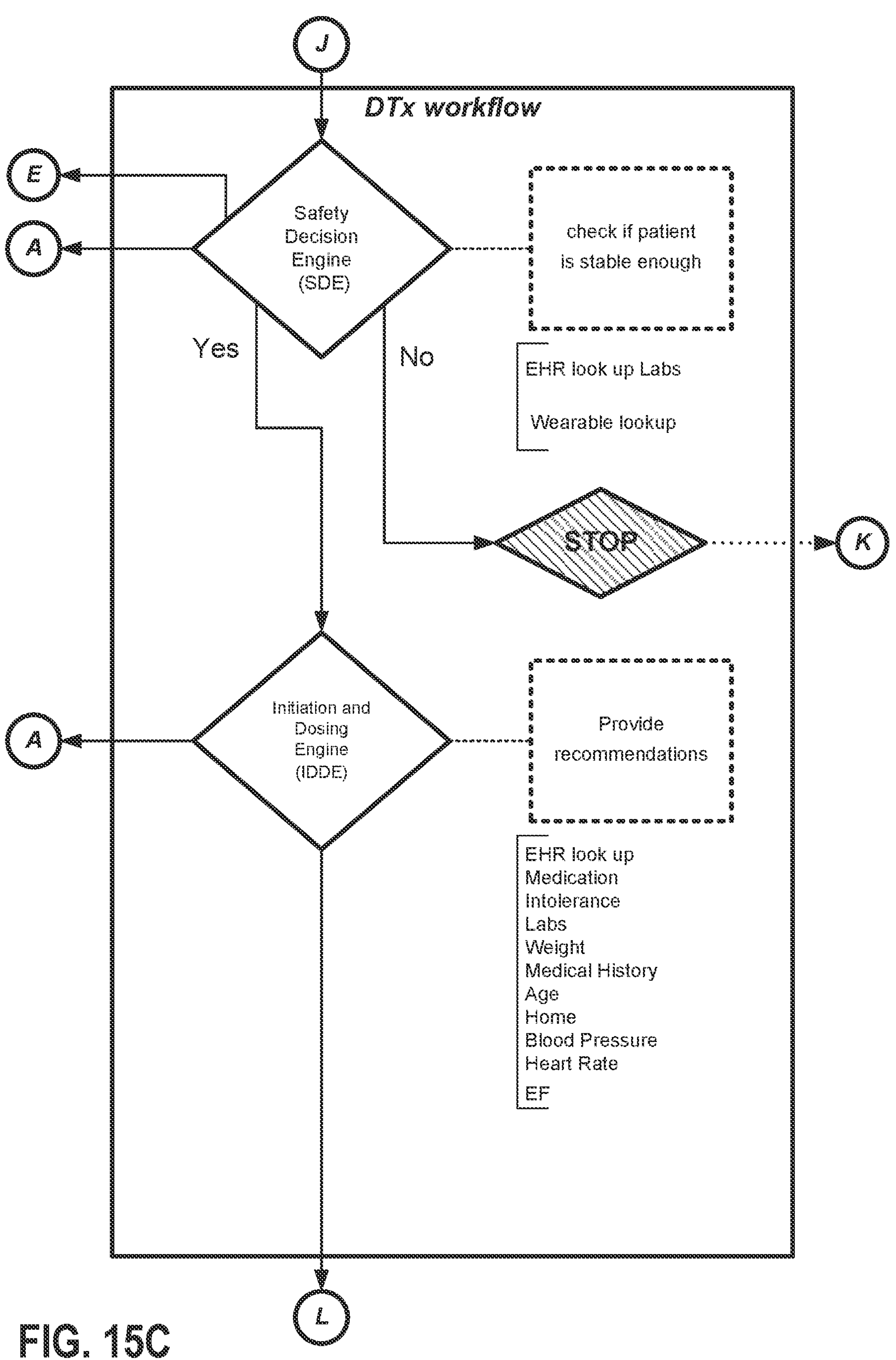
Figure 15D:
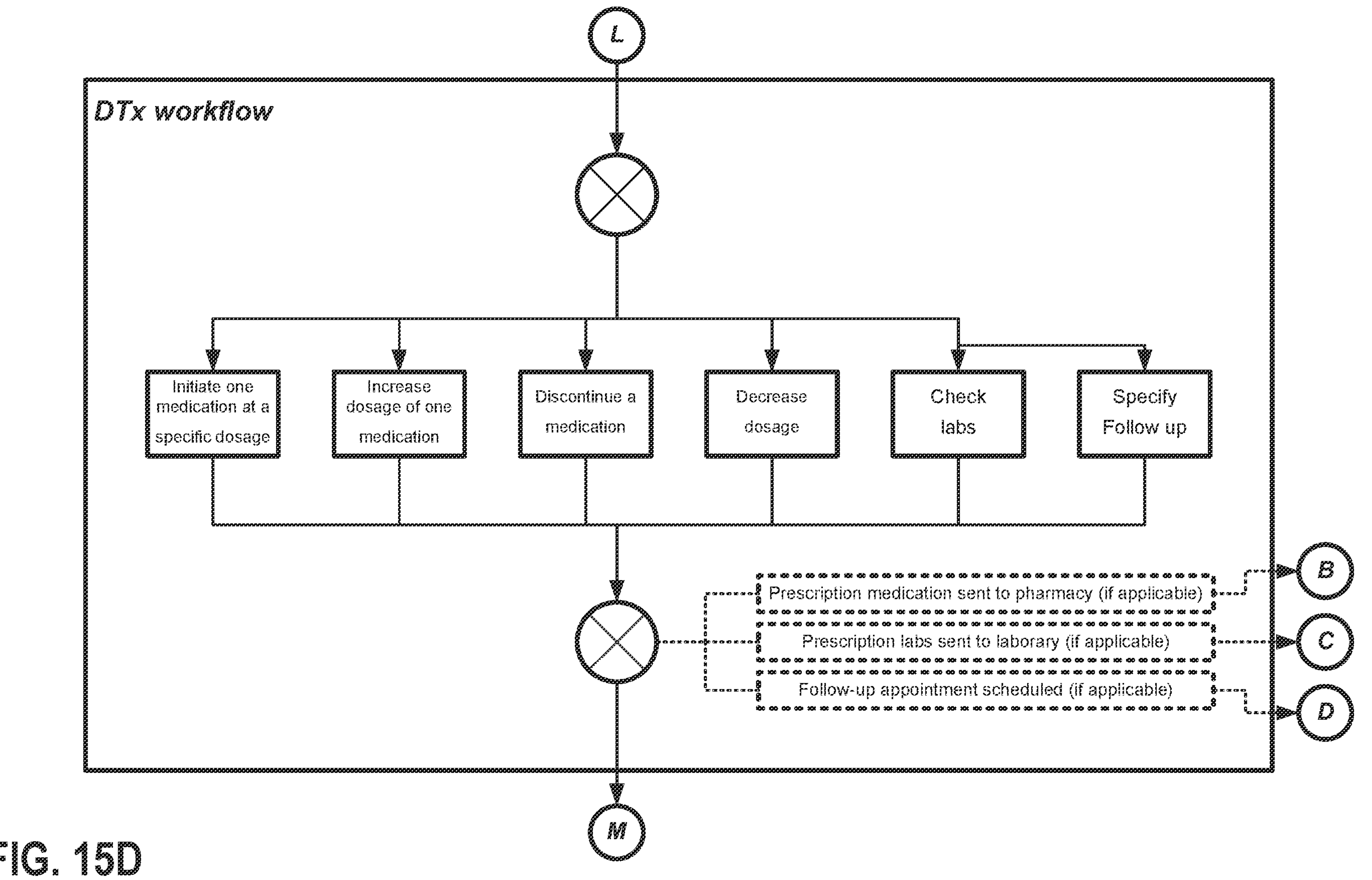
Figure 15E:
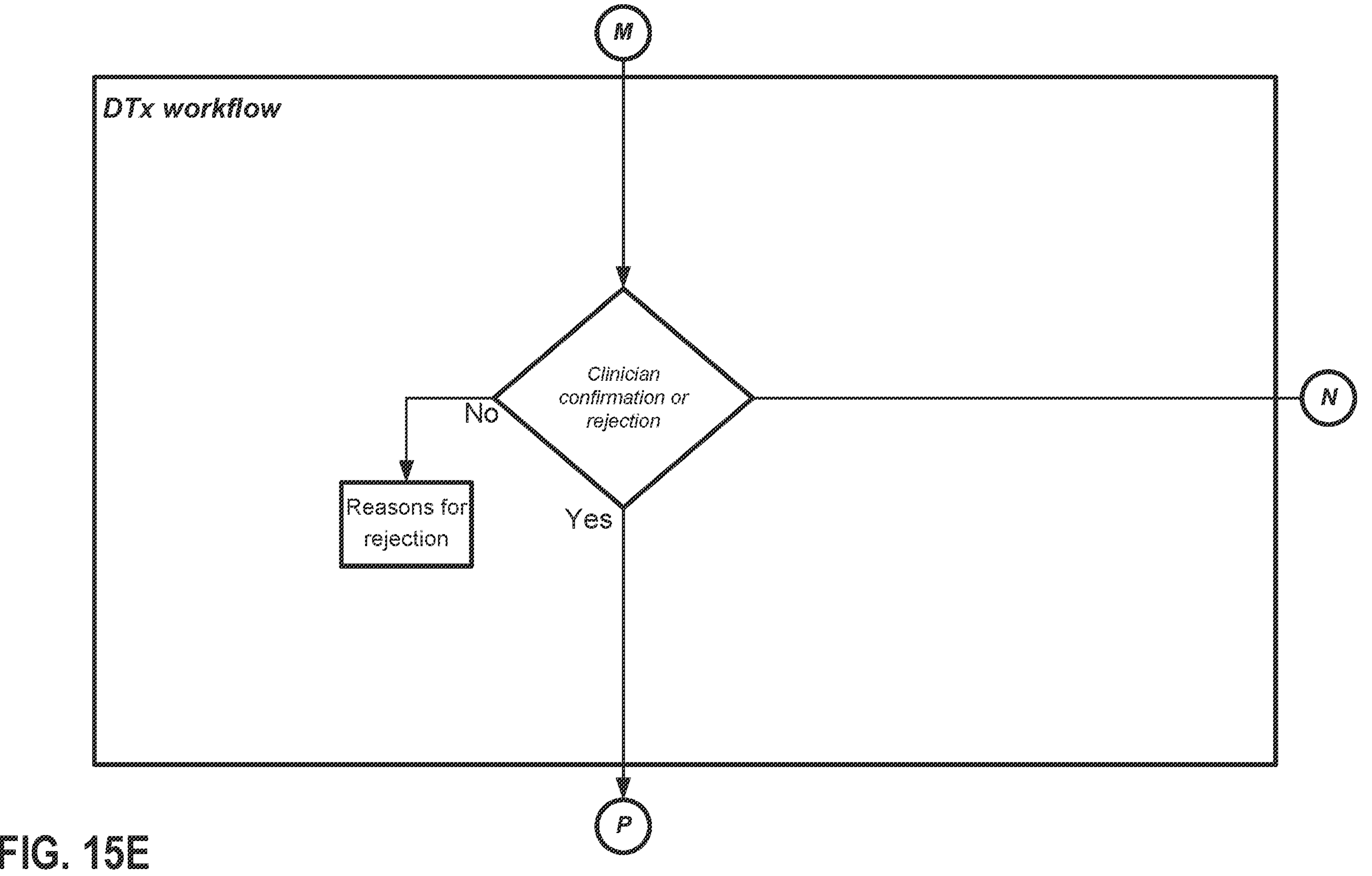
Figure 15F:
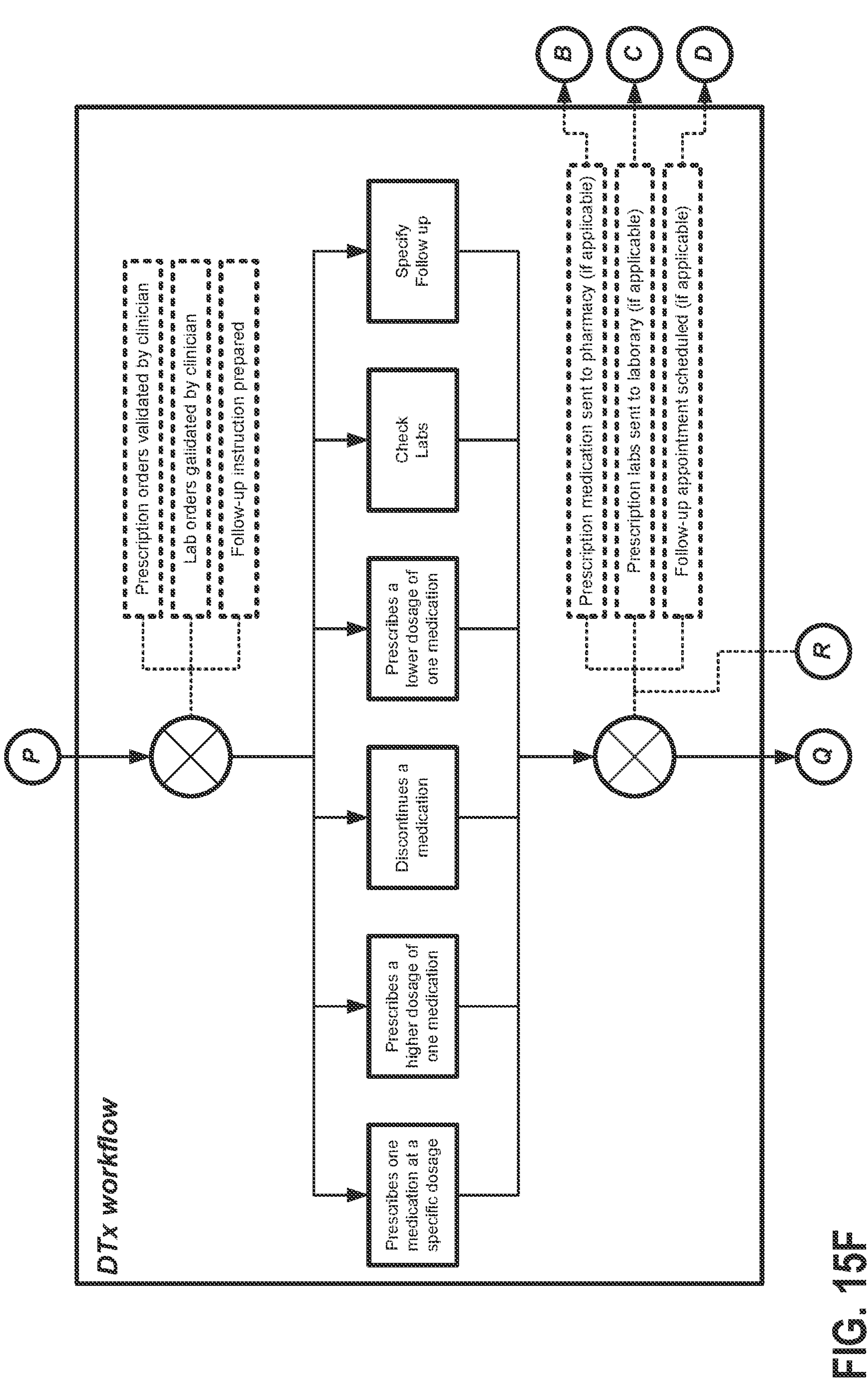
Figure 15G:
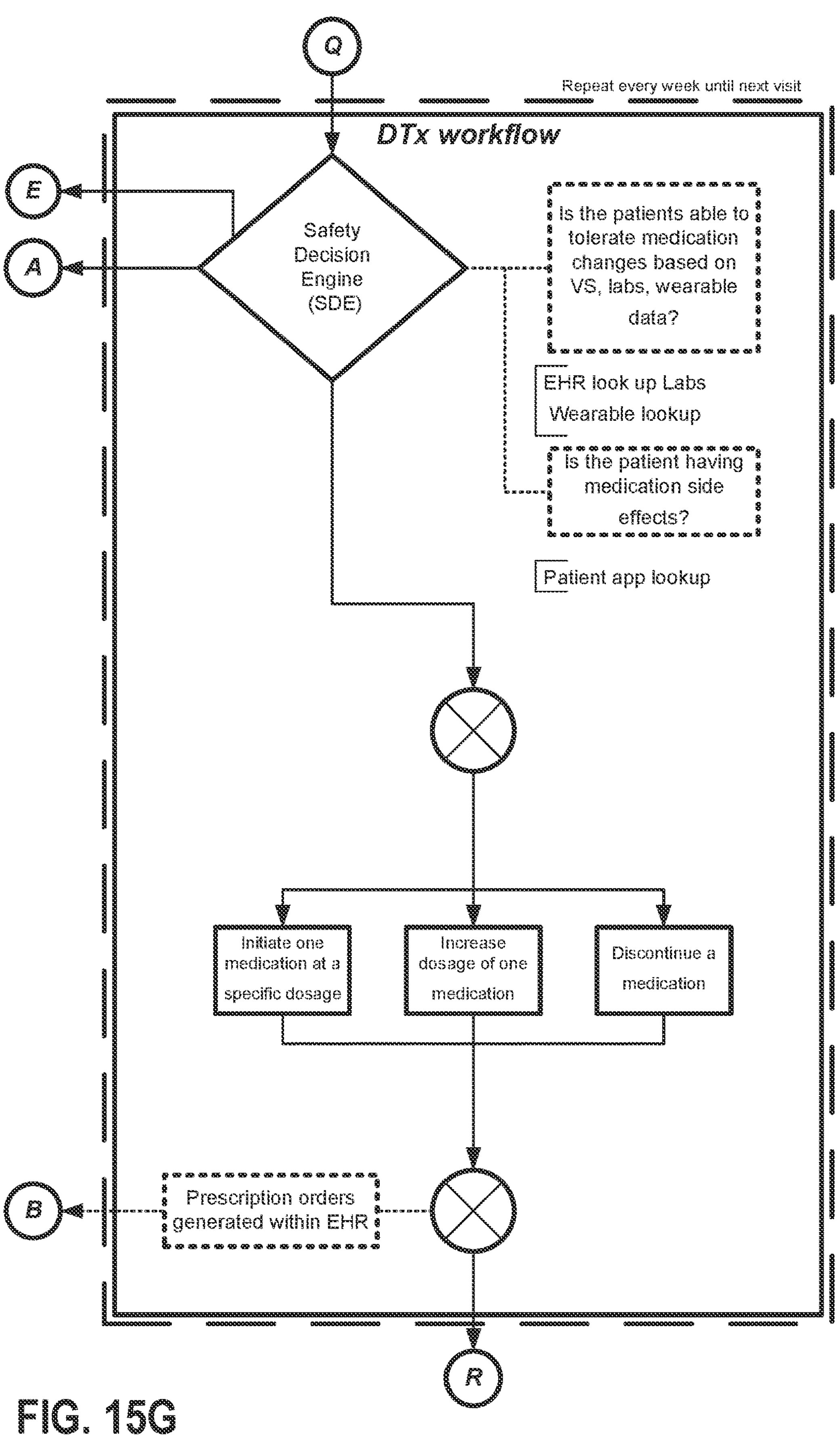
Figure 15H:
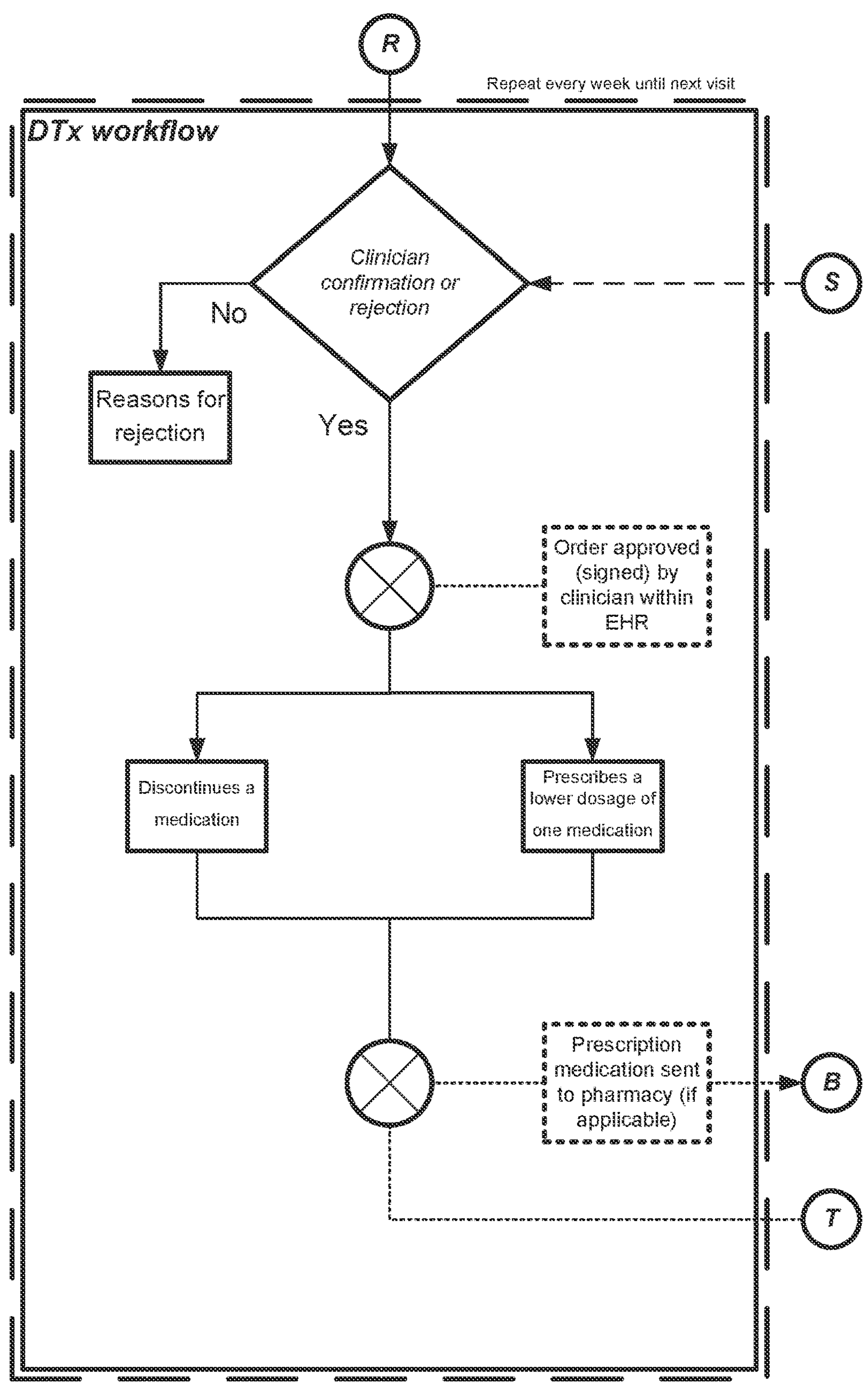
Figure 15I:
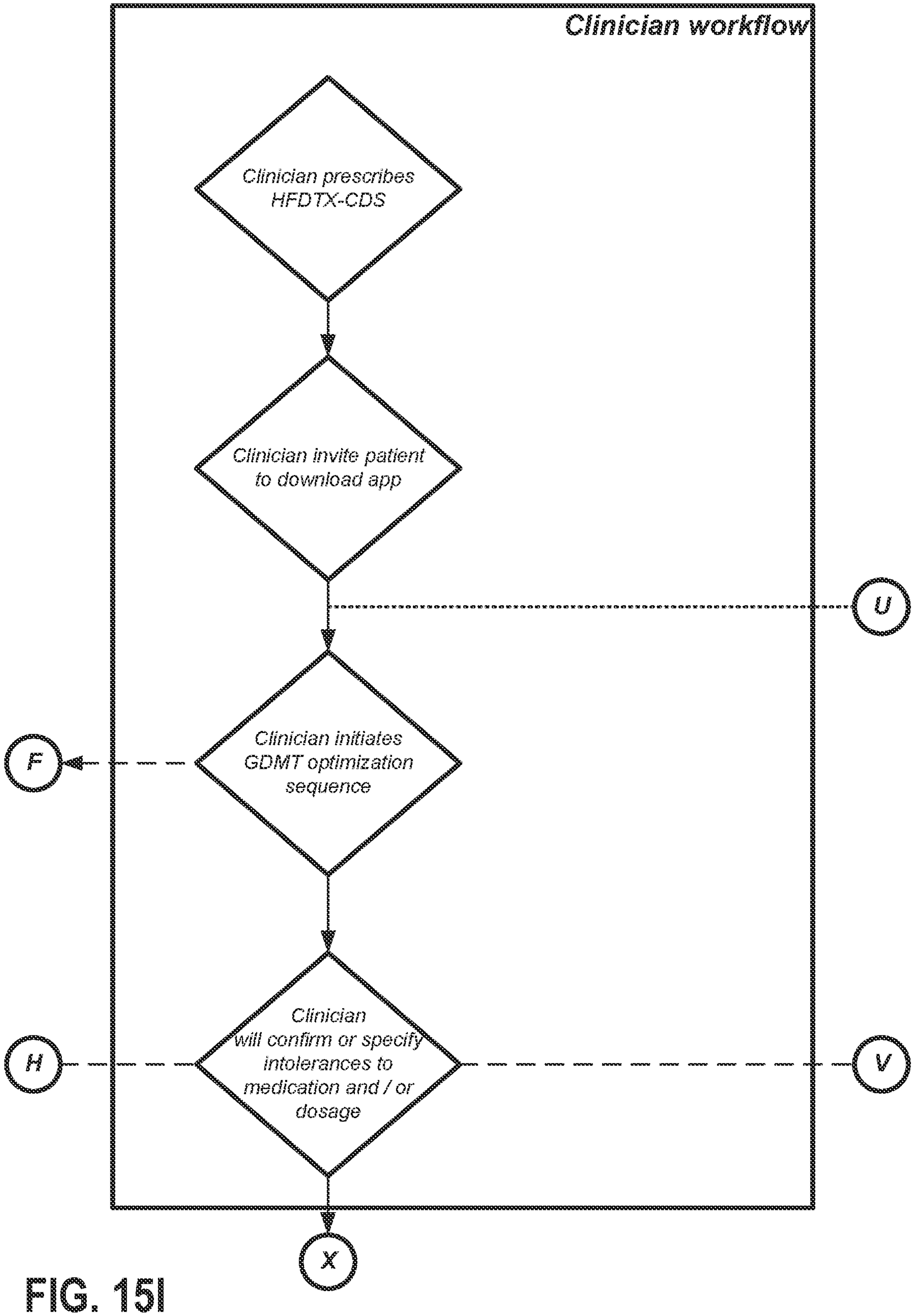
Figure 15J:
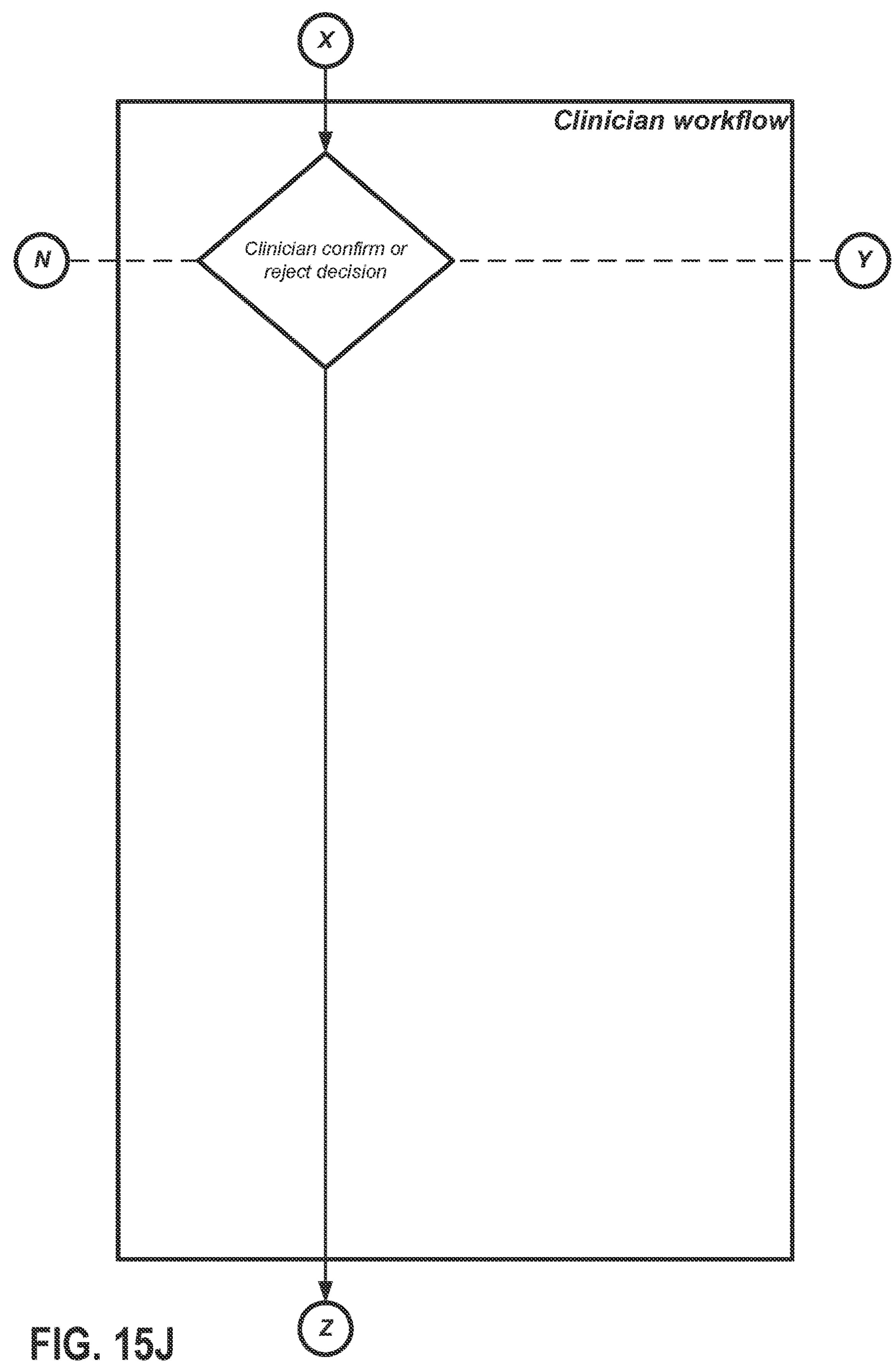
Figure 15K:
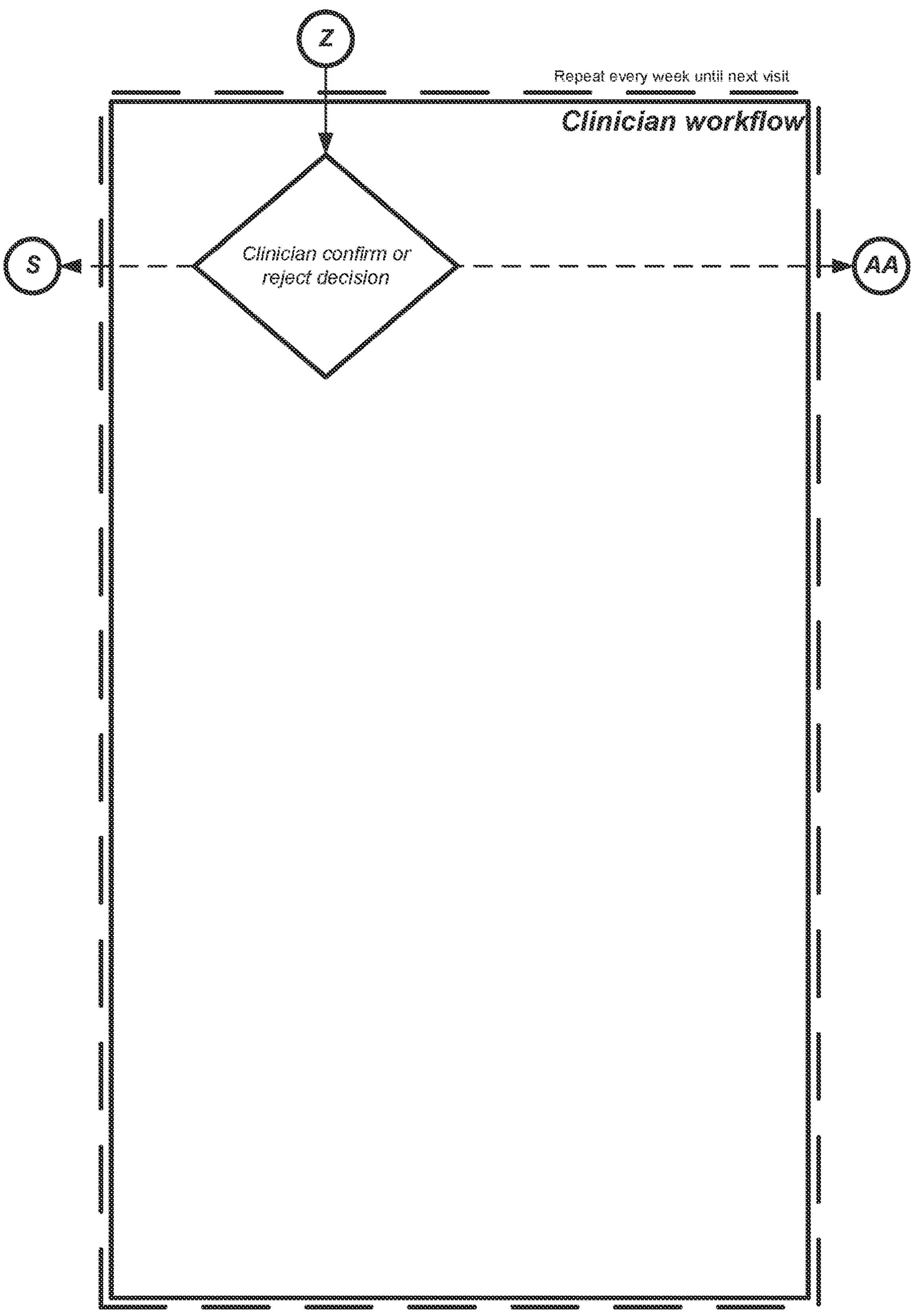
Figure 15L:
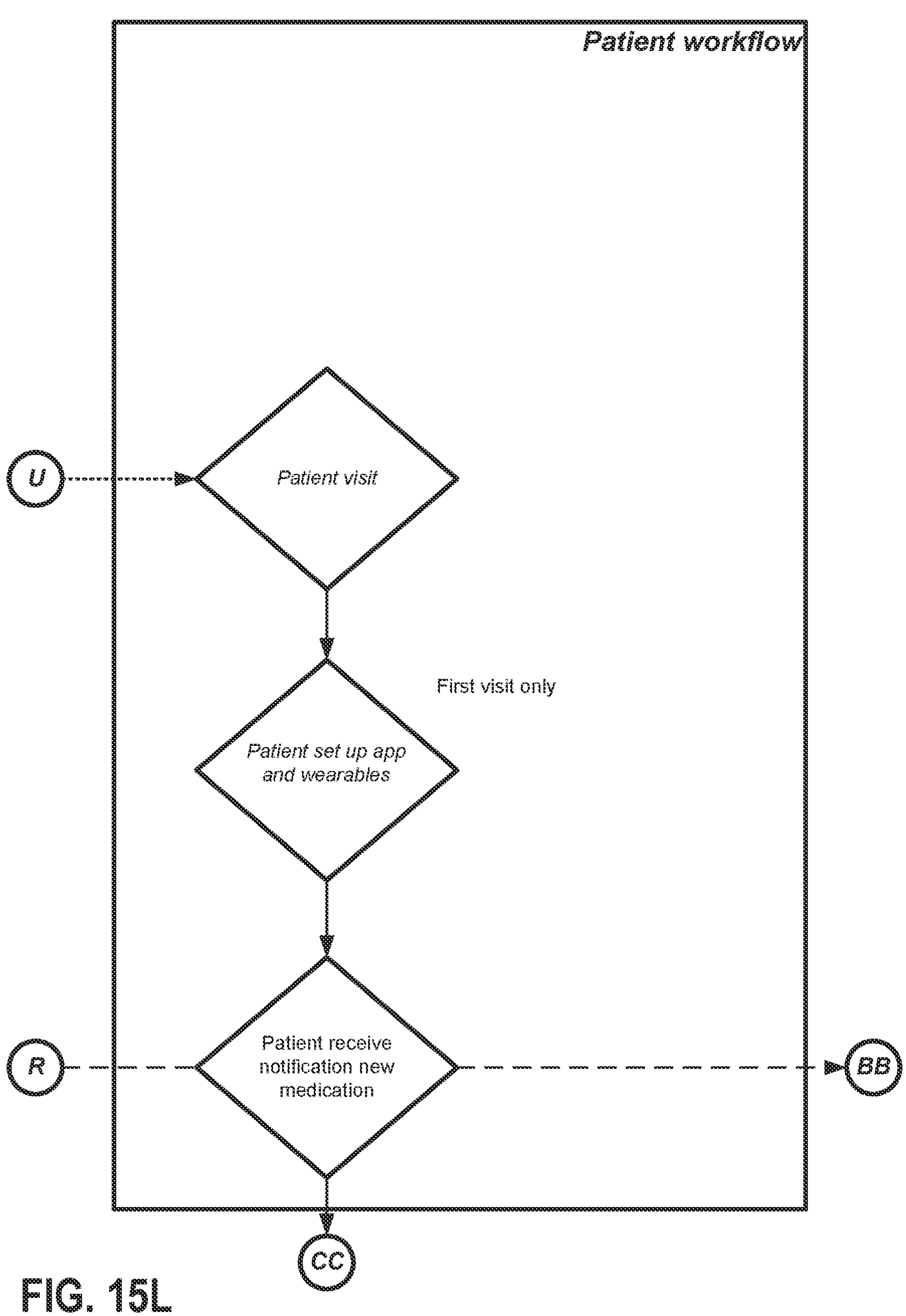
Figure 15M:
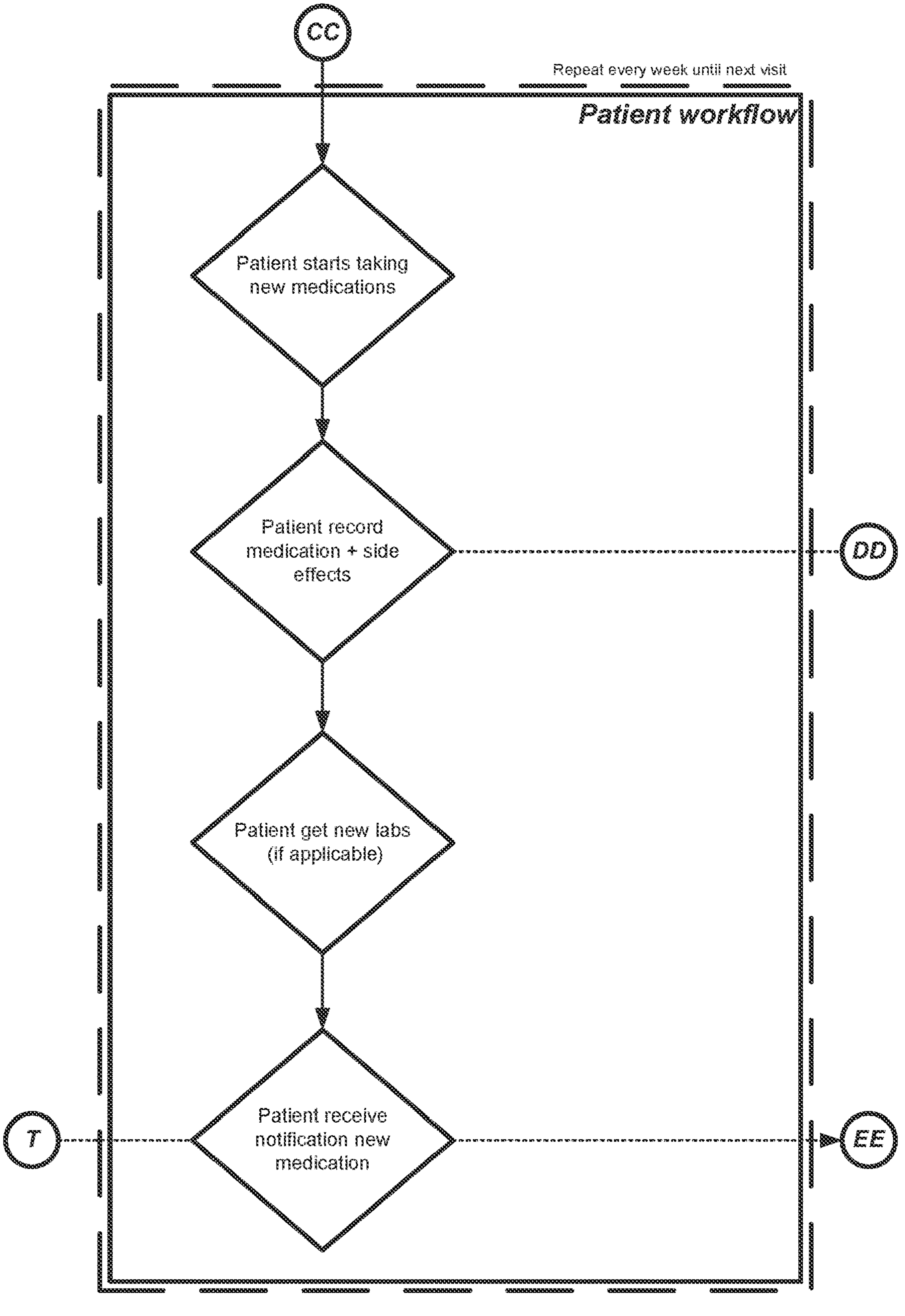
Figure 15N:
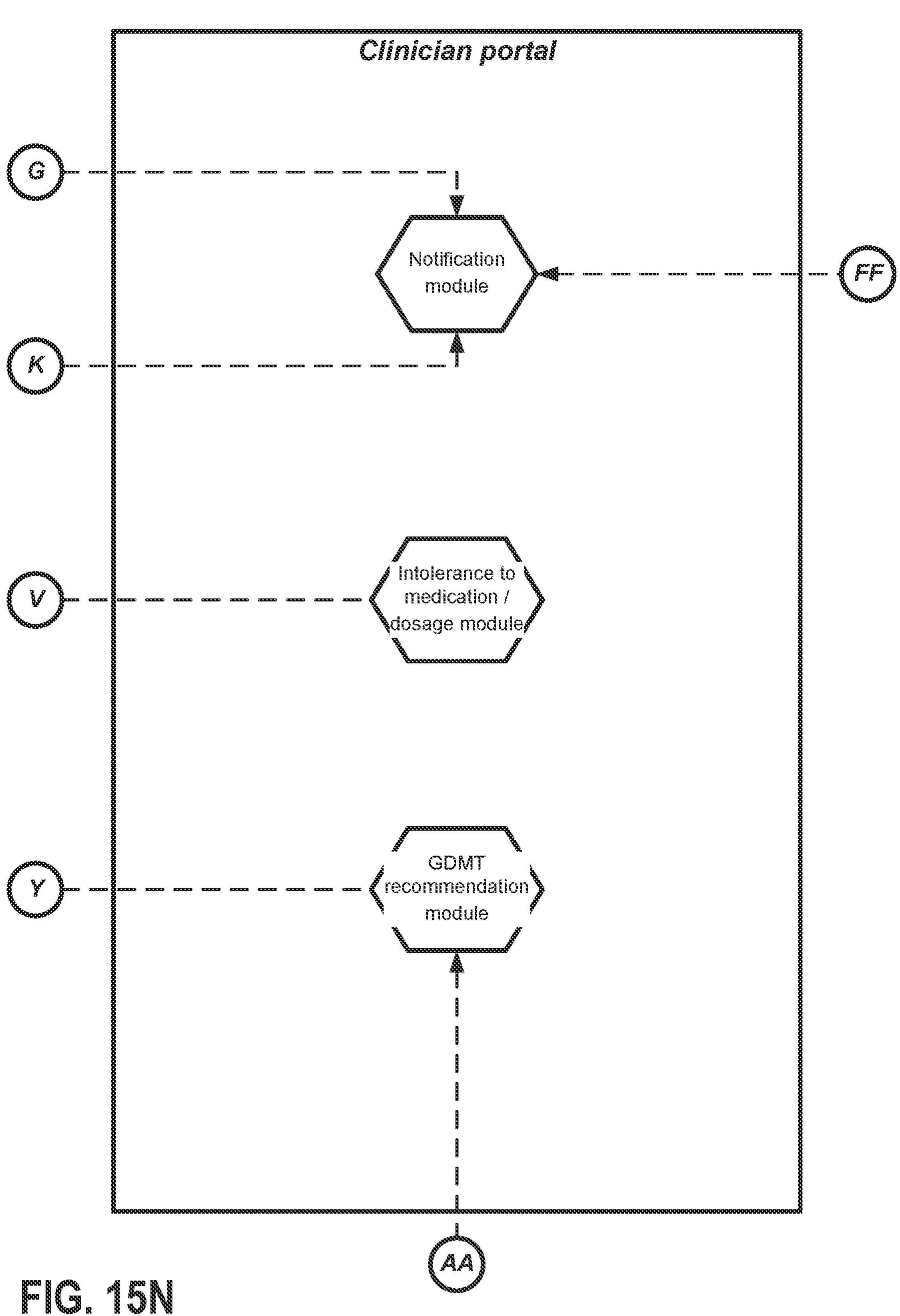
Figure 150:
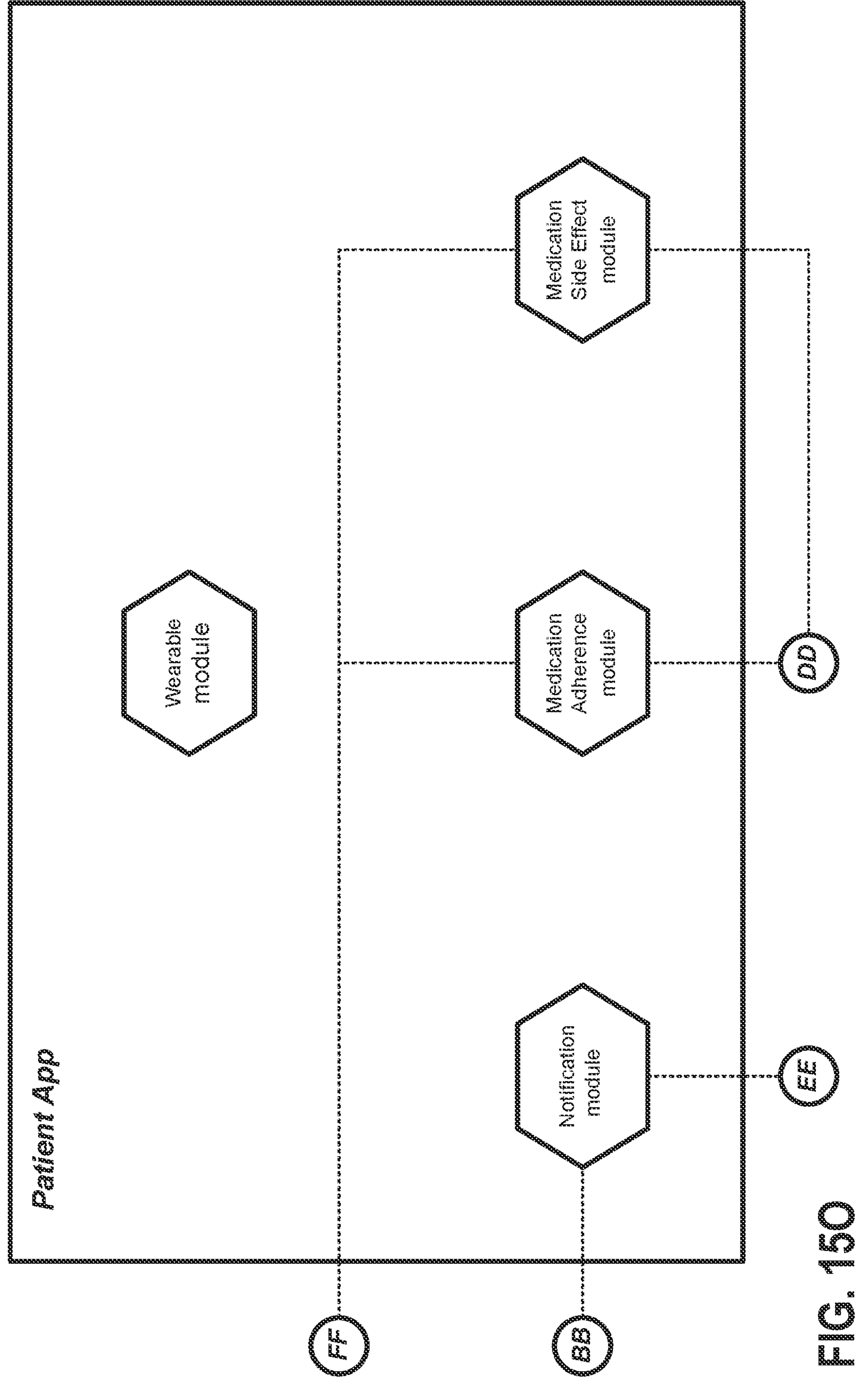

FIGS. 15A-15O show the electronic health record (HER) system, the decision engine workflow, the clinician workflow and the clinician portal, and the patient-side workflow and the patient app, according to an embodiment. In one example, the decision engine is validated based on an automated testing harness.

In one embodiment, a method, comprises generating an updated therapeutic regimen for a heart failure patient based on one or more physiological parameters of the patient acquired via one or more remote monitoring devices and a set of patient data acquired via the patient's health record; and administering the updated therapeutic regimen to the patient; wherein the updated therapeutic regimen comprises one or more of an increase in dosage of an at least one previously administered therapeutic agent and an initiation of a new therapeutic agent, the new therapeutic agent different than the previously administered therapeutic agent. Alternatively, the updated regimen comprises a decrease or discontinuation in dosage of the previously administered therapeutic agent.

In another embodiment, a method comprises receiving a set of heart rate data for a patient with a heart failure condition output from a wearable sensor; receiving a patient profile referenced to the patient comprising a therapeutic dosage regimen comprising at least one therapeutic and an associated dosage; processing the set of heart rate data using a model to modify the therapeutic dosage regimen and output an updated therapeutic dosage regime; and administering to the patient the updated therapeutic dosage regime. In a first example of the method, processing the set of heart rate data using the model to modify the therapeutic dosage regimen further comprises: receiving a set of blood pressure data output from a blood pressure sensor; and processing the set of blood pressure data using the model. In a second example of the method, which optionally includes the first example, the set of heart rate data comprises an average heart rate over 1, 2, 3, 4, 5, or 6 hours. In a third example of the method, which optionally includes one or more of the first and the second examples, the set of heart rate data comprises an average weekly heart rate. In a fourth example of the method, which optionally includes one or more of the first through third examples, the model comprises comparing the set of heart rate data to a predetermined threshold heart rate. In a fifth example of the method, which optionally includes one or more of the first through fourth examples, the at least one therapeutic is at least one beta-blocker chosen from atenolol, betaxolol, bisoprolol, carvedilol, esmolol, labetalol, metoprolol, nadolol, pindolol, propranolol, sotalol, timolol, acebutalol, oxprenolol, carvedilol, and penbutolol. In a sixth example of the method, which optionally includes one or more of the first through fourth examples, the at least one therapeutic is at least one or more of bisoprolol, carvedilol, metoprolol succinate, captopril, enalapril, fosinopril, Lisinopril, perindopril, quinapril, Ramipril, trandalopril, candesartan, losartan, valsartan, olmesartan, sacubitril/valsartan, spironolactone, or eplerenone. In a seventh example of the method, which optionally includes one or more of the first through sixth examples, the patient profile comprises at least one first therapeutic previously administered to the patient and wherein the updated therapeutic dosage regime comprises at least a second therapeutic different than the at least one first therapeutic. In an eighth example of the method, which optionally includes one or more of the first through ninth examples, the set of heart rate data comprises an average weekly heart rate and the predetermined threshold heart rate comprises 55, 56, 57, 58, 59, 60, 61, 62, 63, 64, or 65 bpm. In a ninth example of the method, which optionally includes one or more of the first through eighth examples, the model comprises a set of therapeutics that are administered sequentially in a predetermined order. In a tenth example of the method, which optionally includes one or more of the first through ninth examples the set of heart rate data comprises an average heart rate for at least four hours and the predetermined threshold heart rate comprises less than 50 bpm. In an eleventh example of the method, which optionally includes one or more of the first through tenth examples, the model comprises determining at least one therapeutic based on a class of the at least one therapeutic and a set of classes of therapeutics previously administered to the patient.

In another embodiment, a method for managing a therapeutic regimen of a patient diagnosed with heart failure, the method comprising: receiving a first set of physiological sensor data acquired from the patient during a first time period, the first set of physiological sensor data output via a one or more remote monitoring devices; receiving a set of patient data from a patient profile referenced to the patient, the set of patient data including the therapeutic regimen comprising at least one therapeutic agent and an associated dosage; processing the first set of physiological sensor data and the set of patient data based on a patient stability to output an updated therapeutic regimen; and administering the updated therapeutic regimen to the patient. In a first example of the method, processing the first set of physiological sensor data and the set of patient data based on the patient stability comprises determining a stability score for the patient based on the first set of physiological sensor data, and outputting the updated therapeutic regimen responsive to the stability score greater than a threshold score; otherwise, continuing administering the therapeutic regimen to the patient without updates. In a second example of the method, which optionally includes the first example, the updated therapeutic regimen comprises a change in the associated dosage of the at least one therapeutic agent or at least a second therapeutic agent and a second associated dosage for the second therapeutic agent, the second therapeutic agent different than the at least one therapeutic agent. In a third example of the method, which optionally includes one or more of the first and the second examples, the updated therapeutic regimen comprises discontinuation of the at least one therapeutic agent. In a fourth example of the method, which optionally includes one or more of the first through third examples, processing the first set of physiological sensor data and the set of patient data to output the updated therapeutic regimen further comprises generating one or more alerts, the one or more alerts comprising an indication to perform one or more of a laboratory test and an imaging test. In a fifth example of the method, which optionally includes one or more of the first through fourth examples, monitoring a patient response to the updated therapeutic regimen through one or more of a set of indications received from the patient and a second set of physiological sensor data acquired from the patient during a second time period, the second set of physiological sensor data output via the one or more remote monitoring devices; and responsive to the patient response indicating one or more of an intolerance to the updated regimen and a side-effect to the updated regimen, processing the second set of physiological sensor data and the set of patient data to output a second updated therapeutic regimen, and administering the second updated therapeutic regimen to the patient; otherwise, continuing administering the updated therapeutic regimen. In a sixth example of the method, which optionally includes one or more of the first through fifth examples, the second updated therapeutic regimen comprises a change in the second associated dosage of the second therapeutic agent or discontinuation of the second therapeutic agent. In a seventh example of the method, which optionally includes one or more of the first through sixth examples, the second set of physiological sensor data and the set of patient data to output the second updated therapeutic regimen is based on one or more of a potassium level, a delta creatinine level, a minimum systolic blood pressure, an average systolic blood pressure, and an average heart rate. In an eighth example of the method, which optionally includes one or more of the first through seventh examples, processing the first set of physiological sensor data and the set of patient data to output the updated therapeutic regimen is based on a guideline-directed medical therapy (GDMT). In a ninth example of the method, which optionally includes one or more of the first through eighth examples, the first set of physiological sensor data includes one or more of electrocardiogram (ECG) data for measuring an average heart rate of the patient and blood pressure data for measuring an average systolic blood pressure, an average diastolic blood pressure, and a minimum systolic blood pressure; and wherein the patient data includes one or more of a potassium level, a delta creatinine level, a creatinine level, an eGFR level, a left ventricular ejection fraction, a type of heart failure, a patient height, a patient weight, and a patient sex. In a tenth example of the method, which optionally includes one or more of the first through ninth examples the first set of physiological sensor data further includes one or more of a gyroscope data and an accelerometer data for measuring a degree of sway of the patient. In a eleventh example of the method, which optionally includes one or more of the first through tenth examples wherein the stability score is based on one or more of the average heart rate, the average systolic blood pressure, and the degree of sway of the patient. In a twelfth example of the method, which optionally includes one or more of the first through eleventh examples at least one of the one or more remote monitoring devices is a wearable device. In a thirteenth example of the method, which optionally includes one or more of the first through twelfth examples the at least one therapeutic agent is at least one beta-blocker chosen from atenolol, betaxolol, bisoprolol, carvedilol, esmolol, labetalol, metoprolol, nadolol, pindolol, propranolol, sotalol, timolol, acebutalol, oxprenolol, carvedilol, and penbutolol. In a fourteenth example of the method, which optionally includes one or more of the first through thirteenth examples, the at least one therapeutic agent is at least one or more of Bisoprolol, Carvedilol, Metoprolol Succinate, Captopril, Enalapril, Fosinopril, Lisinopril, Perindopril, Quinapril, Ramipril, Trandalopril, Candesartan, Losartan, Valsartan, Olmesartan, Sacubitril/Valsartan, Spironolactone, Eplerenone, Dapagliflozin, Empagliflosin, Canagliflozin, and Ertugliflosin. In a fifteenth example of the method, which optionally includes one or more of the first through fourteenth examples each of the at least one therapeutic agent and the at least second therapeutic agent is selected from the group consisting of beta blockers, Angiotensin-converting enzyme (ACE) inhibitors, angiotensin receptor blockers (ARBs), Angiotensin receptor-neprilysin inhibitors (ARNis), Aldosterone receptor antagonists (MRAs), Sodium-glucose transport protein (SGLT2) inhibitors, and other therapeutic agents for treating heart failure.

In another embodiment, a method comprises: generating an updated therapeutic regimen for a patient diagnosed with heart failure based on a first set of physiological parameters of the patient acquired via one or more remote monitoring devices and a set of patient data acquired via the patient's health record; and administering the updated therapeutic regimen to the patient; wherein the updated therapeutic regimen comprises a change in dosage of at least one previously administered therapeutic agent and/or an initiation of at one new therapeutic agent, the new therapeutic agent different from the previously administered therapeutic agent. In a first example of the method, generating the updated therapeutic regimen is based on a stability of a patient to tolerate up-titration of the at least one previously administered therapeutic agent and/or the initiation of the at least one new therapeutic agent. In a second example of the method which optionally includes the first example, the stability of the patient is based on one or more of an average heart rate within a threshold heart rate range, an average systolic blood pressure within a threshold systolic blood pressure range, and a degree of sway of the patient within a threshold range. In a third example of the method, which optionally includes one or more of the first and the second example, the method further comprises monitoring a patient response to the updated therapeutic regimen through one or more of a set of indications of side-effects received from the patient and a second set of physiological parameters acquired from the patient via the one or more remote monitoring devices after administering the updated therapeutic regimen; and responsive to the patient response indicating one or more of an intolerance to the updated regimen and a side-effect to the updated regimen, generating a second updated therapeutic regimen based on the second set of physiological parameters and the set of patient data, and administering the second updated therapeutic regimen to the patient; otherwise, continuing administering the updated therapeutic regimen. In a fourth example of the method, which optionally includes one or more of the first through third example, the first set of physiological parameters include one or more of an average heart rate, an average systolic blood pressure, an average diastolic blood pressure, and a minimum systolic blood pressure; and wherein the patient data includes one or more of a potassium level, a delta creatinine level, a creatinine level, an eGFR level, a left ventricular ejection fraction, a type of heart failure, a patient height, a patient weight, and a patient sex. In a fifth example of the method, which optionally includes one or more of the first through fourth examples, wherein administering the updated regimen to the patient comprises automatically storing the updated therapeutic regimen within the patient's health record and transmitting a notification to the patient, the notification including the new therapeutic agent in the updated regimen and an instructional indication regarding the new therapeutic agent. In a sixth example of the method, which optionally includes one or more of the first through fifth examples, the method includes automatically transmitting the updated therapeutic regimen to an associated pharmacy computing system referenced in the patient's health record. In a seventh example of the method, which optionally includes one or more of the first through sixth examples, each of the at least one previously administered therapeutic agent and the at least one new therapeutic agent is selected from the group consisting of beta blockers, Angiotensin-converting enzyme (ACE) inhibitors, angiotensin receptor blockers (ARBs), Angiotensin receptor-neprilysin inhibitors (ARNis), Aldosterone receptor antagonists (MRAs), Sodium-glucose transport protein (SGLT2) inhibitors, and other therapeutic agents for treating heart failure.

In another embodiment, a system for managing a therapeutic regimen for a patient with heart failure comprises one or more physiological sensors configured to acquire a set of physiological sensor data from the patient; a processing system comprising at least one processor communicably coupled to at least one non-transitory memory storing a decision engine, the at least one non-transitory memory storing executable instructions that when executed causes the processor to: acquire the set of physiological sensor data from the one or more physiological sensors; acquire a set of patient data from an electronic health record system communicatively coupled to the processor, the electronic health record system storing patient data referenced to the patient, the patient data including one or more therapeutic agents and associated dosages; during a first condition, when a stability of the patient is above a first threshold, process the set of physiological sensor data and the set of patient data according to a first mode of operation of the decision engine and output a first updated therapeutic regimen based on the therapeutic regimen, the therapeutic regimen including the one or more therapeutic agents and associated dosages; and during a second condition, when the stability of the patient is below the first threshold, process the set of physiological sensor data and the set of patient data according to a second mode of operation of the decision engine and output a second updated therapeutic regimen based on the therapeutic regimen. In a first example of the system, the set of physiological sensor data includes one or more of electrocardiogram (ECG) data, blood pressure data, photoplethysmogram (PPG) data, gyroscope data, accelerometer data, and body temperature data. In a second example of the system, which optionally includes the first example, wherein the stability of the patient is determined based on the set of physiological sensor data. In a third example of the system, which optionally includes one or more of the first and the second examples, the first mode of operation of the decision engine includes updating the therapeutic regimen to provide a change in associated dosage of the one or more therapeutic agents and/or initiate one or more new therapeutic agents, or to provide a discontinuation of the one or more therapeutic agents and/or initiate the one or more new therapeutic agents; and wherein the second mode of operation of the decision engine updates the therapeutic regimen to provide one or more of a decrease in the one or more therapeutic agents or discontinuation of the one or more therapeutic agents without initiating the one or more new therapeutic agents. In a fourth example of the system, which optionally includes one or more of the first through third examples, each of the one or more therapeutic agents and the one or more new therapeutic agents is selected from the group consisting of beta blockers, Angiotensin-converting enzyme (ACE) inhibitors, angiotensin receptor blockers (ARBs), Angiotensin receptor-neprilysin inhibitors (ARNis), Aldosterone receptor antagonists (MRAs), Sodium-glucose transport protein (SGLT2) inhibitors, and other therapeutic agents for treating heart failure.

In one representation, a method for treating a patient diagnosed with heart failure, the method comprises: modulating, via a processor, a current therapeutic regimen for the patient based on one or more outputs from one or more remote patient monitoring devices and/or one or more patient data from a patient electronic profile referenced to the patient; wherein the current therapeutic regimen comprises one or more therapeutic agents and associated dosages; and wherein the one or more patient monitoring devices includes one or more blood pressure sensors, one or more ECG sensors, one or more gyroscopes, and/or one or more accelerometers. In one example, the method further comprises administering the modulated therapeutic regiment to the patient. In a second example, which optionally includes the first method, the method further comprises monitoring response to the modulated therapeutic regimen based on the one or more remote monitoring devices and/or the one or more patient data and/or input from the patient via a patient portal communicatively coupled to the processor. In a third example, which optionally includes one or more of the first and the second methods, modulating the current therapeutic regimen includes increasing or decreasing or discontinuing associated dosages of the one or more therapeutic agents. In a fourth example, which optionally includes one or more of the first through third examples, modulating the current therapeutic regimen includes initiating one or more new therapeutic agents, the one or more new therapeutic agents different from the one or more therapeutic agents. In a fifth example, which optionally includes one or more of the first through fourth examples, responsive to determining the patient stability is not below a threshold stability level, modulating the current therapeutic regimen to decrease or discontinue dosage of the one or more therapeutic agents; otherwise modulating the current therapeutic regimen to increase dosage of the one or more therapeutic agents and/or initiate the one or more new therapeutic agents. In a sixth example, which optionally includes one or more of the first through fifth examples, the one or more therapeutic agents are selected from the group consisting of beta blockers, Angiotensin-converting enzyme (ACE) inhibitors, angiotensin receptor blockers (ARBs), Angiotensin receptor-neprilysin inhibitors (ARNis), Aldosterone receptor antagonists (MRAs), Sodium-glucose transport protein (SGLT2) inhibitors, and other therapeutic agents for treating heart failure. In a seventh example, which optionally includes one or more of the first through sixth examples, the one or more new therapeutic agents are selected from the group consisting of beta blockers, Angiotensin-converting enzyme (ACE) inhibitors, angiotensin receptor blockers (ARBs), Angiotensin receptor-neprilysin inhibitors (ARNis), Aldosterone receptor antagonists (MRAs), Sodium-glucose transport protein (SGLT2) inhibitors, and other therapeutic agents for treating heart failure. In an eighth example, which optionally includes one or more of the first through seventh examples, the one or more remote patient monitoring devices are wearable devices.

Examples

The following examples are provided to better illustrate the claimed invention and are not intended to be interpreted as limiting the scope of the invention. To the extent that specific materials or steps are mentioned, it is merely for purposes of illustration and is not intended to limit the invention. One skilled in the art may develop equivalent means or reactants without the exercise of inventive capacity and without departing from the scope of the invention.

FIGS. 8A and 8B illustrates examples of an application user interface, that includes various patient information, patient history, and therapeutic history. Accordingly, the system may then output through the interface (e.g. a display, which is shown in dashed line), a new treatment regimen. As shown, the clinician interface includes options for the clinician to set various thresholds, including limits for the various medications. Further, the clinician interface outputs one or more alerts, including the decision states that were involved in modulating or updating a given therapeutic regimen.

FIGS. 9A and 9B illustrate tables showing various classes of drugs used to treat heart failure patients and various dosage levels. For instance, in some examples, various decision engines are disclosed that may titrate the dosages of the therapeutics to different levels listed in the table based on sensor data received by the system and other data as disclosed herein.

Figure 10B:
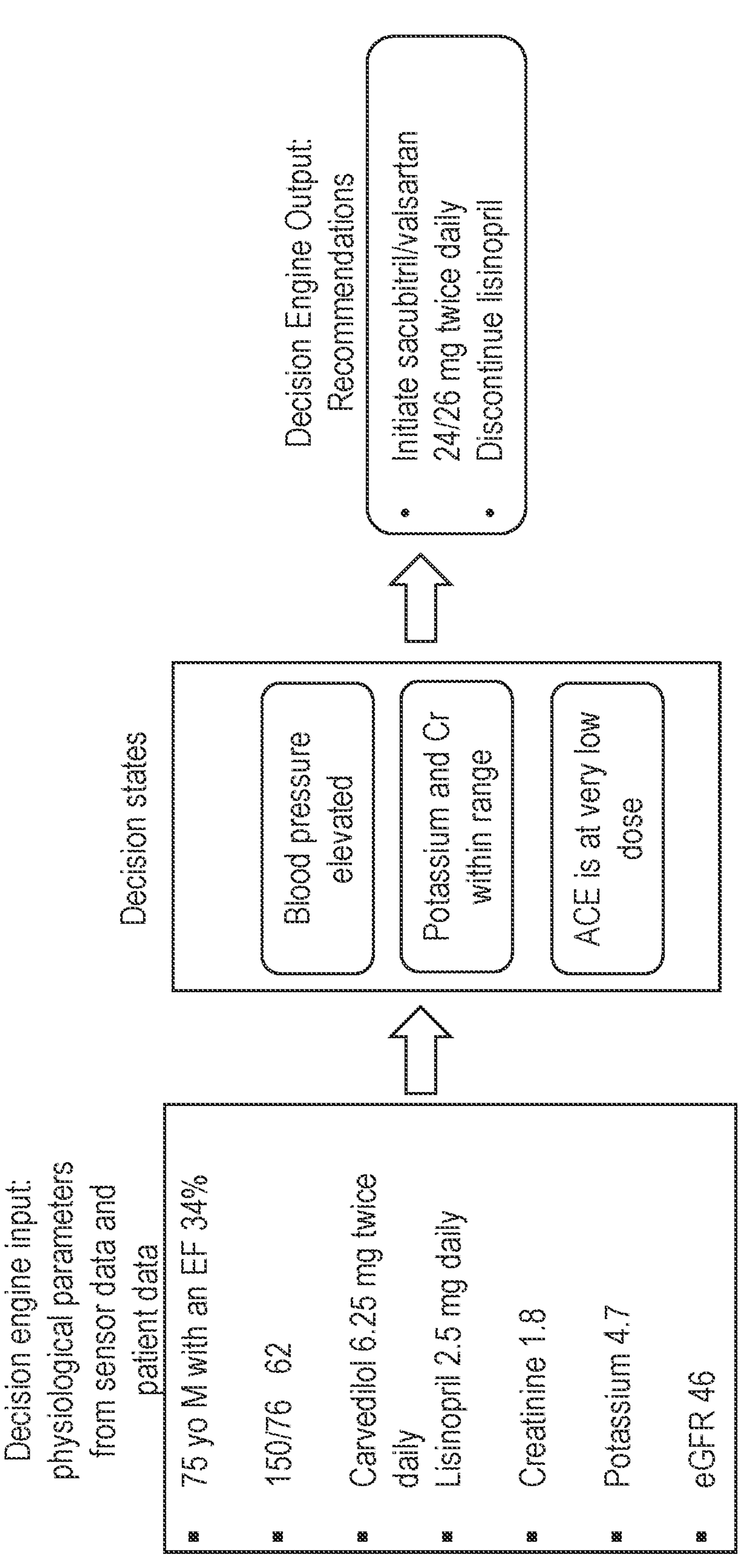

FIGS. 10A and 10B are block diagrams illustrating a first therapeutic regimen update and a second therapeutic regimen update for a first heart failure patient. FIGS. 10A and 10B show example decision engine inputs, decision engine evaluation states including logic that drive the output recommendations, and decision engine output recommendations for the first patient.

Figure 11A:
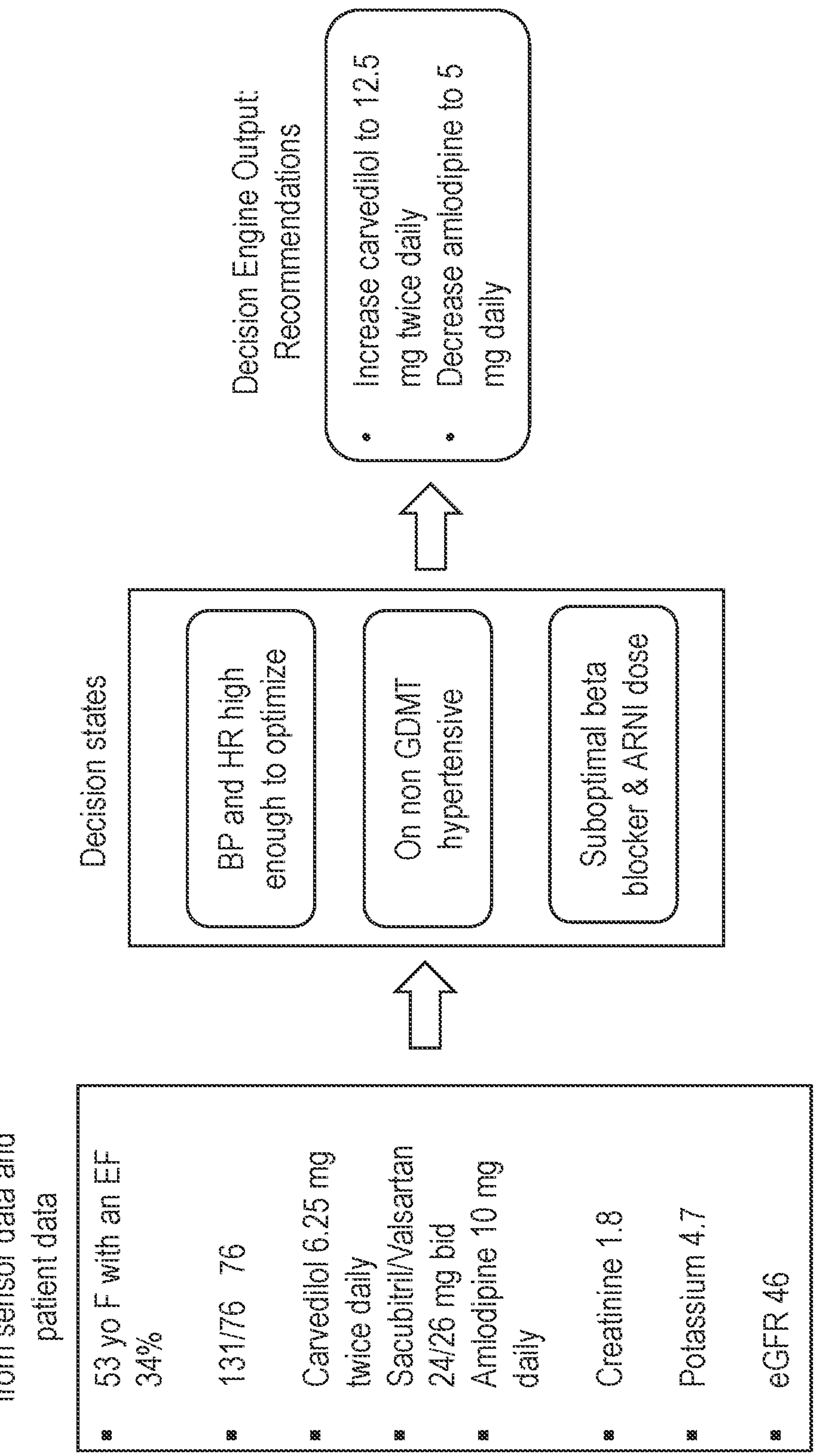
FIGS. 11A-11C show example inputs, example indication of decision states, and example outputs generated for another patient during respective updates of the therapeutic regimen of the patient, according to some implementations of the present disclosure.
Figure 11B:
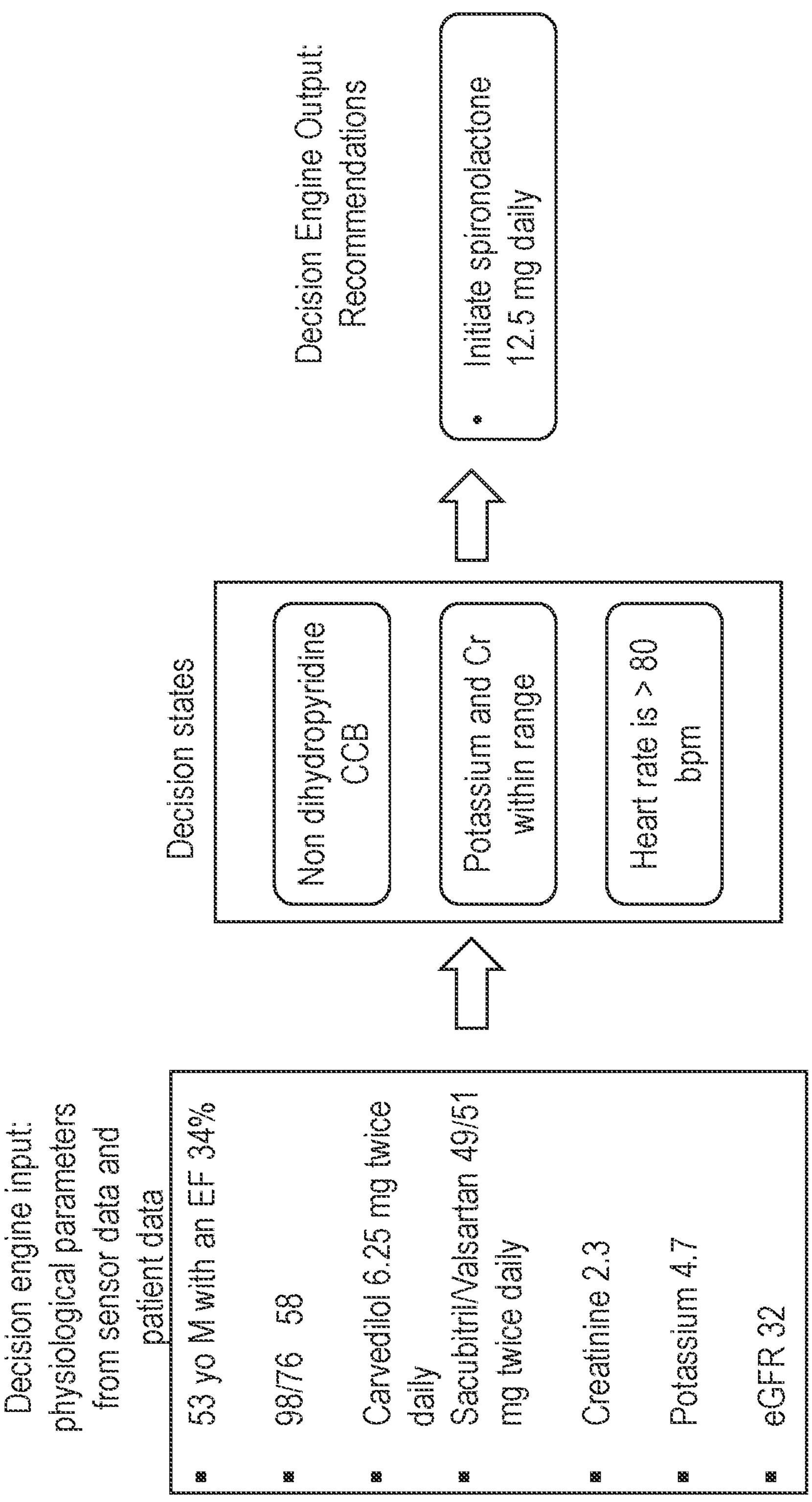
Figure 11C:
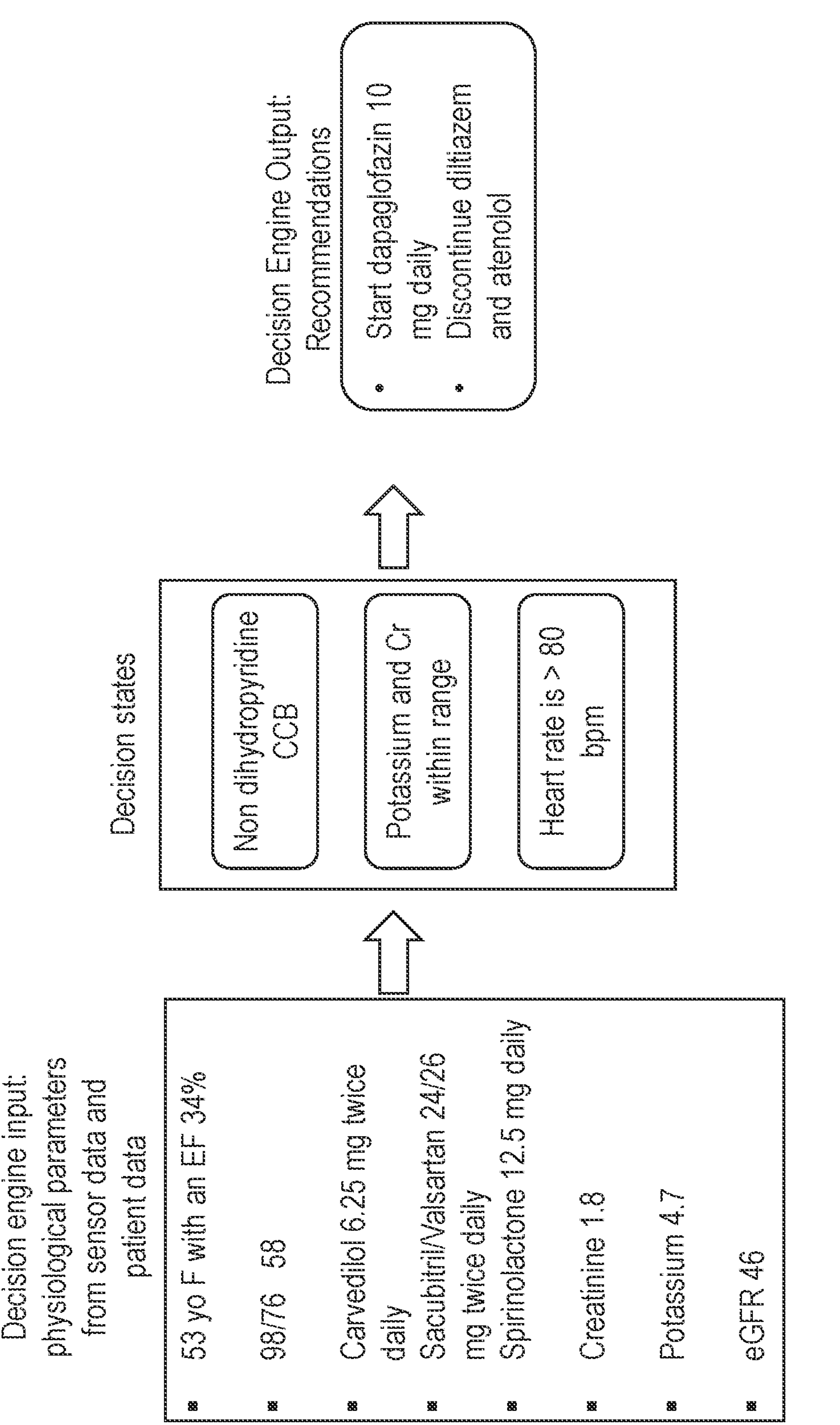

FIGS. 11A, 11B, and 11C are block diagrams illustrating a first therapeutic regimen update, a second therapeutic regimen update, and a third therapeutic regimen update for a second heart failure patient. FIGS. 11A, 11B, and 11C show example decision engine inputs, decision engine evaluation states including logic that drive the output recommendations, and decision engine output recommendations for the second patient.

Computer & Hardware Implementation of Disclosure

It should initially be understood that the disclosure herein may be implemented with any type of hardware and/or software, and may be a pre-programmed general purpose computing device. For example, the system may be implemented using a server, a personal computer, a portable computer, a thin client, or any suitable device or devices. The disclosure and/or components thereof may be a single device at a single location, or multiple devices at a single, or multiple, locations that are connected together using any appropriate communication protocols over any communication medium such as electric cable, fiber optic cable, or in a wireless manner.

It should also be noted that the disclosure is illustrated and discussed herein as having a plurality of modules which perform particular functions. It should be understood that these modules are merely schematically illustrated based on their function for clarity purposes only, and do not necessary represent specific hardware or software. In this regard, these modules may be hardware and/or software implemented to substantially perform the particular functions discussed. Moreover, the modules may be combined together within the disclosure, or divided into additional modules based on the particular function desired. Thus, the disclosure should not be construed to limit the present invention, but merely be understood to illustrate one example implementation thereof.

The computing system can include clients and servers. A client and server are generally remote from each other and typically interact through a communication network. The relationship of client and server arises by virtue of computer programs running on the respective computers and having a client-server relationship to each other. In some implementations, a server transmits data (e.g., an HTML page) to a client device (e.g., for purposes of displaying data to and receiving user input from a user interacting with the client device). Data generated at the client device (e.g., a result of the user interaction) can be received from the client device at the server.

Implementations of the subject matter described in this specification can be implemented in a computing system that includes a back-end component, e.g., as a data server, or that includes a middleware component, e.g., an application server, or that includes a front-end component, e.g., a client computer having a graphical user interface or a Web browser through which a user can interact with an implementation of the subject matter described in this specification, or any combination of one or more such back-end, middleware, or front-end components. The components of the system can be interconnected by any form or medium of digital data communication, e.g., a communication network. Examples of communication networks include a local area network ("LAN") and a wide area network ("WAN"), an internetwork (e.g., the Internet), and peer-to-peer networks (e.g., ad hoc peer-to-peer networks).

Implementations of the subject matter and the operations described in this specification can be implemented in digital electronic circuitry, or in computer software, firmware, or hardware, including the structures disclosed in this specification and their structural equivalents, or in combinations of one or more of them. Implementations of the subject matter described in this specification can be implemented as one or more computer programs, i.e., one or more modules of computer program instructions, encoded on computer storage medium for execution by, or to control the operation of, data processing apparatus. Alternatively or in addition, the program instructions can be encoded on an artificially-generated propagated signal, e.g., a machine-generated electrical, optical, or electromagnetic signal that is generated to encode information for transmission to suitable receiver apparatus for execution by a data processing apparatus. A computer storage medium can be, or be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially-generated propagated signal. The computer storage medium can also be, or be included in, one or more separate physical components or media (e.g., multiple CDs, disks, or other storage devices).

The operations described in this specification can be implemented as operations performed by a "data processing apparatus" on data stored on one or more computer-readable storage devices or received from other sources.

The term "data processing apparatus" encompasses all kinds of apparatus, devices, and machines for processing data, including by way of example a programmable processor, a computer, a system on a chip, or multiple ones, or combinations, of the foregoing The apparatus can include special purpose logic circuitry, e.g., an FPGA (field programmable gate array) or an ASIC (application-specific integrated circuit). The apparatus can also include, in addition to hardware, code that creates an execution environment for the computer program in question, e.g., code that constitutes processor firmware, a protocol stack, a database management system, an operating system, a cross-platform runtime environment, a virtual machine, or a combination of one or more of them. The apparatus and execution environment can realize various different computing model infrastructures, such as web services, distributed computing and grid computing infrastructures.

A computer program (also known as a program, software, software application, script, or code) can be written in any form of programming language, including compiled or interpreted languages, declarative or procedural languages, and it can be deployed in any form, including as a stand-alone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub-programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform actions by operating on input data and generating output. The processes and logic flows can also be performed by, and apparatus can also be implemented as, special purpose logic circuitry, e.g., an FPGA (field programmable gate array) or an ASIC (application-specific integrated circuit).

Processors suitable for the execution of a computer program include, by way of example, both general and special purpose microprocessors, and any one or more processors of any kind of digital computer. Generally, a processor will receive instructions and data from a read-only memory or a random access memory or both. The essential elements of a computer are a processor for performing actions in accordance with instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device (e.g., a universal serial bus (USB) flash drive), to name just a few. Devices suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks. The processor and the memory can be supplemented by, or incorporated in, special purpose logic circuitry.

CONCLUSION

The various methods and techniques described above provide a number of ways to carry out the invention. Of course, it is to be understood that not necessarily all objectives or advantages described can be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as taught or suggested herein. A variety of alternatives are mentioned herein. It is to be understood that some embodiments specifically include one, another, or several features, while others specifically exclude one, another, or several features, while still others mitigate a particular feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be employed in various combinations by one of ordinary skill in this art to perform methods in accordance with the principles described herein. Among the various elements, features, and steps some will be specifically included and others specifically excluded in diverse embodiments.

Although the application has been disclosed in the context of certain embodiments and examples, it will be understood by those skilled in the art that the embodiments of the application extend beyond the specifically disclosed embodiments to other alternative embodiments and/or uses and modifications and equivalents thereof.

In some embodiments, the terms "a" and "an" and "the" and similar references used in the context of describing a particular embodiment of the application (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (for example, "such as") provided with respect to certain embodiments herein is intended merely to better illuminate the application and does not pose a limitation on the scope of the application otherwise claimed. No language in the specification should be construed as indicating any non-claimed element essential to the practice of the application.

Certain embodiments of this application are described herein. Variations on those embodiments will become apparent to those of ordinary skill in the art upon reading the foregoing description. It is contemplated that skilled artisans can employ such variations as appropriate, and the application can be practiced otherwise than specifically described herein. Accordingly, many embodiments of this application include all modifications and equivalents of the subject matter recited in the claims appended hereto as permitted by applicable law. Moreover, any combination of the above-described elements in all possible variations thereof is encompassed by the application unless otherwise indicated herein or otherwise clearly contradicted by context.

Particular implementations of the subject matter have been described. Other implementations are within the scope of the following claims. In some cases, the actions recited in the claims can be performed in a different order and still achieve desirable results. In addition, the processes depicted in the accompanying figures do not necessarily require the particular order shown, or sequential order, to achieve desirable results.

All patents, patent applications, publications of patent applications, and other material, such as articles, books, specifications, publications, documents, things, and/or the like, referenced herein are hereby incorporated herein by this reference in their entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that can be employed can be within the scope of the application. Thus, by way of example, but not of limitation, alternative configurations of the embodiments of the application can be utilized in accordance with the teachings herein. Accordingly, embodiments of the present application are not limited to that precisely as shown and described.

What is claimed is:

1. A system for managing an initial therapeutic regimen for a patient with heart failure, the system comprising:

one or more physiological sensors configured to acquire a set of physiological sensor data comprising at least heart rate data and blood pressure data from the patient;

a processing system comprising at least one processor communicably coupled to at least one non-transitory memory storing a decision engine, the at least one non-transitory memory storing executable instructions that when executed causes the processor to:

acquire the set of physiological sensor data from the one or more physiological sensors;

acquire a set of patient data from an electronic health record system communicatively coupled to the processor, the electronic health record system storing patient data referenced to the patient, the patient data including one or more therapeutic agents and associated dosages;

compute, from the set of physiological sensor data, a stability metric based on at least two physiological parameters;

compare the stability metric to a predefined stability threshold stored in the non-transitory memory and determine if clinician input is required;

during a first condition, when clinician input is not required and the stability metric exceeds the predefined stability threshold, process the set of physiological sensor data and the set of patient data according to a first mode of operation of the decision engine and output a first updated therapeutic regimen based on the initial therapeutic regimen, the initial therapeutic regimen including the one or more therapeutic agents and associated dosages, wherein the first mode maintains the initial therapeutic regimen and generates a first monitoring interval for subsequent acquisition of physiological sensor data; and during a second condition, when the stability metric falls below the predefined stability threshold, process the set of physiological sensor data and the set of patient data according to a second mode of operation of the decision engine and output a second updated therapeutic regimen based on the initial therapeutic regimen, wherein the second mode automatically generates the second updated therapeutic regimen according to a predefined dosage adjustment protocol stored in the non-transitory memory and transmits a control signal to a therapeutic administration device to implement the second updated therapeutic regimen;

wherein the decision engine automatically transitions between the first mode of operation and the second mode of operation based on recalculation of the stability metric.

2. The system of claim 1, wherein the set of physiological sensor data includes one or more of electrocardiogram (ECG) data, photoplethysmogram (PPG) data, gyroscope data, accelerometer data, and body temperature data.

3. The system of claim 1, wherein the stability of the patient is determined based on the set of physiological sensor data.

4. The system of claim 2, wherein the first mode of operation of the decision engine includes updating the initial therapeutic regimen to provide a change in associated dosage of the one or more therapeutic agents and/or initiate one or more new therapeutic agents, or to provide a discontinuation of the one or more therapeutic agents and/or initiate the one or more new therapeutic agents; and wherein the second mode of operation of the decision engine updates the initial therapeutic regimen to provide one or more of a decrease in the one or more therapeutic agents or discontinuation of the one or more therapeutic agents without initiating the one or more new therapeutic agents.

5. The system of claim 4, wherein each of the one or more therapeutic agents and the one or more new therapeutic agents is selected from the group consisting of beta blockers, Angiotensin-converting enzyme (ACE) inhibitors, angiotensin receptor blockers (ARBs), Angiotensin receptor-neprilysin inhibitors (ARNis), Aldosterone receptor antagonists (MRAs), Sodium-glucose transport protein (SGLT2) inhibitors, and other therapeutic agents for treating heart failure.

6. The system of claim 1, further comprising an automated testing harness module configured to run the decision engine using a plurality of patient datasets previously stored to evaluate one or more changes to the decision engine.

7. The system of claim 1, further comprising an automated testing harness module configured to run a plurality of simulations using previously stored patient profiles similar to a current patient to evaluate a clinician set threshold prior to initiating the decision engine.

8. The system of claim 1, further comprising a safety decision engine configured to manage a therapeutic regimen of a patient when the patient's stability metric is less than the predefined stability threshold.

* * * * *